(12) United States Patent
Dawoud et al.

(10) Patent No.: US 11,020,036 B2
(45) Date of Patent: Jun. 1, 2021

(54) METHOD AND SYSTEM TO DETECT R-WAVES IN CARDIAC ARRHYTHMIC PATTERNS

(71) Applicant: PACESETTER, INC., Sylmar, CA (US)

(72) Inventors: Fady Dawoud, Santa Monica, CA (US); Fujian Qu, San Jose, CA (US); Stuart Rosenberg, Castaic, CA (US); Gene A. Bornzin, Simi Valley, CA (US); Jong Gill, Valencia, CA (US); Neha Malhotra, Los Angeles, CA (US); Xiaoyi Min, Camarillo, CA (US)

(73) Assignee: PACESETTER, INC., Sylmar, CA (US)

( * ) Notice: Subject to any disclaimer, the term of this patent is extended or adjusted under 35 U.S.C. 154(b) by 435 days.

(21) Appl. No.: 15/973,351

(22) Filed: May 7, 2018

(65) Prior Publication Data

US 2019/0336026 A1 Nov. 7, 2019

(51) Int. Cl.
*A61B 5/316* (2021.01)
*A61B 5/00* (2006.01)
(Continued)

(52) U.S. Cl.
CPC ............. *A61B 5/316* (2021.01); *A61B 5/283* (2021.01); *A61B 5/352* (2021.01); *A61B 5/361* (2021.01);
(Continued)

(58) Field of Classification Search
CPC .... A61B 5/04012; A61B 5/042; A61B 5/0456
(Continued)

(56) References Cited

U.S. PATENT DOCUMENTS 3,946,744 A 3/1976 Auerbach
5,713,367 A 2/1998 Arnold et al.
(Continued)

OTHER PUBLICATIONS

Extended European Search Report for European Patent Application No. 19172674.4, dated Oct. 4, 2019 (8 pages).
(Continued)

*Primary Examiner* — Nadia A Mahmood
(74) *Attorney, Agent, or Firm* — The Small Patent Law Group LLC; Dean D. Small

(57) ABSTRACT

Computer implemented methods and systems for detecting arrhythmias in cardiac activity are provided. The method is under control of one or more processors configured with specific executable instructions. The method obtains a far field cardiac activity (CA) data set that includes far field CA signals for beats. The method applies a feature enhancement function to the CA signals to form an enhanced feature in the CA data set. The method calculates an adaptive sensitivity level and sensitivity limit based on the enhanced feature from one or more beats within the CA data set and automatically iteratively analyzes a beat segment of interest by comparing the beat segment of interest to the current sensitivity level to determine whether one or more R-waves are present within the beat segment of interest. The method repeats the iterative analyzing operation while progressively adjusting the current sensitivity level until i) the one or more R-waves are detected in the beat segment of interest and/or ii) the current sensitivity level reaches the sensitivity limit. The method detects an arrhythmia within the beat segment of interest based on a presence or absence of the one or more R-waves and records results of the detecting of the arrhythmia.

28 Claims, 25 Drawing Sheets

(51) Int. Cl.
*A61B 5/283* (2021.01)
*A61B 5/352* (2021.01)
*A61B 5/361* (2021.01)
*A61B 5/363* (2021.01)
*A61B 5/366* (2021.01)

(52) U.S. Cl.
CPC .............. *A61B 5/363* (2021.01); *A61B 5/366* (2021.01); *A61B 5/7203* (2013.01)

(58) Field of Classification Search
USPC ......................................................... 607/517
See application file for complete search history.

(56) References Cited

U.S. PATENT DOCUMENTS

| | | | |
|---|---|---|---|
| 7,248,921 B2 | 7/2007 | Palreddy et al. | |
| 7,294,108 B1 | 11/2007 | Bornzin et al. | |
| 7,894,894 B2 | 2/2011 | Stadler et al. | |
| 8,135,456 B2 | 3/2012 | Haluska | |
| 8,260,404 B1 | 9/2012 | Bharmi | |
| 8,332,022 B2 | 12/2012 | Brown et al. | |
| 8,391,980 B2 | 3/2013 | Bornzin et al. | |
| 8,831,713 B2 | 9/2014 | Stadler et al. | |
| 8,831,747 B1 | 9/2014 | Min et al. | |
| 9,044,610 B2 | 6/2015 | Rosenberg et al. | |
| 9,174,062 B2 | 11/2015 | Stadler et al. | |
| 9,216,285 B1 | 12/2015 | Boling et al. | |
| 9,232,485 B2 | 1/2016 | Wu et al. | |
| 9,333,351 B2 | 5/2016 | Arnold et al. | |
| 9,486,155 B2 | 11/2016 | Sarkar et al. | |
| 2006/0235476 A1 | 10/2006 | Gunderson | |
| 2007/0232948 A1* | 10/2007 | Stadler ................ | A61B 5/7239 600/512 |
| 2008/0082014 A1 | 4/2008 | Cao | |
| 2009/0270749 A1 | 10/2009 | Haluska | |
| 2009/0281587 A1 | 11/2009 | Pei | |
| 2012/0029373 A1 | 2/2012 | Stadler et al. | |
| 2013/0138005 A1 | 5/2013 | Dong et al. | |
| 2015/0038863 A1 | 2/2015 | Schotten et al. | |
| 2016/0213270 A1 | 7/2016 | Cao | |
| 2017/0251940 A1 | 9/2017 | Perschbacher et al. | |
| 2017/0273589 A1 | 9/2017 | Sarkar | |
| 2018/0064360 A1 | 3/2018 | Siejko et al. | |

OTHER PUBLICATIONS

Extended European Search Report for corresponding EP Application No. 19172674.4 dated Oct. 4, 2019 (8 pages).
Extended European Search Report for corresponding EP Application No. 19172673.6 dated Jul. 15, 2019 (5 pages).

\* cited by examiner

METHOD AND SYSTEM TO DETECT R-WAVES IN CARDIAC ARRHYTHMIC PATTERNS

FIELD OF THE INVENTION

Embodiments herein relate generally to implantable medical devices, and more particularly to detection and discrimination of arrhythmic patterns of interest.

RELATED APPLICATIONS

The following applications relate to and are filed concurrently on the same day as the present application, and are expressly incorporated herein by reference in their entireties (hereafter referred to as "Co-Pending Related Applications"):

U.S. patent application Ser. No. 15/973,126, titled "METHOD AND SYSTEM FOR SECOND PASS CONFIRMATION OF DETECTED CARDIAC ARRHYTHMIC PATTERNS" (now U.S. Pat. No. 10,729,346, issued 4 Aug. 2020), U.S. patent application Ser. No. 15/973,107, titled "METHOD AND SYSTEM TO DETECT P-WAVES IN CARDIAC ARRHYTHMIC PATTERNS" (now U.S. Pat. No. 10,856,761, issued 8 Dec. 2020), U.S. patent application Ser. No. 15/973,307, titled "METHOD AND SYSTEM TO DETECT POST VENTRICULAR CONTRACTIONS IN CARDIAC ARRHYTHMIC PATTERNS" (now U.S. Pat. No. 10,874,322, issued 29 Dec. 2020), and U.S. patent application Ser. No. 15/973,384, titled "METHOD AND SYSTEM TO DETECT NOISE IN CARDIAC ARRHYTHMIC PATTERNS".

BACKGROUND OF THE INVENTION

Atrial fibrillation (AF) is a common and serious cardiac arrhythmia, affecting more than two million people in the United States alone. Clinically, atrial fibrillation involves an abnormality of electrical impulse formation and conduction that originates in the atria. Atrial fibrillation is characterized by multiple swirling wavelets of electrical current spreading across the atria in a disorganized manner. The irregularity of electrical conduction throughout the atria creates irregular impulse propagation through the atrioventricular (AV) node into the ventricle.

Impulse propagation through the AV node may be extremely rapid, leading to reduced diastolic filling of the heart chambers and a corresponding reduction of the cardiac pumping action. Increased heart rate and loss of AV synchrony may also exacerbate any underlying heart problems, such as heart failure, coronary blood flow, or other pulmonary disorders. Alternatively, impulse propagation through the AV node may be very limited due to AV node refractoriness so that atrial fibrillation can be sustained indefinitely, as the ventricles continue to drive circulation, albeit inefficiently.

Atrial Fibrillation (AF) monitoring systems have been developed for use in an ambulatory setting, which may be either external, such as a Holter monitor, or internal, such as implantable cardiac monitors or "loop recorders". These systems continually sense cardiac electrical signals from a patient's heart, process the signals to detect arrhythmias and upon detection, record the electrical signals for subsequent review and analysis.

More recently, interest has increased in providing improved implantable cardiac monitors. It has been proposed that implantable cardiac monitors may be used for diagnosis of re-current AF after AF ablation, cryptogenic stroke, and other arrhythmias. Further, there is an interest in improved management of arrhythmia episodes in connection with medication usage, as well as monitoring AF in connection with periodic atrial cardioversion.

Algorithms used by existing monitoring systems for detecting AF are primarily based on an irregularity of R-R intervals. However, these algorithms may provide false positive AF detections when AF did not necessarily exist. As one example, certain AF detection algorithms may be confused when a patient exhibits sinus rhythm with irregular R-R intervals.

Further, existing AF detection algorithms may experience undue false positives in connection with frequent premature ventricular contraction (PVC). Existing AF algorithms may not exhibit sufficient positive predictive value (PPV) of AF episode detection and duration (burden).

An opportunity remains to improve the accuracy of signal markers that are sensed and utilized for generating accurate diagnostics and for computing short/long term trends in physiological signals leading to actionable insights and predictions. Although recent improvements have been made in implantable device hardware, filters, and sensing algorithms, false detection of bradycardia and asystole episodes remains a challenge due to small amplitude signals, premature ventricular contraction (PVC) beats, sudden drops in signal amplitude, suboptimal device programming, and loss of contact between subcutaneous tissue and electrodes. Improved sensing algorithm performance could lead to reduced unnecessary data transmission to remote clinicians, episode review burden, and potentially prolong implantable cardiac monitor (ICM) longevity.

SUMMARY

In accordance with embodiments herein, a computer implemented method for detecting arrhythmias in cardiac activity is provided. The method is under control of one or more processors configured with specific executable instructions. The method obtains a far field cardiac activity (CA) data set that includes far field CA signals for beats. The method applies a feature enhancement function to the CA signals to form an enhanced feature in the CA data set. The method calculates an adaptive sensitivity level and sensitivity limit based on the enhanced feature from one or more beats within the CA data set and automatically iteratively analyzes a beat segment of interest by comparing the beat segment of interest to the current sensitivity level to determine whether one or more R-waves are present within the beat segment of interest. The method repeats the iterative analyzing operation while progressively adjusting the current sensitivity level until i) the one or more R-waves are detected in the beat segment of interest and/or ii) the current sensitivity level reaches the sensitivity limit. The method detects an arrhythmia within the beat segment of interest based on a presence or absence of the one or more R-waves and records results of the detecting of the arrhythmia.

Optionally, the applying, calculating and automatically iteratively analyzing operations may be performed as a second pass confirmation for an arrhythmia episode declared by a first pass arrhythmia detection algorithm implemented by an implantable device. The CA data set may include device documented markers in combination with the CA signals. The CA data set may be generated by the implantable device in connection with the first pass arrhythmia detection algorithm. The first pass arrhythmia detection algorithm may declare the arrhythmia episode to be one of a bradycardia, tachycardia, asystole or atrial fibrillation episode. The calculating the adaptive sensitivity level may further comprise determining amplitudes for one or more features of the beat segment of interest. The adaptive sensitivity level may be based on the amplitudes. The comparing operation may include determining whether at least a portion of the beat segment of interest exceed the current sensitivity level.

Optionally, the adaptive sensitivity level may be determined based on a comparison of an ensemble R-wave peak, ensemble T-wave peak and ensemble P-wave peak amplitudes and/or variability that represent amplitudes and/or variability for the one or more features. The analyzing operation may comprise analyzing the beat segment of interest iteratively while adjusting the adaptive sensitivity level to increase resolution during each iterative analysis until reaching the sensitivity limit or specific exiting criteria. The method may further comprise confirming or denying at least one of a bradycardia episode based on a number of X beats within a bradycardia zone out of a total of Y beats within the CA data set. The method may further comprise confirming or denying an asystole episode when the beat segment of interest exhibits no detected electrical activity for a period of time that exceeds an asystole threshold. The applying the feature enhancement function may enhance at least one of an R-wave feature, T-wave feature, P-wave feature and suppresses noise. The feature enhancement function may include applying normalization function and a non-linear scaling function to the CA signals.

In accordance with embodiments herein, a system is provided for detecting arrhythmias in cardiac activity. The system comprises memory to store specific executable instructions. One or more processors are configured to execute the specific executable instructions for obtaining a far field cardiac activity (CA) data set that includes far field CA signals for beats, applying a feature enhancement function to the CA signals to form an enhanced feature in the CA data set, and calculating an adaptive sensitivity level based on the enhanced feature from one or more beats within the CA data set. The memory may automatically iteratively analyzing a beat segment of interest by comparing the beat segment of interest to the current adaptive sensitivity level to determine whether one or more R-waves are present within the beat segment of interest, repeating the iterative analyzing operation while progressively adjusting the adaptive current sensitivity level until i) the one or more R-waves are detected in the beat segment of interest and/or ii) the current sensitivity level reaches the sensitivity limit, detecting an arrhythmia within the beat segment of interest based on a presence or absence of the one or more R-waves and recording results of the detecting of the arrhythmia.

Optionally, the applying, calculating and automatically iteratively analyzing operations may be performed as a second pass confirmation for an arrhythmia episode declared by a first pass arrhythmia detection algorithm implemented by an implantable device. The CA data set may include device documented markers in combination with the CA signals. The CA data set may be generated by the implantable device in connection with the first pass arrhythmia detection algorithm. The first pass arrhythmia detection algorithm may declare the arrhythmia episode to be one of a bradycardia, asystole or atrial fibrillation episode.

Optionally, the processor may be configured to calculate the adaptive sensitivity level by determining amplitudes for one or more features of the beat segment of interest. The sensitivity limit may be based on the amplitudes. The comparing operation may include determining whether at least a portion of the beat segment of interest exceeds the current adaptive sensitivity level. The processor may be configured to determine the adaptive sensitivity level based on a comparison of an ensemble R-wave peak, ensemble T-wave peak and ensemble P-wave peak amplitudes and/or variability that represent amplitudes and/or variability for the one or more features. The processor may be configured to analyze the beat segment of interest iteratively while adjusting the sensitivity level to increase resolution during each iterative analysis until reaching the sensitivity limit or specific exiting criteria.

Optionally, the processor may be further configured to confirm or deny at least one of a bradycardia episode based on a number of X beats within a bradycardia zone out of a total of Y beats within the CA data set. The processor may be further configured to confirm or deny an asystole episode when the beat segment of interest exhibits no detected electrical activity for a period of time that exceeds an asystole threshold. The processor may be configured to apply the feature enhancement function to enhance at least one of an R-wave feature, T-wave feature, and/or P-wave feature and suppresses noise. The processor may be configured to apply normalization function and a non-linear scaling function to the CA signals as the feature enhancement function.

In accordance with embodiments herein, a system is provided for detecting arrhythmias in cardiac activity. The system comprises memory to store specific executable instructions. One or more processors are configured to execute the specific executable instructions for obtaining a far field cardiac activity (CA) data set that includes far field CA signals for beats, identifying a T-wave characteristic of interest (COI) and an R-wave COI from the CA signals and adjusting profile parameters of a sensitivity profile based on the T-wave COI and R-wave COI. The sensitivity profile defines a time-varying sensitivity level and a sensitivity limit. The system automatically iteratively analyzes a beat segment of interest by comparing the beat segment of interest to the time-varying sensitivity level to determine whether an R-wave is detected within the beat segment of interest, detecting an arrhythmia within the beat segment of interest based on a presence or absence of the R-wave and recording results of the detecting of the arrhythmia.

Optionally, the processor may be configured to perform the identifying and adjusting operations on a beat by beat basis. The processor may be further configured to identify, in connection with the R-wave COI, a rise rate of a current beat and may determine whether the rise rate of the current beat exceeds a rise rate of a preceding beat by more than a R-wave rise rate threshold. The processor may be further configured to adjust at least one of a start sensitivity parameter that defines a start sensitivity of the sensitivity profile. The processor may be further configured to identify, in connection with the T-wave COI and R-wave COI, at least one of a rapid rise characteristic, a rapid heart rate characteristic, T/R-wave ratio characteristic or a T-wave-to-refractory proximity characteristic.

Optionally, the processor may be further configured to adjust, based on the T-wave COI and R-wave COI, at least one of a refractory period duration, start sensitivity, decay rate, or sensitivity limit parameter. The start sensitivity parameter may define a start sensitivity of the sensitivity profile. The refractory period duration parameter may define a blanking interval. A decay rate parameter may define a slope of a linear time-varying sensitivity level decline. The sensitivity limit parameter may define a lowest sensitivity level that linear sensitivity level decline is not allowed to go below.

In accordance with embodiments herein, a system is provided for detecting arrhythmias in cardiac activity. They system comprises memory to store specific executable instructions. One or more processors are configured to execute the specific executable instructions for obtaining a far field cardiac activity (CA) data set that includes far field CA signals for a series of beats, applying an initial R-wave detection process to the CA signals and designating R-wave markers in the CA data set. The R-wave markers are separated by RR intervals. The system applies an R-wave confirmation process that comprises calculating instantaneous and average RR intervals between the R-wave markers designated by the initial R-wave detection process, identifying a suspect beat segment from the CA signals based on a relation between the instantaneous and average RR intervals, searching the suspect beat segment for a potential under detected beat by comparing the suspect beat segment to one or more QRS templates and when an under detected beat is identified from the suspect beat segment, designating a new R-wave marker within the CA data set corresponding to the under detected beat. The system detects an arrhythmia within CA data set based on the R-wave markers designated during the initial R-wave detection process and R-wave confirmation process and records results of the detecting of the arrhythmia.

Optionally, the processor may be further configured to analyze the relation between the instantaneous and average RR intervals. The instantaneous and average RR intervals are identified by stepping through successive beat segments along the CA signal to search for potential under detected beats. The instantaneous RR interval may represent an interval between a current R-wave marker and one of a preceding and succeeding R-wave marker. The average RR interval may represent an average interval for a predetermined number of RR intervals related to a current RR interval. The relation utilized to identify the suspect beat segment may represent a difference between the instantaneous and average RR intervals that exceeds an RR interval range threshold.

Optionally, the processor may be further configured to apply a feature enhancement to the CA signals to form enhanced R-wave or T-wave features in the CA data set. The processor may be further configured to identify the suspect beat segment by overlaying a search window on a current beat segment and comparing i) the instantaneous RR interval for a current beat within the search window and ii) the average RR interval corresponding to a collection of beats within the search window. The comparison may be performed while iteratively stepping the search window through the CA signals beat by beat. The processor may be further configured to build a library of QRS templates based on morphologies of beats detected in the CA signals, identify a current QRS segment from the CA signals, compare the current QRS segment to the library of QRS templates and when the current QRS segment does not match the QRS templates, add a new QRS template to the library based on the current QRS segment.

DETAILED DESCRIPTION

Figure 1:
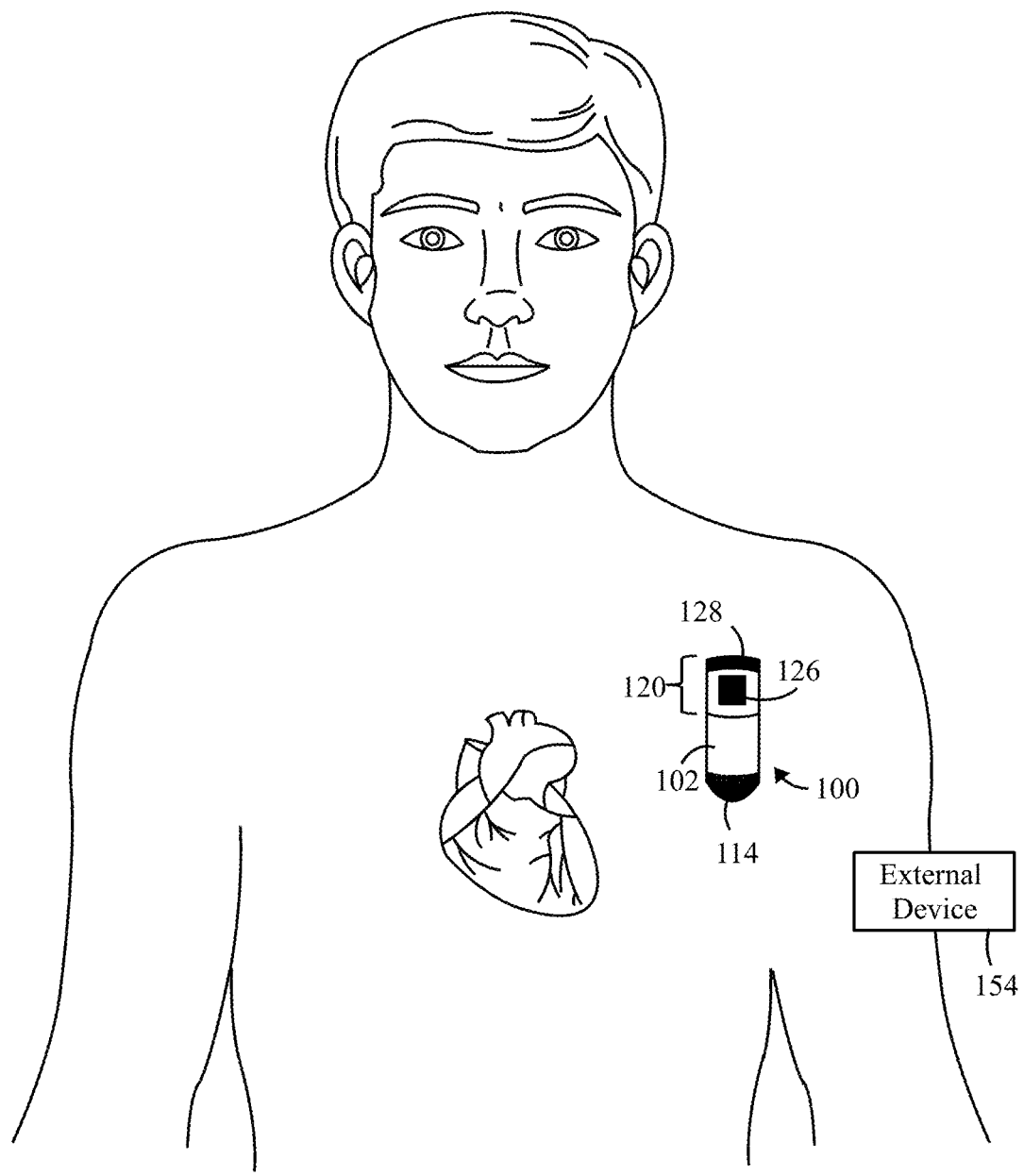
FIG. 1 illustrates an implantable cardiac monitoring device (ICM) intended for subcutaneous implantation at a site near the heart in accordance with embodiments herein.

I. TERMS AND ABBREVIATIONS
II. OVERVIEW—$1^{ST}$ & $2^{ND}$ PASS AF DETECTION/CONFIRMATION SYSTEM & PROCESS
III. ALTERNATIVE EMBODIMENT—IMPROVED R-WAVE DETECTION ALGORITHM—BRADYCARDIA AND ASYSTOLE EPISODES USING A SECOND PASS DETECTION WORKFLOW
IV. ALTERNATIVE EMBODIMENT—R-WAVE DETECTION USING SELF-ADJUSTING PARAMETERS AND PHYSIOLOGIC DISCRIMINATORS ($1^{ST}$ & $2^{ND}$ PASS)
V. ALTERNATIVE EMBODIMENT—FULLY ADAPTIVE R-WAVE DETECTION/CORRECTION ALGORITHM ($1^{ST}$ & $2^{ND}$ PASS)
VI. ALTERNATIVE EMBODIMENT—NOISE DETECTION ALGORITHM FOR CA SIGNALS SENSED BY IMPLANTABLE CARDIAC MONITOR ($1^{ST}$ & $2^{ND}$ PASS)

I. Terms and Abbreviations

The terms "cardiac activity signal", "cardiac activity signals", "CA signal" and "CA signals" (collectively "CA signals") are used interchangeably throughout to refer to an analog or digital electrical signal recorded by two or more electrodes positioned subcutaneous or cutaneous, where the electrical signals are indicative of cardiac electrical activity. The cardiac activity may be normal/healthy or abnormal/arrhythmic. Non-limiting examples of CA signals include ECG signals collected by cutaneous electrodes, and EGM signals collected by subcutaneous electrodes.

The terms "cardiac activity data set" and "CA data set" (collectively "CA data set") are used interchangeably to refer to a data set that includes measured CA signals for a series of cardiac events in combination with device documented markers.

The term "marker" refers to data and/or information identified from CA signals that may be presented as graphical and/or numeric indicia indicative of one or more features within the CA signals and/or indicative of one or more episodes exhibited by the cardiac events. Markers may be superimposed upon CA signals or presented proximate to, and temporally aligned with, CA signals. Non-limiting examples of markers may include R-wave markers, noise markers, activity markers, interval markers, refractory markers, P-wave markers, T-wave markers, PVC markers, sinus rhythm markers, AF markers and other arrhythmia markers. As a further non-limiting example, basic event markers may include "AF entry" to indicate a beginning of an AF event, "in AF" to indicate that AF is ongoing, "AF exit" to indicate that AF has terminated, "T" to indicate a tachycardia beat, "B" to indicate a bradycardia beat, "A" to indicate an asystole beat, "VS" to indicate a regular sinus beat, "Tachy" to indicate a tachycardia episode, "Brady" to indicate a Bradycardia episode, "Asystole" to indicate an asystole episode, "Patient activated" to indicate a patient activated episode. An activity marker may indicate activity detected by activity sensor during the CA signal. Noise markers may indicate entry/start, ongoing, recovery and exit/stop of noise. Markers may be presented as symbols, dashed lines, numeric values, thickened portions of a waveform, and the like. Markers may represent events, intervals, refractory periods, ICM activity, and other algorithm related activity. For example, interval markers, such as the R-R interval, may include a numeric value indicating the duration of the interval. The AF markers indicate atrial fibrillation rhythmic.

The term "device documented marker" refers to markers that are declared by an implantable cardiac monitor and/or implantable medical device. Any or all of the foregoing examples of markers represent device document markers. Markers may be declared based on numerous criteria, such as signal processing, feature detection and AF detection software and hardware within and/or operating on the implantable cardiac monitor and/or implantable medical device.

The term "COI" refers to a characteristic of interest within CA signals. Non-limiting examples of features of interest include an R-wave, P-wave, T-wave and isoelectric segments. A feature of interest may correspond to a peak of an individual R-wave, an average or median P, R or T-wave peak and the like.

The terms "beat" and "cardiac event" are used interchangeably and refer to both normal or abnormal events.

The terms "normal" and "sinus" are used to refer to events, features, and characteristics of, or appropriate to, a heart's healthy or normal functioning.

The terms "abnormal," or "arrhythmic" are used to refer to events, features, and characteristics of, or appropriate to, a un-healthy or abnormal functioning of the heart.

The term "real-time" refers to a time frame contemporaneous with a normal or abnormal episode occurrences. For example, a real-time process or operation would occur during or immediately after (e.g., within minutes or seconds after) a cardiac event, a series of cardiac events, an arrhythmia episode, and the like.

The term "adaptive", as used in connection with a sensitivity profile, sensitivity limit, sensitivity level or other sensing parameters, refers to an ability of the processes herein to modify the value of sensitivity and/or sensing parameters based on features within the CA signals. The sensitivity profile parameters may include refractory period, start sensitivity, decay delay, sensitivity limit, slope of sensitivity decay, etc.

The term "sensitivity level", as used herein, refers to a threshold that an input CA signal must exceed for an implantable device to identify a CA signal feature of interest (e.g., an R-wave). As one non-limiting example, software may be implemented using a programmed sensitivity level to declare an R-wave to be detected when the input CA signal exceeds the current programmed sensitivity level In response, the software declares a device documented feature (e.g., R-wave) marker. The sensitivity level may be defined in various manners based on the nature of the CA signals. For example, when the CA signals measure electrical activity in terms of millivolts, the sensitivity level represents a millivolt threshold. For example, when a cardiac beat with a 0.14 mV amplitude is sensed by a device hardware, and R-wave may be detected when the current sensitivity level is programmed to 0.1 mV. However, when the sensitivity level is programmed to 0.15 mV or above, a cardiac beat with amplitude of 0.14 mV will not be detected as an R-wave. Embodiments herein determine an adaptive sensitivity limit and sensitivity profile for the sensitivity level.

The term "turn", as used herein to refer to characteristics of a shape or morphology of a CA signal, shall mean changes in a direction of the CA signal. For example, the CA signal may turn by changing direction from a signal having a positive slope to a negative slope, or from a signal having a negative slope to a positive slope. Turns may have various associated characteristics such as amplitude, frequency (e.g., number of turns per unit time) and duration (e.g., an amount of time for the signal to exceed and drop below a desired percentage of the signal peak).

The terms "significant" and "non-significant", when used in connection with describing PVC burden, refer to an amount of PVC burden that is, or is not, sufficient to cause an AF detection algorithm to declare a false arrhythmia episode. A small number of PVC events, and/or a collection of PVC events that are spaced substantially apart from one another over time, may not be sufficient to be considered "significant" as the PVC events do not cause the AF detection algorithm to declare a false arrhythmia episode. Alternatively, when a sufficient number of PVC events occur within a relatively short period of time, the potential exists that the AF detection algorithm incorrectly identifies R-waves within the PVC events, leading to a declaration of a false arrhythmia episode. For example, a 30-45 second strip of EGM signals may include one or more PVC events that cause the AF detection algorithm of an IMD to designate a false R-wave marker. Based on the number of false R-wave markers in the EGM strip, the AF detection algorithm may determine that no arrhythmia episode is present or a false arrhythmia episode is present.

II. Overview—1$^{st}$ & 2$^{nd}$ Pass AF Detection/Confirmation System & Process FIG. 1 illustrates an implantable cardiac monitoring device (ICM) 100 intended for subcutaneous implantation at a site near the heart. The ICM 100 includes a pair of spaced-apart sense electrodes 114, 126 positioned with respect to a housing 102. The sense electrodes 114, 126 provide for detection of far field electrogram signals. Numerous configurations of electrode arrangements are possible. For example, the electrode 114 may be located on a distal end of the ICM 100, while the electrode 126 is located on a proximal side of the ICM 100. Additionally or alternatively, electrodes 126 may be located on opposite sides of the ICM 100, opposite ends or elsewhere. The distal electrode 114 may be formed as part of the housing 102, for example, by coating all but a portion of the housing with a nonconductive material such that the uncoated portion forms the electrode 114. In this case, the electrode 126 may be electrically isolated from the housing 102 electrode by placing it on a component separate from the housing 102, such as the header 120. Optionally, the header 120 may be formed as an integral portion of the housing 102. The header 120 includes an antenna 128 and the electrode 126. The antenna 128 is configured to wirelessly communicate with an external device 154 in accordance with one or more predetermined wireless protocols (e.g., Bluetooth, Bluetooth low energy, Wi-Fi, etc.). The housing 102 includes various other components such as: sense electronics for receiving signals from the electrodes, a microprocessor for processing the signals in accordance with algorithms, such as the AF detection algorithm described herein, a loop memory for temporary storage of CA data, a device memory for long-term storage of CA data upon certain triggering events, such as AF detection, sensors for detecting patient activity and a battery for powering components.

In at least some embodiments, the ICM 100 is configured to be placed subcutaneously utilizing a minimally invasive approach. Subcutaneous electrodes are provided on the housing 102 to simplify the implant procedure and eliminate a need for a transvenous lead system. The sensing electrodes may be located on opposite sides of the device and designed to provide robust episode detection through consistent contact at a sensor—tissue interface. The ICM 100 may be configured to be activated by the patient or automatically activated, in connection with recording subcutaneous ECG signals.

The ICM 100 senses far field, subcutaneous CA signals, processes the CA signals to detect arrhythmias and if an arrhythmia is detected, automatically records the CA signals in memory for subsequent transmission to an external device 154. The CA signal processing and AF detection is provided for, at least in part, by algorithms embodied in or implemented by the microprocessor. The ICM 100 includes one or more processors and memory that stores program instructions directing the processors to implement AF detection utilizing an on-board R-R interval irregularity (ORI) process that analyzes cardiac activity signals collected over one or more sensing channels.

Figure 2A:
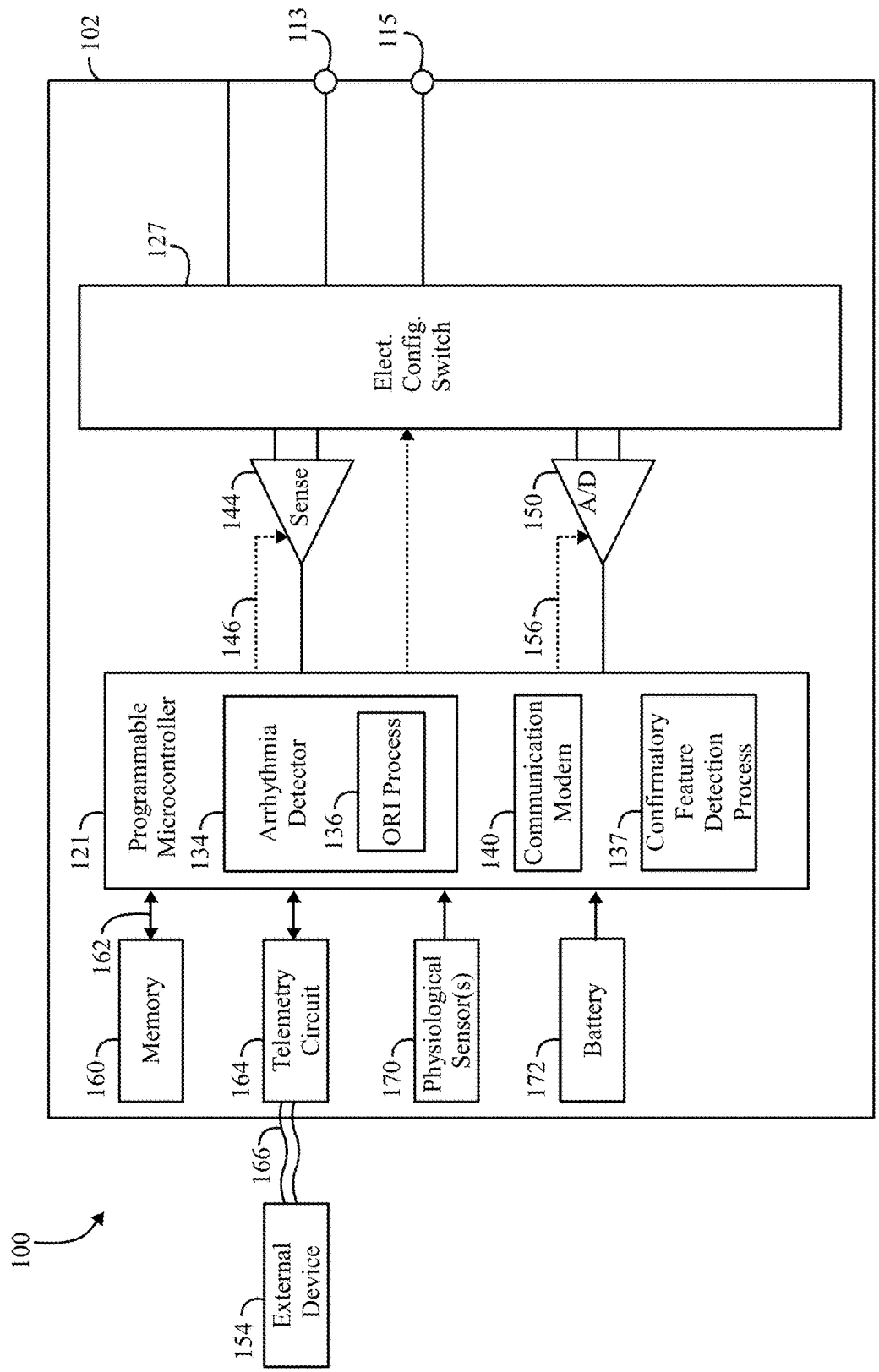
FIG. 2A shows a block diagram of the ICM formed in accordance with embodiments herein.

FIG. 2A shows a block diagram of the ICM 100 formed in accordance with embodiments herein. The ICM 100 may be implemented to monitor ventricular activity alone, or both ventricular and atrial activity through sensing circuitry. The ICM 100 has a housing 102 to hold the electronic/computing components. The housing 102 (which is often referred to as the "can", "case", "encasing", or "case electrode") may be programmably selected to act as an electrode for certain sensing modes. Housing 102 further includes a connector (not shown) with at least one terminal 113 and optionally additional terminals 115. The terminals 113, 115 may be coupled to sensing electrodes that are provided upon or immediately adjacent the housing 102. Optionally, more than two terminals 113, 115 may be provided in order to support more than two sensing electrodes, such as for a bipolar sensing scheme that uses the housing 102 as a reference electrode. Additionally or alternatively, the terminals 113, 115 may be connected to one or more leads having one or more electrodes provided thereon, where the electrodes are located in various locations about the heart. The type and location of each electrode may vary.

The ICM 100 includes a programmable microcontroller 121 that controls various operations of the ICM 100, including cardiac monitoring. Microcontroller 121 includes a microprocessor (or equivalent control circuitry), RAM and/or ROM memory, logic and timing circuitry, state machine circuitry, and I/O circuitry. The microcontroller 121 also performs the operations described herein in connection with collecting cardiac activity data and analyzing the cardiac activity data to identify AF episodes.

A switch 127 is optionally provided to allow selection of different electrode configurations under the control of the microcontroller 121. The electrode configuration switch 127 may include multiple switches for connecting the desired electrodes to the appropriate I/O circuits, thereby facilitating electrode programmability. The switch 127 is controlled by a control signal from the microcontroller 121. Optionally, the switch 127 may be omitted and the I/O circuits directly connected to the housing electrode 114 and a second electrode 126. Microcontroller 121 includes an arrhythmia detector 134 that is configured to analyze cardiac activity signals to identify potential AF episodes as well as other arrhythmias (e.g., Tachcardias, Bradycardias, Asystole, etc.). By way of example, the arrhythmia detector 134 may implement an AF detection algorithm as described in U.S. Pat. No. 8,135,456, the complete subject matter of which is incorporated herein by reference. Although not shown, the microcontroller 121 may further include other dedicated circuitry and/or firmware/software components that assist in monitoring various conditions of the patient's heart and managing pacing therapies.

The ICM 100 is further equipped with a communication modem (modulator/demodulator) 140 to enable wireless communication. In one implementation, the communication modem 140 uses high frequency modulation, for example using RF, Bluetooth or Bluetooth Low Energy telemetry protocols. The signals are transmitted in a high frequency range and will travel through the body tissue in fluids without stimulating the heart or being felt by the patient. The communication modem 140 may be implemented in hardware as part of the microcontroller 121, or as software/firmware instructions programmed into and executed by the microcontroller 121. Alternatively, the modem 140 may reside separately from the microcontroller as a standalone component. The modem 140 facilitates data retrieval from a remote monitoring network. The modem 140 enables timely and accurate data transfer directly from the patient to an electronic device utilized by a physician.

The ICM 100 includes sensing circuitry 144 selectively coupled to one or more electrodes that perform sensing operations, through the switch 127 to detect cardiac activity data indicative of cardiac activity. The sensing circuitry 144 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the features of interest. In one embodiment, switch 127 may be used to determine the sensing polarity of the cardiac signal by selectively closing the appropriate switches.

The output of the sensing circuitry 144 is connected to the microcontroller 121 which, in turn, determines when to store the cardiac activity data of CA signals (digitized by the A/D data acquisition system 150) in the memory 160. For example, the microcontroller 121 may only store the cardiac activity data (from the A/D data acquisition system 150) in the memory 160 when a potential AF episode is detected. The sensing circuitry 144 receives a control signal 146 from the microcontroller 121 for purposes of controlling the gain, threshold, polarization charge removal circuitry (not shown), and the timing of any blocking circuitry (not shown) coupled to the inputs of the sensing circuitry.

In the example of FIG. 2A, a single sensing circuit 144 is illustrated. Optionally, the ICM 100 may include multiple sensing circuits, similar to sensing circuit 144, where each sensing circuit is coupled to two or more electrodes and controlled by the microcontroller 121 to sense electrical activity detected at the corresponding two or more electrodes. The sensing circuit 144 may operate in a unipolar sensing configuration or in a bipolar sensing configuration. Optionally, the sensing circuit 144 may be removed entirely and the microcontroller 121 perform the operations described herein based upon the CA signals from the A/D data acquisition system 150 directly coupled to the electrodes.

The arrhythmia detector 134 of the microcontroller 121 includes an on-board R-R interval irregularity (ORI) process 136 that detects AF episodes using an automatic detection algorithm that monitors for irregular ventricular rhythms that are commonly known to occur during AF. The ORI process 136 may be implemented as firmware, software and/or circuits. The ORI process 136 uses a hidden Markov Chains and Euclidian distance calculations of similarity to assess the transitionary behavior of one R-wave (RR) interval to another and compare the patient's RR interval transitions to the known RR interval transitions during AF and non-AF episodes obtained from the same patient and/or many patients. The ORI process 136 detects AF episodes over a short number of RR intervals. For example, the ORI process 136 may implement the AF detection methods described in U.S. Pat. No. 8,135,456, the complete subject matter of which is incorporated herein by reference in its entirety. As explained herein, the ORI process 136 manages a sensitivity profile of the sensor circuit 144 during R-wave detection utilizing an automatic sensing control (ASC) adjustment to determine whether the CA signal has sufficient amplitude to be analyzed for cardiac events. The ORI process 136 identifies R-waves within the CA signals at points where the CA signal crosses the sensitivity profile (outside of a refractory period). The ORI process 136 tracks RR intervals within the CA signal and identifies AF events within the CA signal based on irregularities in the RR interval. When a sufficient number (e.g., X cardiac events out of Y cardiac events) of the cardiac events within the CA signal are identified as AF events, the ORI process 136 declares an AF episode.

Figure 3:
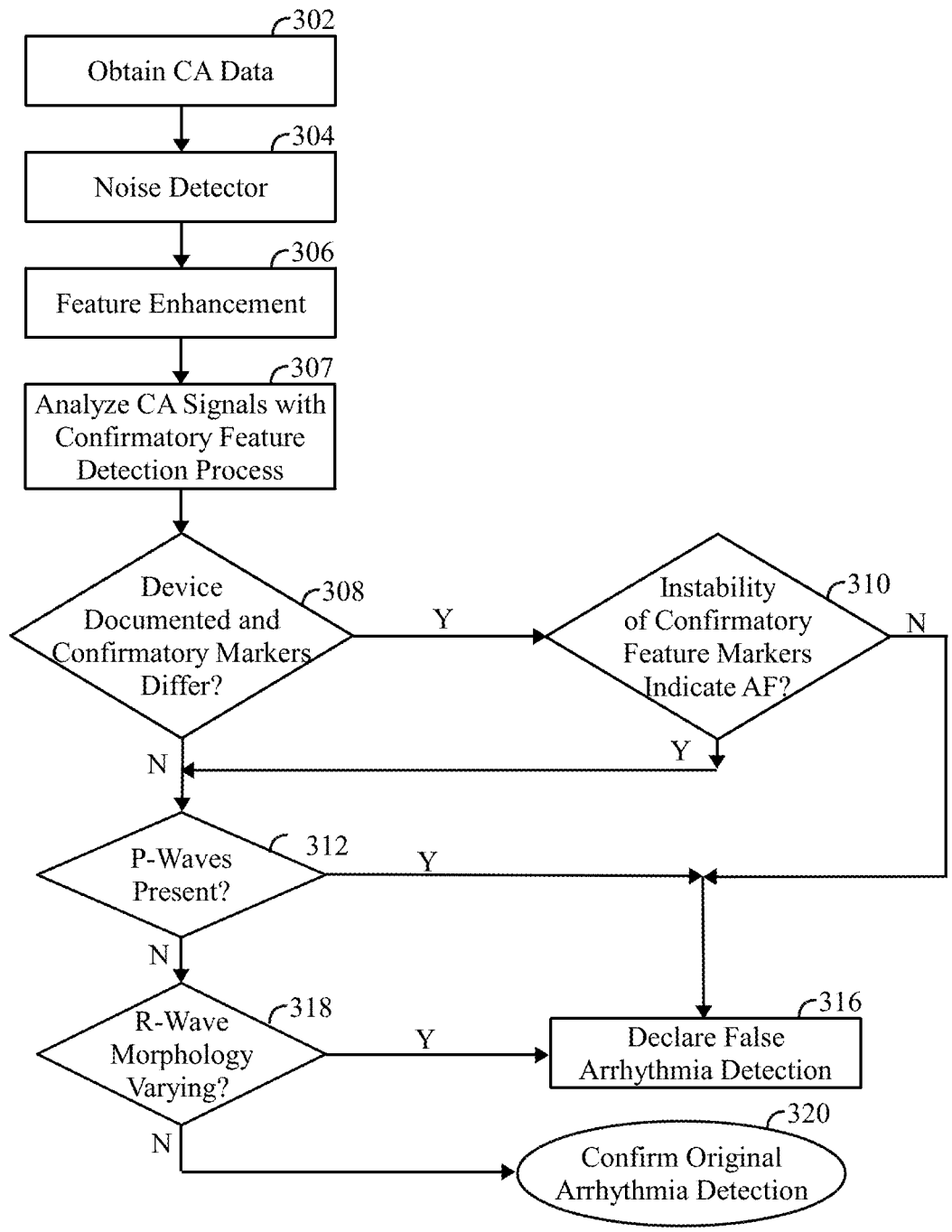
FIG. 3 shows a high-level workflow for an enhanced confirmatory AF detection process implemented in accordance with embodiments herein.
Figure 4:
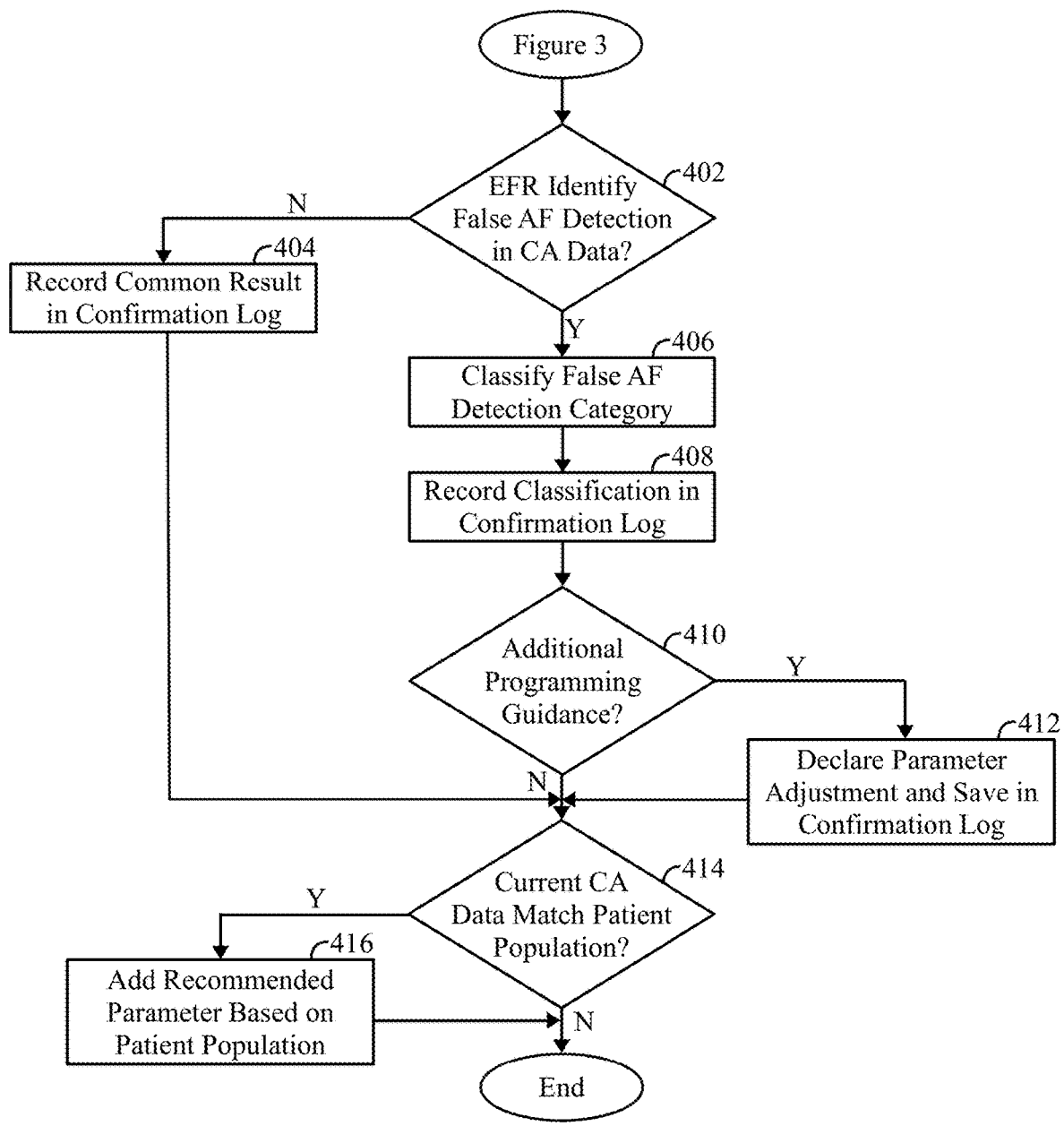
FIG. 4 illustrates a flow chart for classifying AF detection and developing recommendations for sensitivity profile parameter settings in accordance with embodiments herein.

Optionally, the microcontroller 121 may also include a confirmatory feature detection process 137 configured to implement one or more of the operations discussed herein, such as all or a portion of the enhanced confirmatory AF detection process of FIG. 3 and/or all or a portion of the AF detection classifying and recommendation process of FIG. 4. As a further example, the confirmatory feature detection process 137 may implement one or more of the R-wave detection processes, noise detection processes, P-wave detection processes and PVC detection processes described in the Co-Pending Related Applications.

Figure 2B:
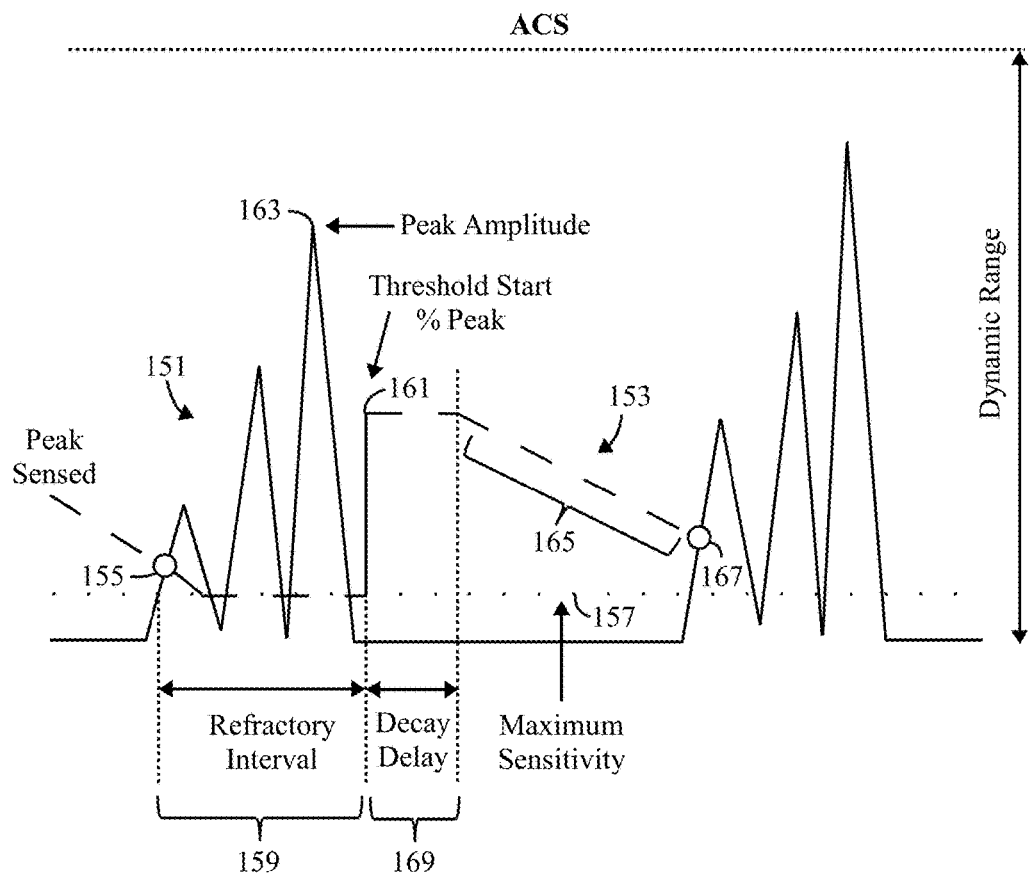
FIG. 2B illustrates an automatic sensing control adjustment utilized by the ORI process of the ICM in accordance with embodiments herein.

FIG. 2B illustrates an automatic sensing control adjustment utilized by the ORI process 136 of the ICM 100 in accordance with embodiments herein. FIG. 2B illustrates an example cardiac activity signal 151 after passing through a rectifier to convert all positive and negative deflections within the cardiac activity signal 151 to be positive deflections. The ORI process 136 manages the sensor circuit 144 to have a sensitivity profile 153 (denoted by a dashed line) that varies over time.

In a basic implementation, the ORI process 136 utilizes a conventional automatic sensing control adjustment based on a conventional sensitivity profile 153. The sensitivity profile 153 is defined by sensitivity profile parameter settings corresponding to the threshold start sensitivity 161, decay delay parameter 169, maximum sensitivity 157 and slope of the sensitivity decay 165. Optionally, the sensitivity decay 165 may be defined in accordance with a non-linear monotonically changing shape from the threshold start sensitivity 161 to the maximum sensitivity 157. The start sensitivity parameter defines a start sensitivity of the sensitivity profile. For example, the start sensitivity parameter may set start sensitivity to a percentage of the preceding R-wave peak amplitude. The refractory period/interval duration parameter defines a blanking interval beginning at a sensed R-wave, during which the processors do not search for a T-wave. The decay delay parameter defines the interval at which the sensitivity profile maintains the sensitivity level at a constant level following expiration of the refractory period before the sensitivity profile begins decreasing. When the sensitivity profile includes a linear sensitivity level decline, the decay delay rate defines a slope of the linear sensitivity level decline. The maximum sensitivity limit defines a lowest sensitivity level (e.g., maximum resolution) that linear sensitivity decline is allowed to reach. The sensitivity parameters are preprogrammed to fixed values and, over the operation of the implantable medical device (IMD), are only modified (if at all) by a clinician.

In accordance with the sensitivity profile 153, when the CA signal 151 crosses the sensitivity profile 153 at starting point 155, the ORI process 136 treats the point 155 as a sensed R-wave and begins a refractory interval 159. No new R-wave (or T-wave) will be sensed during the refractory interval 159. At the end of the refractory interval 159, the sensitivity is adjusted to a threshold start sensitivity 161. The threshold start sensitivity 161 is defined as a percentage of the peak amplitude 163 of the QRS complex of the CA signal 151 detected during the refractory interval 159. The sensing circuit 144 maintains the threshold start sensitivity 161 for a decay delay parameter 169, after which the ORI process 136 begins to monotonically decrease the sensitivity (increase the resolution) of the sensing circuit 144 as denoted by the sensitivity decay 165 within the sensitivity profile 153. The sensing circuit 144 continues to decrease the sensitivity until either the sensitivity decay 165 reaches the maximum sensitivity 157 or an amplitude of the rectified cardiac activity signal 151 exceeds the sensor sensitivity profile 153, such as at a point 167 where a new sensed R wave is detected.

The sensitivity of the sensing circuit 144 (FIG. 2A) is continuously adjusted by the microcontroller 121 in accordance with the sensitivity profile 153 over the course of an individual cardiac event. However, the conventional ORI process does not modify the parameter settings of the sensitivity profile beat by beat or on demand. sensitivity profile parameter In accordance with embodiments herein, the values of the sensitivity parameters may be adjusted based on whether the ORI process 136 is deemed to declare false AF detection R-waves. False AF detection may occur in connection with inappropriate R-wave sensing which may arise from under-sensing of R-waves and/or over-sensing of non-R-waves (e.g., noise, or P-waves, or T-waves as R-waves). For example, the confirmatory feature detection process 137 may determine when the ORI process 136 declares an undesirable number of false AF detections and in response thereto adjust one or more sensitivity profile parameters. Additionally or alternatively, the confirmatory feature detection process may be implemented external to the ICM 100, such as at a local external device or remote server. The local external device and/or remote server may then return, to the ICM 100, adjustments to the sensitivity profile parameters when an externally implemented confirmatory feature detection process identifies an undesirable number of false AF detections.

Returning to FIG. 2A, the ICM 100 further includes an analog-to-digital ND data acquisition system (DAS) 150 coupled to one or more electrodes via the switch 127 to sample cardiac activity signals across any pair of desired electrodes. The data acquisition system 150 is configured to acquire cardiac electrogram (EGM) signals as CA signals, convert the raw analog data into digital data, and store the digital data as CA data for later processing and/or telemetric transmission to an external device 154 (e.g., a programmer, local transceiver, or a diagnostic system analyzer). The data acquisition system 150 is controlled by a control signal 156 from the microcontroller 121. The EGM signals may be utilized as the cardiac activity data that is analyzed for potential AF episodes. The ACS adjustment and ORI process 136 may be applied to signals from the sensor circuit 144 and/or the DAS 150.

By way of example, the external device 154 may represent a bedside monitor installed in a patient's home and utilized to communicate with the ICM 100 while the patient is at home, in bed or asleep. The external device 154 may be a programmer used in the clinic to interrogate the ICM 100, retrieve data and program detection criteria and other features. The external device 154 may be a handheld device (e.g., smartphone, tablet device, laptop computer, smart-watch and the like) that can be coupled over a network (e.g., the Internet) to a remote monitoring service, medical network and the like. The external device 154 facilitates access by physicians to patient data as well as permitting the physician to review real-time CA signals while collected by the ICM 100.

The microcontroller 121 is coupled to a memory 160 by a suitable data/address bus 162. The programmable operating parameters used by the microcontroller 121 are stored in memory 160 and used to customize the operation of the ICM 100 to suit the needs of a particular patient. Such operating parameters define, for example, detection rate thresholds, sensitivity, automatic features, AF detection criteria, activity sensing or other physiological sensors, and electrode polarity, etc.

In addition, the memory 160 stores the cardiac activity data, as well as the markers and other data content associated with detection of arrhythmia episodes. The operating parameters of the ICM 100 may be non-invasively programmed into the memory 160 through a telemetry circuit 164 in telemetric communication via communication link 166 with the external device 154. The telemetry circuit 164 allows intracardiac electrograms and status information relating to the operation of the ICM 100 (as contained in the microcontroller 121 or memory 160) to be sent to the external device 154 through the established communication link 166. In accordance with embodiments herein, the telemetry circuit 164 conveys the cardiac activity data, markers and other information related to AF episodes.

The ICM 100 may further include magnet detection circuitry (not shown), coupled to the microcontroller 121, to detect when a magnet is placed over the unit. A magnet may be used by a clinician to perform various test functions of the housing 102 and/or to signal the microcontroller 121 that the external device 154 is in place to receive or transmit data to the microcontroller 121 through the telemetry circuits 164.

The ICM 100 can further include one or more physiologic sensors 170. Such sensors are commonly referred to (in the pacemaker arts) as "rate-responsive" or "exercise" sensors. The physiological sensor 170 may further be used to detect changes in the physiological condition of the heart, or diurnal changes in activity (e.g., detecting sleep and wake states). Signals generated by the physiological sensors 170 are passed to the microcontroller 121 for analysis and optional storage in the memory 160 in connection with the cardiac activity data, markers, episode information and the like. While shown as being included within the housing 102, the physiologic sensor(s) 170 may be external to the housing 102, yet still be implanted within or carried by the patient. Examples of physiologic sensors might include sensors that, for example, activity, temperature, sense respiration rate, pH of blood, ventricular gradient, activity, position/posture, minute ventilation (MV), and so forth.

A battery 172 provides operating power to all of the components in the ICM 100. The battery 172 is capable of operating at low current drains for long periods of time. The battery 172 also desirably has a predictable discharge characteristic so that elective replacement time can be detected. As one example, the housing 102 employs lithium/silver vanadium oxide batteries. The battery 172 may afford various periods of longevity (e.g., three years or more of device monitoring). In alternate embodiments, the battery 172 could be rechargeable. See for example, U.S. Pat. No. 7,294,108, Cardiac event micro-recorder and method for implanting same, which is hereby incorporated by reference.

The ICM 100 provides a simple to configure data storage option to enable physicians to prioritize data based on individual patient conditions, to capture significant events and reduce risk that unexpected events are missed. The ICM 100 may be programmable for pre- and post-trigger event storage. For example, the ICM 100 may be automatically activated to store 10-120 seconds of CA data prior to an event of interest and/or to store 10-120 seconds of post CA data. Optionally, the ICM 100 may afford patient triggered activation in which pre-event CA data is stored, as well as post event CA data (e.g., pre-event storage of 1-15 minutes and post-event storage of 1-15 minutes). Optionally, the ICM 100 may afford manual (patient triggered) or automatic activation for CA data. Optionally, the ICM 100 may afford additional programming options (e.g., asystole duration, bradycardia rate, tachycardia rate, tachycardia cycle count). The amount of CA data storage may vary based upon the size of the memory 160.

The ICM 100 may provide comprehensive safe diagnostic data reports including a summary of heart rate, in order to assist physicians in diagnosis and treatment of patient conditions. By way of example, reports may include episodal diagnostics for auto trigger events, episode duration, episode count, episode date/time stamp and heart rate histograms. The ICM 100 may be configured to be relatively small (e.g., between 2-10 cc in volume) which may, among other things, reduce risk of infection during implant procedure, afford the use of a small incision, afford the use of a smaller subcutaneous pocket and the like. The small footprint may also reduce implant time and introduce less change in body image for patients.

Figure 2C:
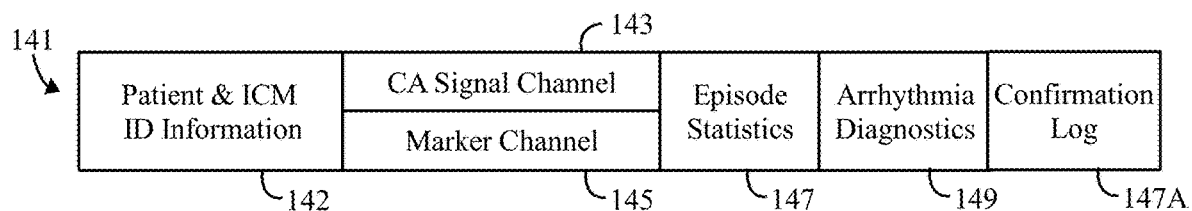
FIG. 2C illustrates cardiac activity data generated and stored by an ICM in accordance with embodiments herein.

FIG. 2C illustrates cardiac activity data generated and stored by the ICM 100 in memory 160 in accordance with embodiments herein. The CA data set 141 is stored by the ICM in response to detection of episodes of interest, patient initiated instructions, physician initiated instructions and the like. The CA data set 141 may include, among other things, patient and ICM identification information 142. By way of example, the patient identification information may include a patient unique medical record number or other identifier, patient name and/or patient demographic information. The ICM ID may include a serial number or other unique identifier of the ICM, software and firmware version numbers, and/or a unique wireless ID. The CA data set 141 includes one or more signal channels 143 that store CA signals collected by a corresponding sensing channel (e.g., sensor circuit 144 or DAS 150). The CA signal channel 143 may include EGM signals for a series of cardiac beats/events sensed by the ICM. The CA data set 141 also includes a marker channel 145 having, among other things, device documented markers identified by the ICM 100 in connection with the CA signal. The device documented markers within the marker channel 145 may include device documented markers indicative of normal sinus features, AF detected events, AF detected episodes and the like. For example, the ORI process 136 (FIG. 2A) utilizes the sensitivity profile 153 (FIG. 2B) to identify R-waves in the CA signal.

The content of the CA signal channel 143 and marker channel 145 may be displayed on a display of an external device (e.g., smart phone, tablet device, computer, smart watch, etc.) as corresponding types of CA and marker waveforms (e.g., in a rhythm display screen). In the present example, a single CA signal channel 143 is described in connection with a single CA signal. Optionally, embodiments herein may be implemented in connection with multiple CA signal channels. For example, the ICM 100 may be configured to include multiple sensing channels with different sensing characteristics. As one example, a first sensing channel may be configured to perform full range signal sensing, such as in connection with detecting R-waves (corresponding to the CA signal channel 143). A second sensing channel may be configured to perform narrow range signal sensing, such as in connection with detecting P-waves which have much smaller amplitude in comparison to the R-waves. Optionally, multiple ECG signals may be displayed in parallel and temporally aligned with EGM and marker waveforms.

The CA data set 141 also includes episode statistics 147 and arrhythmia diagnostics 149. The episode statistics 147 may be presented in a window on a user interface to list various statistical data for any or all episodes recorded by the ICM 100 since the episode and CA data storage were last cleared. Optionally, the episode statistics 147 may also list the number of inhibited VT diagnoses due to arrhythmia qualifiers, such as a bigeminal rhythm qualifier, and/or other rhythm discriminators. As further non-limiting examples, the episode statistics 147 may also include a date of a last programmer session, date of the last ICM interrogation, the date of the presently stored episodes and the date when EGMs were last cleared from the ICM and the like.

Optionally, the CA data set 141 may also include a confirmation log 147A that may be calculated in real-time or off-line in accordance with embodiments herein. For example, the original CA data set 141 may be generated by the ICM based on the ORI process described herein. Once the CA data set 141 is telemetered from the ICM to a local external device and/or remote server, the CA data set 141 is analyzed utilizing a second pass confirmation arrhythmia detection process (e.g., FIGS. 3 and 4). The second pass confirmation detection process generates a confirmation log that includes, among other things, confirmatory markers, confirmatory episode statistics and confirmatory arrhythmia diagnostics that may differ from or be similar to the original episode statistics 147 and arrhythmia diagnostics 149. In certain instances, it may be desirable to return the confirmation log information to the ICM (e.g., FIG. 7). The information from the confirmation log may be telemetered back to the ICM from the local external device and/or remote server. The ICM may then store the confirmation log 147A in connection with a corresponding CA data set.

In the event that an ICM is provided with certain security features that prevent an external device (e.g., cell phone or local monitoring device) from directly changing sensitivity profile parameter settings and/or writing to any or at least certain sections of the memory within the ICM. For example, the security features may prevent an external device from writing over-sensitivity profile parameter settings and/or over the AF statistics and diagnostics that are generated and stored on the ICM. Optionally, as a workaround, the confirmation log may be written to a more flexible section of memory within the ICM (also referred to as an external device accessible section), along with header and/or metadata information tying the confirmation log to a particular portion of the CA data.

Figure 2D:
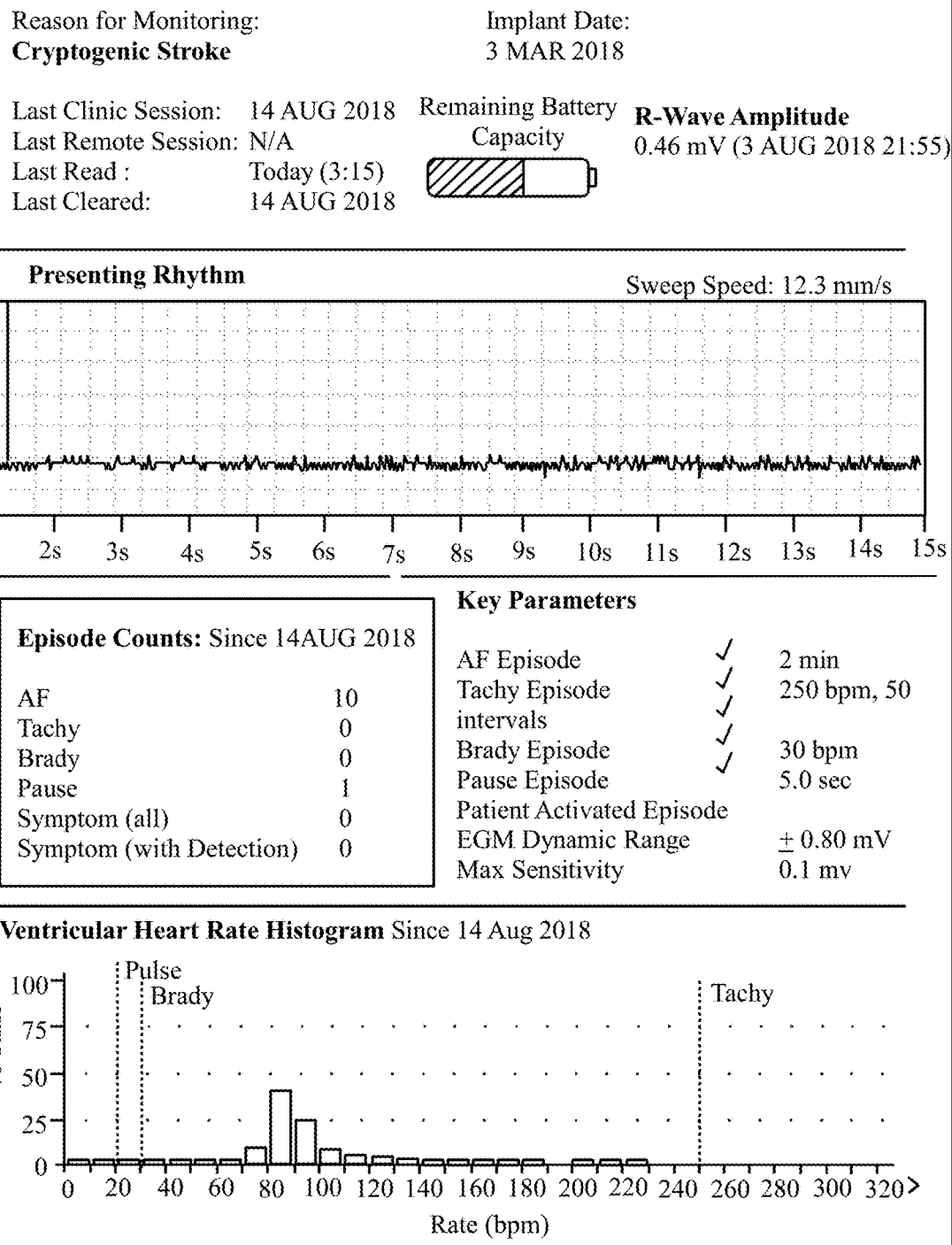
FIG. 2D illustrates screenshots of displays in which episode statistics and arrhythmia diagnostics may be presented to a physician in accordance with an embodiment herein.
Figure 2E:
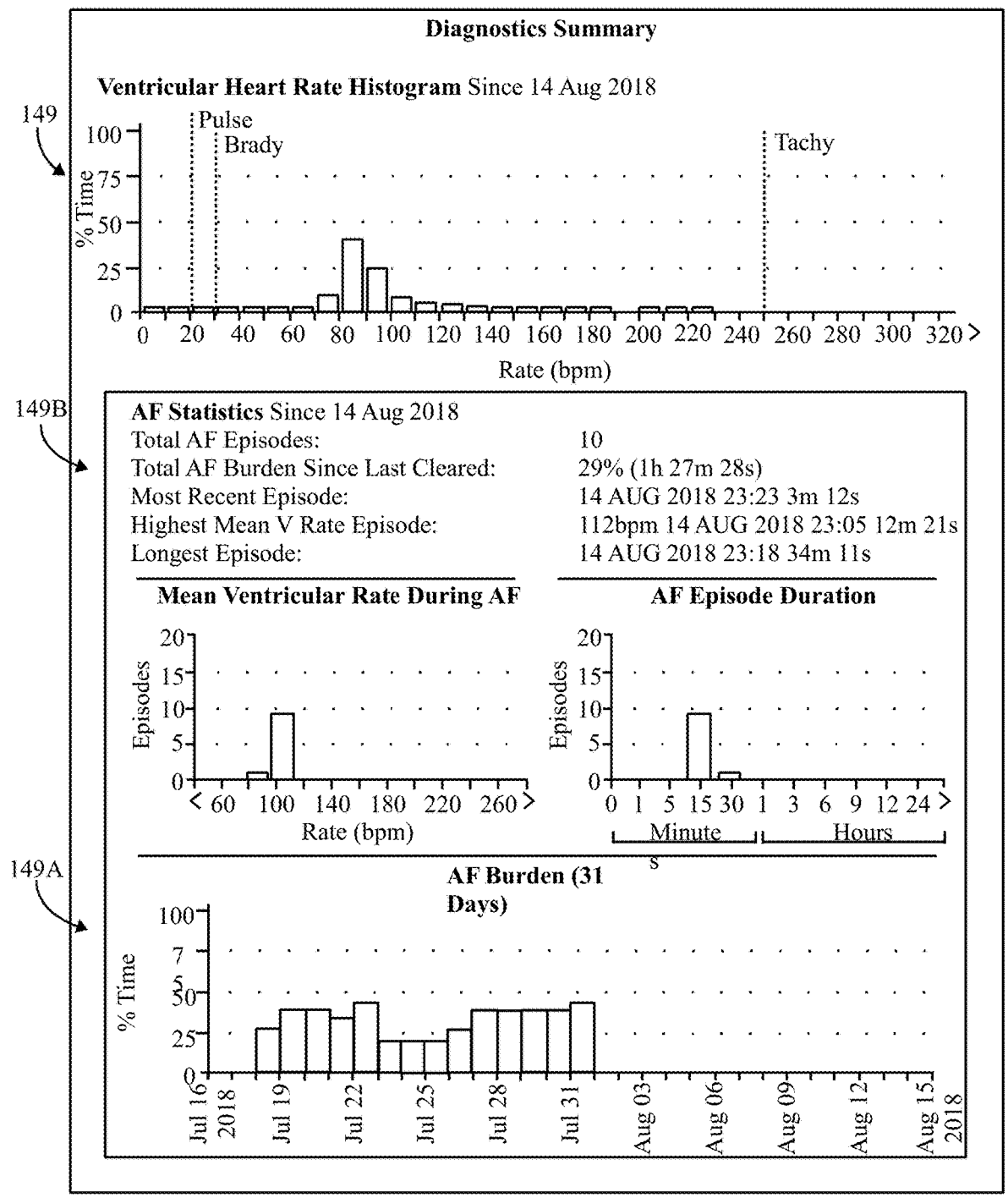
FIG. 2E illustrates screenshots of displays in which episode statistics and arrhythmia diagnostics may be presented to a physician in accordance with an embodiment herein.

FIGS. 2D and 2E illustrate screenshots of displays in which episode statistics and arrhythmia diagnostics may be presented to a physician in accordance with an embodiment herein. The arrhythmia diagnostics 149 may represent cumulative diagnostic information for a period of time, such as when the diagnostics data is last cleared from the ICM. The arrhythmia diagnostics 149 may include various information concerning heart rate, such as ventricular heart rate histograms, dates and times of last programmer sessions, diagnostic data last read, diagnostic data last cleared and the like. The arrhythmia diagnostics 149 may also include AF diagnostics, such as AF burden 149A, AF summaries, AF statistical data 149B, dates and times of last programmer session, last time the AF diagnostic data were read, last time the AF diagnostic data was cleared and the like. By way of example, AF burden may be displayed in an AF diagnostics window of a computing device formatted as one or more bar graphs of a percentage of time (as shown in FIG. 2E) that the patient experienced AF during a predetermined period of time (e.g., each day, each week, each month). The AF burden may show a percentage of time that the patient was in AF since the AF diagnostics data were last cleared. The AF summary may include one or more graphs of mean ventricular heart rate and a duration of AF episodes since the AF diagnostic data were last cleared. The AF diagnostic data may accrue various cumulative totals concerning AF episodes detected and/or stored since the AF diagnostic data were last cleared. The AF statistics may include, among other things, a total number of AF episodes, AF burden trends, AF episode duration histograms, mean ventricular rate during AF and the like.

As explained herein, an enhanced confirmatory AF detection process is implemented to analyze the results of the baseline analysis performed by the ORI process in the ICM. The enhanced confirmatory AF detection process determines whether AF episodes declared by the ICM are true or false, and updates the AF diagnostics in connection there with. Next, various processes are described in connection with embodiments herein that are performed by one or more of the circuits, processors and other structures illustrated in the figures and described in the specification.

FIG. 3 shows a high-level workflow for an enhanced confirmatory AF detection process implemented in accordance with embodiments herein. By way of example, the operations of FIG. 3 may be implemented, as a confirmatory process, where cardiac activity signals have been previously analyzed by an AF detection module, such as the ORI process described in connection with FIGS. 2A and 2B. The process may initiate the operations of FIG. 3 in an attempt to verify whether one or more episodes in a CA data set, are in fact an AF episode or a normal rhythmic/sinus episode. Optionally, the operations of FIG. 3 may be implemented in connection with a CA data set that has not been previously analyzed for potential AF episodes. The operations of FIG. 3 may be implemented as part of a local or distributed system, such as by the microcontroller 121 of the ICM, by a local external device and/or a remote server.

At 302, one or more processors of the system obtain a cardiac activity (CA) data set including CA signals recorded in connection with a series of cardiac events. The CA data includes device documented arrhythmic markers including identifying AF entry and/or exit within the series of cardiac events. The CA data also includes device documented rhythmic markers (e.g., R-wave) to identify the cardiac beats sensed by the device within the series of cardiac events. The CA data also include device documented activity and noise markers to identify periods of time under significant physical activity and/or noise interrupt within the series of cardiac events. All device documented markers are declared and designated by the ICM utilizing the ORI process to analyze the CA signals.

For example, the cardiac activity data may be obtained by an external monitoring device or ICM that includes electrodes that sense CA signals, such as electrocardiogram (ECG) signals and/or intra-electrocardiogram (EGM) signals. The ECG and/or EGM signals may be collected by a subcutaneous ICM that does not include a transvenous lead or otherwise experiences difficulty in sensing P-waves and/or R-waves. The cardiac activity data may have been previously acquired and stored in memory of an implantable or external monitoring device, implantable or external therapy delivery device, programmer, workstation, healthcare network or other system. When the cardiac activity data has been previously acquired, the obtaining operation at 302 represents accessing and reading the previously stored cardiac activity data.

The operations of FIG. 3 may be staged to be performed upon the CA data at various times, such as in real time (e.g., during or shortly after a patient experiences an episode) or at any time after storage of the CA data. The operations of FIG. 3 may be performed by devices and systems at various proximity to a patient with the ICM. For example, the CA data may be read out of an ICM and transmitted to a local portable external device (e.g., smartphone, table computer, laptop computer, smartwatch, etc.), where the local portable external device locally implements all or a portion of the operations described in connection with FIG. 3 while in close proximity to the patient. Additionally or alternatively, the CA data may be read out of the ICM to a local portable external device and transmitted to a remote server, medical network, physician computer and the like, which implements all or a portion of the operations described in connection with FIG. 3 remote from the patient. Additionally or alternatively, the CA data may be read from the ICM by a programmer device, such as during a patient visit to a physician, where the programmer device implements all or a portion of the operations described in connection with FIG. 3 during or after a patient-doctor visit.

The CA data may include CA signals for a series of cardiac events spanning over various periods of time. As one example, one segment or set of the cardiac activity data may be collected for an interval that is 30 seconds to 5 minutes in length and that includes one or more ICM declared AF episodes. As another example, one segment or set of the cardiac activity data may be collected for an interval that begins 10-60 seconds before an episode of interest (e.g., an AF episode) and that ends 10-60 seconds after the episode of interest. A CA data set may include one or multiple AF episodes. The duration of a CA data set may be programmed for a predetermined period of time based on detection of AF episodes and/or based on other criteria. The predetermined period of time may be programmed by a clinician, or automatically updated by one or more processors throughout operation. By way of example, the predetermined period of time may correspond to one minute, 30 minutes, one hour or otherwise. The CA data obtained at 302 may correspond to one detected AF episode and/or multiple detected AF episodes. The CA data set obtained at 302 may correspond to one continuous series of cardiac events (e.g., 1 continuous series for 30 seconds to 5 minutes) and/or separate sets of cardiac events (3-10 separate series, each for 30 seconds to 3 minutes of cardiac events).

Collection and analysis of CA signals by the ICM may be initiated automatically when the ICM detects an episode of interest. Additionally or alternatively, the ICM may collect and analyze CA signals in response to a user-initiated instruction. For example, a user may utilize a smart phone or other portable device to establish a communications session with the ICM and instruct the ICM to begin to collect and analyze cardiac signals, such as when the patient is experiencing discomfort, feeling faint, a rapid heart rate, etc.

At 304 to 320, the one or more processors determine whether the on-board RR interval irregularity process (implemented by the ICM declared one or more false positive AF episodes, such as due to under-sensing or over-sensing features within the CA signal. The operations at 304 to 320 generally perform an R-wave enhancement and feature rejection (EFR) process. The EFR process enlarges or exaggerates features of interest (e.g., R-wave) within the CA signal and optionally suppresses at least certain features not of interest (e.g., non-R-wave features such as noise, T-waves) to obtain confirmatory feature markers. The EFR process applies a series of tests to confirm or reject alternative conditions that a patient may have experienced. The operations at 306 to 320 confirm or reject a presence or absence of certain rhythmic, physiologic and non-physiologic (e.g., noise) features within the CA data. Non-limiting examples of the features, for which the process searches include noise, R-wave changes, P-waves, and post ventricular contractions.

At 304, the one or more processors analyze the CA data for noise and pass or remove segments of the CA signal for select cardiac events based on a noise level within the corresponding segment of the CA signal. The noise is identified based on noise discrimination parameters that are set to a desired sensitivity level. While the sensitivity of the noise detection process at 304 may be adjusted, the sensitivity of the noise detection process at 304 is more selective than the on-board noise detection circuit in the ICM. For example, at 304, the one or more processors may implement the noise detection process described in one or more of the Co-Pending Related Applications referred to above, filed concurrently on the same day as the present application. For example, the operation at 304 generally represents a software based evaluation of the CA data to detect noise. The software based evaluation can be developed in a manner that is tailored to AF detection such that the software-based noise rejection is more sensitive in connection with identifying or removing unduly noisy CA signal segments that in turn give rise to inappropriate R-wave detection, leading to false AF episodes declaration by the ICM. The original CA data processed in connection with FIG. 3 results from the onboard ORI process of the ICM. The onboard ORI process processes incoming signals that have first passed through a hardware-based noise detect that applies noise discrimination the hardware-based noise detector is not as sensitive as, and not as adaptable as, the software based noise discrimination implemented at 304. Also, depending upon a complexity of the software-based noise discrimination, processors of an ICM may not have a sufficient processing power to implement the software noise discrimination. The extent to which the software-based noise discrimination may be implemented on an ICM depends in part upon the sensitivity level desired. For example, the discrimination parameters may be set to a very "conservative" level such that the noise detector only eliminates CA signals for cardiac events that include a substantial amount of noise (e.g., the signal to noise ratio is less than or equal to 50%). Levels for the noise discrimination parameters may be adjusted to eliminate more cardiac events that include relatively intermediate levels of noise (e.g., the signal to noise ratio is between 75% and 90%). The noise discriminator passes CA signals for cardiac events that have less noise than the level defined by the noise discrimination parameters.

Optionally, at 304, when the noise level is sufficiently high (e.g., satisfying a threshold), the initial AF diagnosis/declaration by the ICM may be overridden. For example, when the noise level exceeds a threshold in connection with an AF episode declared by the ICM, the processors may cancel the AF episode declaration and reset any counters set in connection there with. Optionally, as explained below in connection with FIG. 11, embodiments herein may declare a segment of the CA signals to represent a noisy segment, and remove the noisy segment to form noise corrected CA signals. The operations at 306-320 then apply a confirmatory arrhythmia detection process to the noise corrected CA signals. Optionally, when a sufficiently large portion of a CA data set is declared to be noisy, the entire CA data set (e.g., a 30 second EGM strip) may be rejected, and flow returns to 302, where a new CA data set is obtained.

At 306, the one or more processors apply a feature enhancement process to form modified CA signals in which sinus features of interest are enlarged or exaggerated relative to the original/baseline CA signals. Optionally, at least certain features not of interest (e.g., noise, T-waves) are reduced or suppressed relative to the baseline CA signals in order to generate the confirmatory feature (e.g., R-wave) marker. For example, at 306, the one or more processors may implement the feature enhancement process described in one or more of the Co-Pending Related Applications referred to above, filed concurrently on the same day as the present application.

At 307, the one or more processors analyze the modified CA signal utilizing a confirmatory feature detection process. For example, at 306, the one or more processors may implement, as the confirmatory feature detection process, the R-wave detection processes described in one or more of the Co-Pending Related Applications referred to above, and filed concurrently on the same day as the present application. The processors analyze the modified CA signal to identify R-waves, and store a set of confirmatory feature markers separate and distinct from the device documented (DD) feature markers.

At 308, the one or more processors determine whether the confirmatory feature markers match or differ from the DD feature markers. For example, the determination at 308 may be based on a simple count of the number of DD feature markers as compared to a count of the number of confirmatory feature markers. Additionally or alternatively, the determination at 308 may determine whether the confirmatory feature detection process identified confirmatory feature markers (e.g., R-waves) from the CA signals that were not identified by the ORI process or displaced significantly. For example, the DD and confirmatory feature markers for the CA data may be aligned temporally and compared to identify differences.

Differences may occur due to various reasons. For example, the ORI process may under-sense R-waves, while the confirmatory feature detection process properly identifies a feature of interest in the modified CA signal as an R-wave. As another example, the ORI process may over sense R-waves, while the confirmatory feature detection process properly determines that no R-wave is present in a particular segment of the CA signal. Additionally or alternatively, a difference may be declared when the ORI process and confirmatory feature detection process both declare an R-wave for a specific cardiac event, but the DD and confirmatory R-waves are temporally offset from one another in time by more than a desired R-wave offset threshold.

When the process determines at 308 that a difference or change exists between the confirmatory and DD feature markers, flow moves to 310. When the process determines that no difference or change exists between the confirmatory and DD feature markers, flow moves to 312. At 310 the one or more processors identify instability in the confirmatory feature markers. At 310, the one or more processors determine whether the instability within the confirmatory feature marker indicates AF. The processors determine the presence or absence of instability by analyzing variation in the RR intervals between the confirmatory features markers, such as using the processors described in the Co-Pending Related Application and/or the '456 patent. If the instability/variation equals or is below a stability threshold, the segment of the CA signal is considered to exhibit a stable feature-to-feature interval that does not indicate AF. Consequently, flow moves to 316. Alternatively, when the instability is above the instability threshold, the analysis of the CA signal segment is considered to exhibit an unstable feature-to-feature interval. Consequently, flow moves to 312.

At 316, when AF is not indicated, the one or more processors classify an episode in the CA data set to be a DD false positive or false detection. At 316, the one or more processors may perform additional operations, such as setting one or more flags to track the declaration of DD false positives by the ORI process on the ICM. Additionally or alternatively, at 316, the one or more processors may reverse a diagnosis of AF, adjust various statistics tracking the patient's behavior and the like. For example, the AF diagnostics (e.g., 149 in FIG. 2C) may be updated to correct for false AF detection. Additionally or alternatively, a memory segment within the ICM that includes the CA data set associated with a false AF detection may be set to have a lower priority. Reassignment of priority levels to different memory segments may be utilized in connection with overwriting memory segments during future use. For example, when the CA data memory of the ICM approaches or becomes full, the memory segment assigned the lowest priority may then be overwritten first when the ICM detects new AF episodes.

When flow advances to 312, the potential still exists that the CA signals does not include an AF episode. Therefore, the process of FIG. 3 performs additional analysis upon the CA data. At 312, the one or more processors perform a P-wave detection operation to determine whether P-waves are present within the CA signal segment being analyzed. For example, at 312, the one or more processors may implement the P-wave detection process described in one or more of the Co-Pending Related Applications referred to above, and filed concurrently on the same day as the present application. When a P-wave is identified to be present in the CA signal, the process determines that the presence of a P-wave indicates that the current episode is not an AF episode even though RR interval irregularity may be present. Accordingly, flow moves to 316.

Alternatively, at 312 when the one or more processors determine that no P-waves are present within the CA signal, a potential still remains that the CA signal does not correspond to an AF episode. Accordingly, flow advances to 318 where additional analysis is applied to the CA data set. At 318, the one or more processors apply a morphology based premature ventricular contraction (PVC) detection operation. For example, at 318, the one or more processors may implement the QRS complex morphology based PVC detection process described in one or more of the Co-Pending Related Applications referred to above, and filed concurrently on the same day as the present application. The processors determine whether a QRS complex morphology has varied beyond a morphology variation threshold. Variation in the R-wave morphology beyond the morphology variation threshold provides a good indicator that the cardiac events include one or more PVC. When the cardiac events include a sufficient number of PVCs, the process may attribute an R-R interval variation to (and indicative of) PVCs or non-atrial originated beats that lead to significantly different R-R intervals, and not due to (or indicative of) an AF episode. Accordingly, when the R-wave morphology exceeds the morphology variation threshold, flow returns to 316, where the process performs the operations described herein. At 316, one or more flags may be set to indicate that the false AF detection was declared due to one or more PVCs present within the CA data. Additionally or alternatively, a diagnosis may be changed from AF episode to PVC episode. The number of PVC may vary that are needed to achieve an R-wave morphology variation at 318 sufficient for flow to branch to 316 (e.g., declare a false AF detection).

At 318, alternatively, when the R-wave morphology does not exceed the morphology variation threshold, the process interprets the condition as an indicator that the cardiac events do not include significant number of PVCs. Thus, flow moves to 320. At 320, the one or more processors confirm a device documented AF episode and records the current episode to remain as originally declared by the ORI process.

Optionally, the sequence of operations discussed in connection with FIG. 3 may be changed and/or some of the operations may be omitted depending on computational and performance objectives. For example, it may be determined that a low probability exists that a particular patient (or ICM) experiences PVCs that cause false AF detection, and thus, the process of FIG. 3 may omit the PVC detection operation at 318. Additionally or alternatively, it may be determined that a low probability exists that an ICM is incorrectly detecting P-waves as R-waves that would cause false AF detection, and thus, the process of FIG. 3 may omit the P-wave detection operation at 312.

Additionally or alternatively, it may be determined that less processing time/power is utilized to identify P-waves (operations at 312) and/or PVCs (operations at 318) that cause false AF detection, as compared to R-wave detection and analysis of RR interval stability (operations at 306-310). Accordingly, the P-wave and/or PVC detection operations may be performed before the R-wave detection and analysis. In the present example, in the event a P-wave or PVC is detected, the process may declare a CA data set to include a false AF detection without performing the further computations for R-wave detection and analysis.

Optionally, the operations at 308-318 may be modified to not represent binary branches between alternative paths. Instead, the decisions at operations 308-318 may result in a score or a vote, rather than a binary "AF" or "not AF". The vote or score may be variable based upon a degree to which the feature of interest in the confirmatory analysis matches the determination from the original ORI process. Additionally or alternatively, the vote or score may be based on a degree to which the feature of interest from the confirmatory analysis matches one or more baseline values. The votes or scores may be used in conjunction with other AF detection algorithms in order to find a probability that an AF episode has occurred.

The operations of FIG. 3 may be repeated periodically or in response to detection of particular criteria, such as detection of potential atrial fibrillation episodes or otherwise.

The operations of FIG. 3 afford a powerful, sophisticated process to confirm AF detection within ECG and EGM signals in a non-real time manner. The AF detection confirmation processes described herein may utilize computationally expensive analysis that may otherwise not be to be implemented in an on-board circuit within an ICM, either due to memory and power constraints, processing power constraints, and/or an inability to complete the analysis in real time.

Optionally, the operations of one or more of the stages within the process of FIG. 3 may be adapted to run in ICM firmware, although firmware implementations may exhibit different overall performance. In a firmware implementation, a similar form of step-by-step discrimination on existing AF episodes may be achieved. Alternatively, some or all of the features may be adapted for real-time use and set as additional or alternative signals. For example, the determinations at 306-318 may produce factors that are applied to an AF probability and sudden onset determination as AF detection criteria.

FIG. 4 illustrates a flow chart for classifying AF detection and developing recommendations for sensitivity profile parameter settings in accordance with embodiments herein. For example, the operations of FIG. 4 may be performed at 316 and/or 320 in FIG. 3 and/or at other points in the processes described herein. The operations of FIG. 4 build and/or add to a confirmation log that tracks and records the differences and similarities between the results of the EFR and ORI processes. The confirmation log may be stored together with, or separate from, the underlying baseline CA data set and/or the modified CA data set. Optionally, the confirmation log may not represent a separate file, but instead merely represent parameter settings or other information appended to the original or modified CA data set. For example, the confirmation log may be saved as metadata or otherwise appended to the CA data set.

At 402, the one or more processors of the system determine whether the EFR process identified one or more false AF detection by the ORI process applied by the ICM. When the EFR process and the ORI process detect a common or similar number/degree of AF episodes in the CA data set, flow moves to 404. At 404, the one or more processors record a match between the results of the EFR and ORI processes. The match is stored in the confirmation log. When the EFR process identifies a false AF detection that was declared by the ORI process, flow moves to 406.

At 406, the one or more processors classify the false AF detection into one of multiple different categories. Non-limiting examples of the categories include noise, inappropriate sensing, irregular sinus rhythm, frequent PVCs and the like. The processors may classify the false AF detection as noise when the baseline CA data set is determine to have an excessive amount of noise (at 302). For example, the excessive amount of noise may be determined when a number of cardiac events that are removed/suppressed (at 304, 312, 318) exceeds a threshold and/or exceeds a percentage of the total number of cardiac events in the CA data set. The processors may classify the false AF detection as inappropriate sensing when the feature detection (at 306) determines that the CA data includes more or few features of interest (e.g., under-sensed R-waves or over-sensed false R-waves). The processors may classify the false AF detection as sinus rhythm when the P-wave detection (at 312) determines that the CA data set includes one or more P-waves. The processors may classify the false AF detection as frequent PVCs when the PVC detection (at 318) determines that the CA data exceeds a PVC threshold.

At 408, the one or more processors record the classification identified at 406 in the confirmation log. At 410, the one or more processors determine whether additional guidance is to be provided for setting sensitivity profile parameters of the ICM. For example, the processors, at 410, may determine whether an extent or degree of the false R-wave and AF detection (e.g., number of under-sensed R-waves, number of P-waves (as well as T-wave or noise artifact) classified as R-waves, number of frequent PVCs) exceeds a threshold that justifies adjusting one or more sensitivity profile parameters of the ICM. When sensitivity profile parameter adjustments can be made, flow moves to 412. Otherwise, flow continues to 414.

When the extent or degree of the false R-wave and AF detection warrants a parameter adjustment, the sensitivity profile parameter adjustment is determined based in part on the classification at 406. At 412, the one or more processors declare an adjustment to the sensing parameters based on a nature and/or extent of the false R-wave and AF detection. For example, when a false AF detection is classified as due to inappropriate sensing, the processors may declare the sensitivity profile parameter adjustment to be an increase or decrease in the feature (e.g., R-wave) detection threshold. As another example, the processors may declare the sensitivity profile parameter adjustment to be an increase in the R-wave detection threshold when P-waves are identified as R-waves by the ORI process. As another example, the processors may declare the sensitivity profile parameter adjustment to be an increase in the decay delay value when the ORI process over senses T-waves and designates the T-waves to be R-waves. The sensitivity profile parameter adjustment is saved in the confirmation log. Optionally, the confirmation log may also maintain a PVC count.

The increase or decrease in the sensitivity profile parameter adjustment may be a predefined step (e.g., increase threshold by X mV or Y %). Optionally, the increase or decrease may be based on an extent or nature of the false R-wave and AF detection. For example, when the ORI process under-sensed multiple R-waves in the CA data set, the process may decrease the R-wave detection threshold by a larger factor as compared to when the ORI process under-senses one or a few R-waves out of multiple R-waves. As another example, a decay delay value adjustment and/or refractory period value adjustment may be determined based in part on a number of T waves sensed as R-waves, a timing between the T waves and corresponding preceding R-waves, and/or a peak amplitude of the T waves relative to the sensing sensitivity at the time the T-wave is detected.

Optionally, the one or more processors may identify additional or alternative sensitivity profile parameter adjustments based on a database of sensitivity profile parameter settings that are correlated to cardiac activity data for a patient population. For example, a database may be maintained of EGM or ECG data segments collected in connection with numerous patients that experienced AF, sinus rhythms and/or other arrhythmias, where the EGM/ECG data segments are correlated with sensitivity profile parameter settings that are used by a monitoring device to collect the EGM or ECG data. The patient population database may also indicate which sensitivity profile parameter settings achieved desired results and which sensitivity profile parameter settings did not achieve desired results. The database may further include quality indicators indicative of whether the sensitivity profile parameter settings were deemed to collect good or accurate results (e.g., correctly sense R-waves without over-sensing P-waves or T waves, and correctly sense all R-waves without under-sensing of R-waves with smaller amplitude). The database may further include quality indicators indicative of whether the sensitivity profile parameter settings were deemed to accurately declare AF detection in a high percentage of the instances of AF. The quality indicators may be automatically entered based on automated analysis of the data within the database and/or entered by physicians or other medical personnel as sensitivity profile parameter settings are adjusted for individual patients. The database may be available on a medical network, through a cloud computing service and/or other local or remote source.

At 414, the one or more processors compare the current false AF detection, modified CA data set and/or baseline CA data to a database of third-party CA data sets and false/valid AF detections for other patients. The processors may identify matches or similarities between the false/valid AF detection, modified CA data set and/or baseline CA data set, for the current patient, and the corresponding type of AF detections and third-party CA data set from the database of the larger population. When no match occurs, the operations of FIG. 4 end. Alternatively, when one or more matches occur between the current CA data set and the patient population database, flow moves to 416. At 416, the one or more processors identify additional or alternative sensitivity profile parameter adjustments to record in the confirmation log for the present patient based on the matches or similar cases from the database and the present patient.

The sensitivity profile parameter adjustments, in the confirmation log, may be presented on a display of a mobile device, computer, workstation, etc., as a suggestion or option ICM for the physician or other medical personnel to apply to a current. Optionally, the sensitivity profile parameter adjustments may be pushed and uploaded to the ICM from a local portable external device and/or a remote medical network. The sensitivity profile parameter adjustments may be pushed to the ICM at the direction of the physician or other medical personnel, after the physician or medical personnel has reviewed the baseline and/or modified CA data (with R-wave and AF markers) and other statistical information concerning one or more episodes experienced by the patient. Additional or alternatively, the sensitivity profile parameter adjustments may be automatically pushed and uploaded to the ICM at the conclusion of the operations of FIG. 4, such as when the adjustment is within a predetermined limit.

Figure 5:
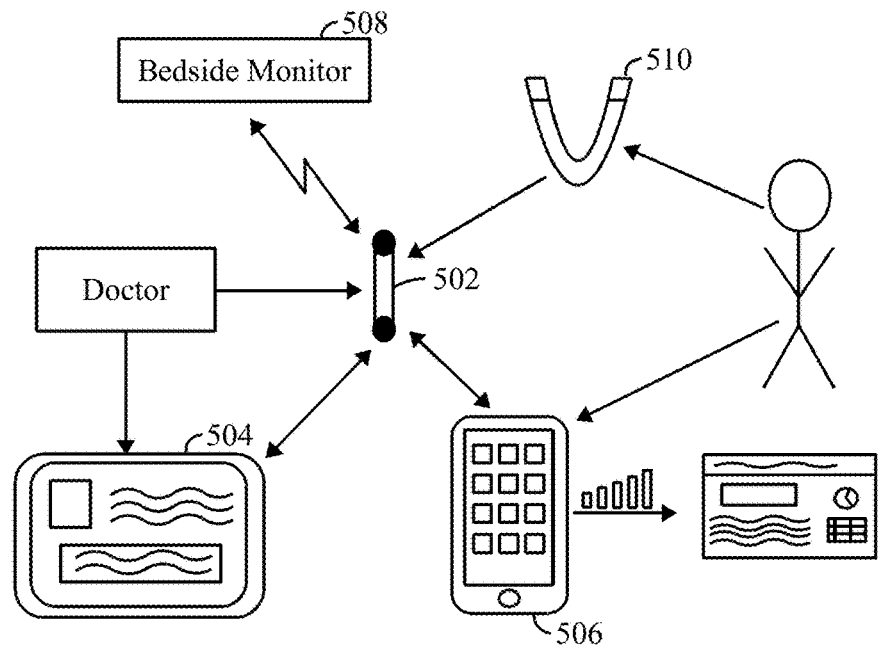
FIG. 5 illustrates a system level diagram indicating potential devices and networks in which the methods and systems herein may be utilized in accordance with embodiments herein.

FIG. 5 illustrates a system level diagram indicating potential devices and networks that utilize the methods and systems herein. For example, an implantable cardiac monitoring device (ICM) 502 may be utilized to collect a cardiac activity data set. The ICM 502 may supply the CA data set (CA signals and DD feature markers) to various local external devices, such as a tablet device 504, a smart phone 506, a bedside monitoring device 508, a smart watch and the like. The devices 504-508 include a display to present the various types of CA signals, markers, statistics, diagnostics and other information described herein. The ICM 502 may convey the CA data set over various types of wireless communications links to the devices 504, 506 and 508. The ICM 502 may utilize various communications protocols and be activated in various manners, such as through a Bluetooth, Bluetooth low energy, WiFi or other wireless protocol. Additionally or alternatively, when a magnetic device 510 is held next to the patient, the magnetic field from the device 510 may activate the ICM 502 to transmit the cardiac activity data set and AF data to one or more of the devices 504-508.

The processes described herein for analyzing the cardiac activity data and/or confirm AF detection may be implemented on one or more of the devices 504-508. Additionally or alternatively, the ICM 502 may also implement the confirmatory processes described herein. The devices 504-508 may present the CA data set and AF detection statistics and diagnostics to clinicians in various manners. As one example, AF markers may be illustrated on EGM signal traces. AF and sinus markers may be presented in a marker channel that is temporally aligned with original or modified CA signals. Additionally or alternatively, the duration and heart rate under AF may be formatted into histograms or other types of charts to be presented alone or in combination with CA signals.

Figure 6:
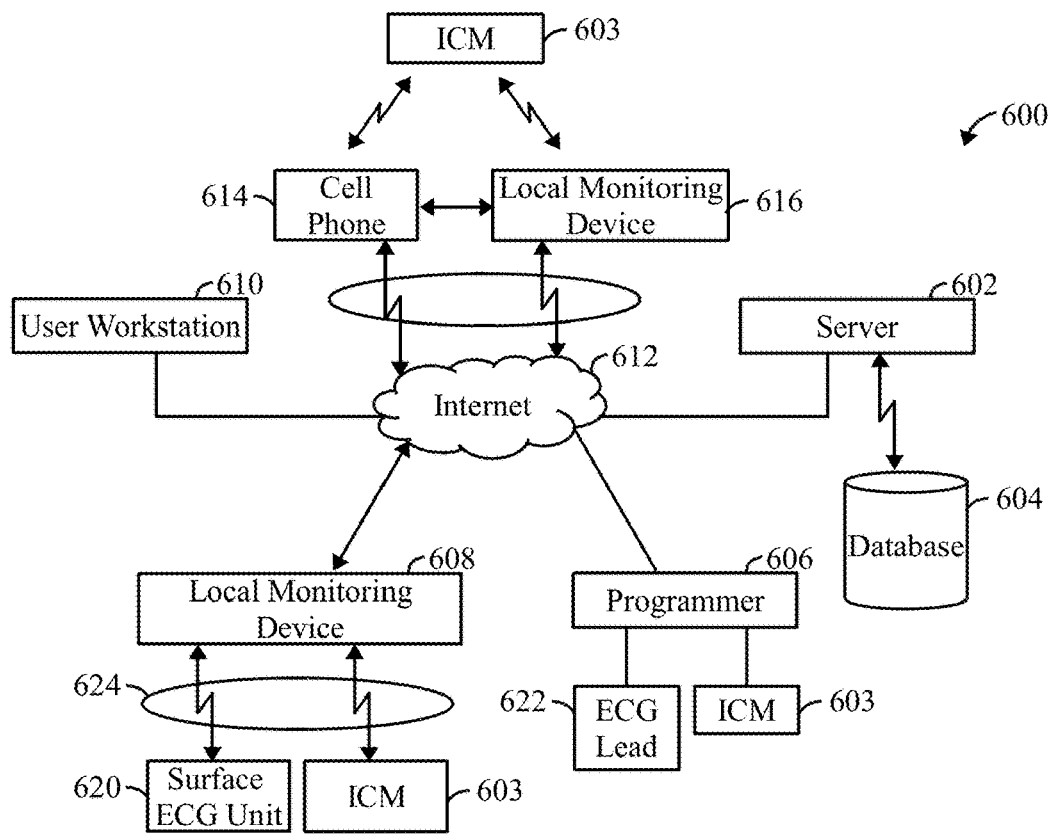
FIG. 6 illustrates a distributed processing system in accordance with embodiments herein.

FIG. 6 illustrates a distributed processing system 600 in accordance with embodiments herein. The distributed processing system 600 includes a server 602 connected to a database 604, a programmer 606, a local monitoring device 608 and a user workstation 610 electrically connected to a network 612. Any of the processor-based components in FIG. 6 (e.g., workstation 610, cell phone 614, local monitoring device 616, server 602, programmer 606) may perform the processes discussed herein.

The network 612 may provide cloud-based services over the internet, a voice over IP (VoIP) gateway, a local plain old telephone service (POTS), a public switched telephone network (PSTN), a cellular phone based network, and the like. Alternatively, the communication system may be a local area network (LAN), a medical campus area network (CAN), a metropolitan area network (MAN), or a wide area network (WAM). The communication system serves to provide a network that facilitates the transfer/receipt of data and other information between local and remote devices (relative to a patient). The server 602 is a computer system that provides services to the other computing devices on the network 612. The server 602 controls the communication of information such as cardiac activity data sets, bradycardia episode information, asystole episode information, AF episode information, markers, cardiac signal waveforms, heart rates, and device settings. The server 602 interfaces with the network 612 to transfer information between the programmer 606, local monitoring devices 608, 616, user workstation 610, cell phone 614 and database 604. The database 604 stores information such as cardiac activity data, AF episode information, AF statistics, diagnostics, markers, cardiac signal waveforms, heart rates, device settings, and the like, for a patient population. The information is downloaded into the database 604 via the server 602 or, alternatively, the information is uploaded to the server 602 from the database 604. The programmer 606 may reside in a patient's home, a hospital, or a physician's office. The programmer 606 may wirelessly communicate with the ICM 603 and utilize protocols, such as Bluetooth, GSM, infrared wireless LANs, HIPERLAN, 3G, satellite, as well as circuit and packet data protocols, and the like. Alternatively, a telemetry "wand" connection may be used to connect the programmer 606 to the ICM 603. The programmer 606 is able to acquire ECG 622 from surface electrodes on a person (e.g., ECGs), electrograms (e.g., EGM) signals from the ICM 603, and/or cardiac activity data, AF episode information, AF statistics, diagnostics, markers, cardiac signal waveforms, atrial heart rates, device settings from the ICM 603. The programmer 606 interfaces with the network 612, either via the Internet, to upload the information acquired from the surface ECG unit 620, or the ICM 603 to the server 602.

The local monitoring device 608 interfaces with the communication system to upload to the server 602 one or more of cardiac activity data set, AF episode information, AF statistics, diagnostics, markers, cardiac signal waveforms, heart rates, sensitivity profile parameter settings and detection thresholds. In one embodiment, the surface ECG unit 620 and the ICM 603 have a bi-directional connection 624 with the local RF monitoring device 608 via a wireless connection. The local monitoring device 608 is able to acquire cardiac signals from the surface of a person, cardiac activity data sets and other information from the ICM 603, and/or cardiac signal waveforms, heart rates, and device settings from the ICM 603. On the other hand, the local monitoring device 608 may download the data and information discussed herein from the database 604 to the surface ECG unit 620 or the ICM 603.

The user workstation 610 may be utilized by a physician or medical personnel to interface with the network 612 to download cardiac activity data and other information discussed herein from the database 604, from the local monitoring devices 608, 616, from the ICM 603 or otherwise. Once downloaded, the user workstation 610 may process the CA data in accordance with one or more of the operations described above. The user workstation 610 may upload/push settings (e.g., sensitivity profile parameter settings), ICM instructions, other information and notifications to the cell phone 614, local monitoring devices 608, 616, programmer 606, server 602 and/or ICM 603. For example, the user workstation 610 may provide instructions to the ICM 603 in order to update sensitivity profile parameter settings when the ICM 603 declares too many false AF detections.

The processes described herein in connection with analyzing cardiac activity data for confirming or rejecting AF detection may be performed by one or more of the devices illustrated in FIG. 6, including but not limited to the ICM 603, programmer 606, local monitoring devices 608, 616, user workstation 610, cell phone 614, and server 602. The process described herein may be distributed between the devices of FIG. 6.

Figure 7:
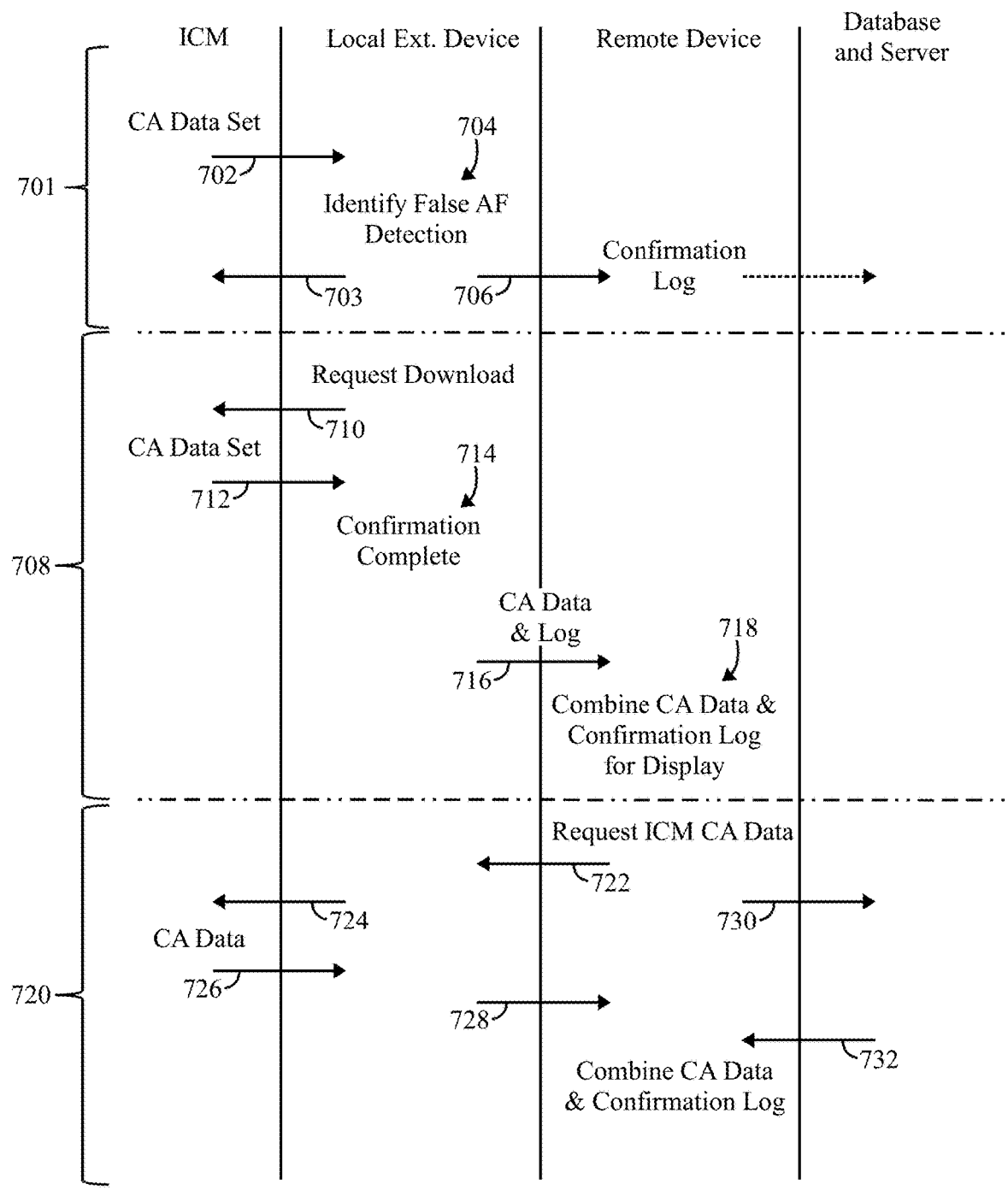
FIG. 7 illustrates a collection of communications between the ICM, a local device, a remote device and a server/database in accordance with embodiments herein.

FIG. 7 illustrates examples of communication sessions between the ICM, a local external device, a remote device and a server/database in accordance with embodiments herein. For convenience, reference is made to the devices of FIGS. 5 and 6, in connection with FIG. 7. For example, the local device may represent a cell phone 614, smart phone 506, bedside monitor 508 or local monitoring device 608, 616, while the remote device may represent a workstation 610, programmer 606, or tablet device 504.

During an AF detection and confirmation session 701, at 702, an ICM 100 provides a CA data set to a local device. At 704, the local device utilizes the EFR and confirmatory feature detectors processes described herein to analyze at least a portion of the CA signals to identify false AF detection. The false AF detections are used to generate or update a confirmation log 706. As described herein, the confirmation log 706 may include a log of the "false positive" episode counts from the original CA data set. The confirmation log 706 may include, among other things, confirmatory markers, confirmatory episode statistics and confirmatory arrhythmia diagnostics that may differ from or be similar to the original episode statistics 147 and arrhythmia diagnostics 149 (FIG. 2C). The confirmation log 706 may also include corrective characterizations of individual events that were mischaracterized in the original CA data.

In certain instances, it may be desirable to return the confirmation log 706 information to the ICM as denoted at 703. In certain implementations, an ICM is provided with certain security features that prevent an external device (e.g., cell phone or local monitoring device) from directly changing sensitivity profile parameter settings and/or writing to any or at least certain sections of the memory within the ICM. For example, the security features may prevent an external device from writing over-sensitivity profile parameter settings and/or over the AF statistics and diagnostics that are generated and stored on the ICM.

Optionally, as a workaround, at 703, the confirmation log 706 may be written to a more flexible section of memory within the ICM (also referred to as an external device accessible section), along with header and/or metadata information tying the confirmation log 706 to a particular portion of the CA data. Additionally or alternatively, at 704, the local external device may pass the confirmation log 706 to one or more remote devices and optionally to the database and server. The confirmation log 706 may be written to memory of an external device that interacts directly and regularly with the ICM, such as cell phone 614, local monitoring device 608, 616 and the like. The confirmation log 706 may be associated with particular CA data sets, such as based on time of data acquisition.

Optionally, a remote pairing session 708 may be performed between CA data on an ICM and locally externally stored confirmation logs. For example, the local external device may be directed to initiate a data transfer/download from the ICM, such as at 710, at a point in time separate from and after performing the AF detection confirmation processes described herein. The local external device receives the CA data set at 712 and determines, at 714, that the CA data set has already been analyzed to confirm AF detection. At 716, the local external device identifies a confirmation log 706 stored at the local external device that corresponds to the CA data set, and at 716, appends the confirmation log 706 to the associated CA data set, such as based on time of data acquisition. The cumulative information of the CA data set and confirmation log 706 are transferred, through the external device, to a remote server 602, database 604, workstation 610, programmer 606 or otherwise.

By maintaining the confirmation log, for a particular CA data set at the local external device in association with the original CA data set, remote devices (e.g., programmer 606, server 602, etc.) receive and process both the original CA data set and the confirmation log. The remote device obtains the "traditional" device diagnostic sections, and is also afforded additional information from the confirmation log and is able to account (at 718) for cumulative adjustments/adjudications in AF detection before displaying a consolidated set of AF statistics and diagnostics to a physician or medical personnel.

Additionally or alternatively, the operations of FIG. 7 may be implemented in connection with remotely stored confirmation logs, such as in communication sessions 720. At 722, a remote device may request CA data from a particular ICM by conveying a corresponding request to a local external device associated with the corresponding ICM. The local external device forwards the data request, at 724, to the ICM, in response thereto, at 726, the ICM transmits the CA data set to the local external device. The local external device forwards the CA data set, at 728, to the remote device. Optionally, before relaying the CA data set, at 728, the local external device may first determine whether the CA data set has first been analyzed for AF detection confirmation. In the example at 720, it is presumed that the CA data set has already been analyzed for AF detection confirmation and thus the local external device need not perform the confirmation analysis at this time. Additionally or alternatively, the remote device may include, in the request, a direction to the local external device to not perform AF detection confirmation (e.g., the remote device knows that in AF detection confirmation has already been performed and stored elsewhere).

In connection with or separate from the request for CA data set at 722, the remote device conveys a request, at 730, to a server and database for any confirmation logs related to the requested CA data set. The requested may be broadcast to multiple external devices on the network or directed to a particular server/database known to maintain information in connection with the particular ICM. Additionally or alternatively, the remote device may hold the request, at 730, until after receiving the CA data set, at 728. For example, once a remote device receives the CA data set, at 728, the remote device may include, within the request for confirmation logs, an indication of the time and date at which the CA data set was collected. In response to the request, the server and database return, at 732, one or more confirmation logs (if present). Thereafter, the remote device combines the CA data set and confirmation log 706 to present a consolidated summary of the data to a physician or other medical personnel.

In connection with embodiments herein, the cloud-based approach allows an AF episode that is detected by the ICM using the traditional detection algorithms, to be passed through the local external device and stored at the server 602, database 604, workstation 610 or at another remote device within the cloud-based system. When an individual ICM is interrogated for a CA data set, the interrogation device would also request, from the cloud-based system, any additional information, such as any confirmation logs stored elsewhere within the system. For example, when an external device, such as a cell phone 614, local monitoring device 608, 616 and/or programmer 606 interrogate an individual ICM, the cell phone 614, local monitoring device 608, 616 and/or programmer 606 would also broadcast an ICM data supplement request over the cloud-based system. The ICM data supplement request requests additional data/information related to the individual ICM (e.g., based on the ICM serial number). In response thereto, the server 602 and/or other remote system may provide, to the requesting device, one or more confirmation logs or other information regarding past operation of the ICM. The requesting device then combines the CA data set from the ICM with related data (e.g., a confirmation log associated with a particular AF episode and/or group of cardiac events) from an external source. The external devices pulls data from the cloud in connection with ICM interrogation, and combine the CA data from the ICM with any corrective or confirmation data from the log, before presenting a consolidated data summary to a physician or medical personnel.

Next, alternative embodiments are described for detecting R-waves in connection with a first pass or second pass arrhythmia detection process. The R-wave detection processes of FIGS. 9 and 10 may be implemented by firmware on an ICM, IMD, local external device or remote server, as a first pass process in connection with arrhythmia detection. Additionally or alternatively, the R-wave detection processes of FIGS. 9 and 10 may be implemented by firmware on an ICM, IMD, local external device or remote server, as a second pass confirmation process, where cardiac activity signals have been previously analyzed by an AF detection module, such as the ORI process described in connection with FIGS. 2A and 2B. The process may initiate the operations of FIGS. 9 and 10 in an attempt to verify whether one or more episodes in a CA data set, are in fact an AF episode or a normal rhythmic/sinus episode. Optionally, the operations of FIGS. 9 and 10 may be implemented in connection with a CA data set that has not been previously analyzed for potential AF episodes. The operations of FIGS. 9 and 10 may be implemented as part of a local or distributed system, such as by the microcontroller 121 of the ICM, by a local external device and/or a remote server.

Figure 8A:
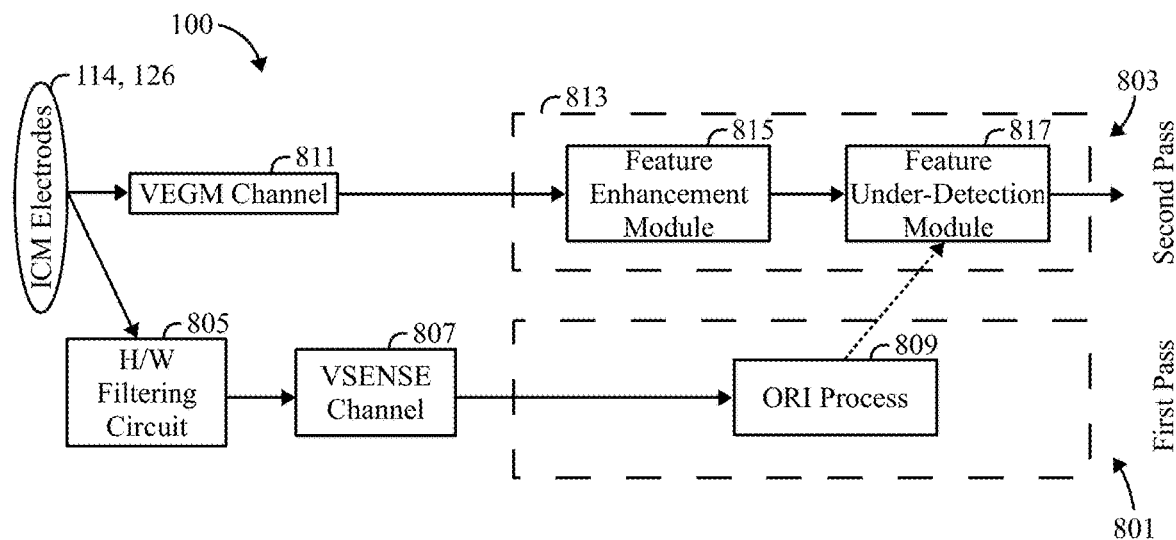
FIG. 8A illustrates a block diagram of parallel signal processing paths implemented in accordance with embodiments herein.

III. Alternative Embodiment—Improved R-wave Detection Algorithm—Bradycardia and Asystole Episodes Using a Second Pass Detection Workflow FIG. 8A illustrates a block diagram of parallel signal processing paths implemented in accordance with embodiments herein. In FIG. 8A, the ICM 100 collects CA signals for a series of cardiac events or beats through far field sensing by two or more electrodes 114, 126 on or proximate to the housing of the ICM 100. By way of example, the ICM 100 may perform sensing using wide frequency bandpass filter to collect EGM (or VEGM) signal that contains P, QRS, and/or T-waves. The VEGM signal is processed along a primary sensing channel (or first pass) 801 and a secondary/confirmation sensing channel (or second pass) 803. In the primary sensing channel 801, sensed cardiac activity signals (e.g., VEGM signals) are passed through a hardware filtering circuit 805 to form a filtered cardiac activity signal VSENSE 807. The VSENSE signal 807 is analyzed by an onboard arrhythmia detection process within the ICM, generally referred to as an onboard RR interval irregularity (ORI) process 809. The ORI process 809 identifies R-waves and arrhythmia episodes using the VSENSE signal 807, stores binning information in connection with, and designates device documented markers, such as R-wave markers and arrhythmia markers, that are temporally aligned with the VSENSE signal 807.

In addition, the VEGM signal 811 is processed along the secondary/confirmation sensing channel 803, wherein the VEGM signal 811 is directly analyzed by a second pass detection algorithm 813 as described herein. In accordance with embodiments herein, methods and systems are described that utilize the second pass detection algorithm 813 to improve physiologic signal sensing (e.g., R-waves) in connection with arrhythmia episodes (e.g., bradycardia, tachycardia and asystole). The detection algorithm 813 applies a feature enhancement process 815 to the secondary sensed signal (e.g., the VEGM signal) to form a modified secondary CA signal. The modified secondary CA signal includes enhanced features of interest (e.g., QRS complex and R wave peak) and suppressed features that are not of interest (e.g., P-wave, T-wave, baseline noise). The feature enhancement process 815 includes signal conditioning, noise reduction and peak sensing. The detection algorithm 813 also includes a feature under-detection process 817. The feature under-detection process 817 analyzes the modified cardiac activity signal for under detected features of interest. While analyzing the modified cardiac activity signal, the process 817 automatically adjusts an adaptive sensitivity threshold that is applied to the modified CA signal. The adaptive sensitivity threshold changes between events and/or episodes. The detection algorithm 813 provides a reduction in false declaration of bradycardia and asystole episodes by the ORI process 809, while maintaining the sensitivity in detecting true bradycardia and asystole episodes. In particular, the detection algorithm 813 provides a high level of sensitivity in connection with bradycardia and asystole episodes due, in part to, (1) using signal characteristics in the VEGM signal in the interval prior to these episodes to select a more appropriate threshold of sensing and (2) incremental adjustment of the adaptive sensitivity level until an R-wave is detected or a calculated lowest allowed sensitivity limit is reached.

In the example of FIG. 8A, the secondary signal represents a sensed signal such as a VEGM signal 811. Optionally, the secondary signal may represent a sensed signal derived by mathematical transformation. The detection algorithm 813 affords a computationally simple process that may be implemented on board the ICM, such as at the firmware level. Optionally, the detection algorithm 813 may be implemented at a mid-ware level, such as on a local external device (e.g., cell phone, tablet device, Merlin®home™ transmitter) that communicates with the implanted device, and/or at a software level such as on a remote monitoring server (e.g., the Merlin.net™ Patient care network, a device data translator).

Figure 8B:
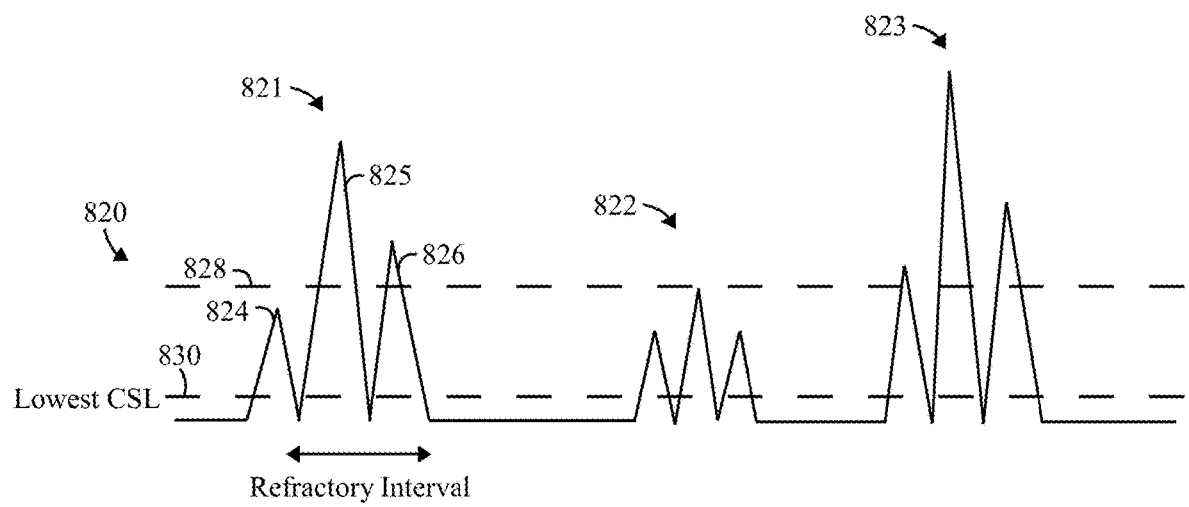
FIG. 8B illustrates a portion of rectified CA signal processed by the second pass detection/confirmation algorithm of FIG. 8A in accordance with embodiments herein.

FIG. 8B illustrates a portion of rectified CA signal processed by the second pass detection/confirmation algorithm 813 of FIG. 8A. The rectified CA signal 820 illustrates QRS complexes for cardiac events or beats 821-823, each of which includes QRS complex that is rectified to include three positive peaks. In the example of FIG. 8B, the QRS complex of beat 823 includes rectified local peaks 824-826. FIG. 8B also illustrates a dashed line which corresponds to a sensitivity level 828 utilized by the ICM 100 (FIG. 8A). The adaptive sensitivity limit 830 is the lowest sensitivity level allowed for detecting a QRS complex. When a QRS complex, such as in beat 823, exceeds the sensitivity level 828, the ICM 100 declares an R-wave. Alternatively, when the QRS complex does not exceed the sensitivity level 828, such as in beat 822, the ICM 100 does not declare an R-wave and the beat 822 goes under detected, thereby resulting in the ICM 100 improperly annotating beat 823 as an abnormal or bradycardia beat due to the long interval from previously sensed beat 821

In accordance with embodiments herein, the second pass detection/confirmation algorithm 813 (as described in connection with FIG. 9A) sets the adaptive sensitivity limit 830 at a level having greater sensitivity relative to the sensitivity of conventional ORI process 809. Consequently, the R-wave peak of beats 821, 822, 823 are properly detected and properly classified.

Figure 9A:
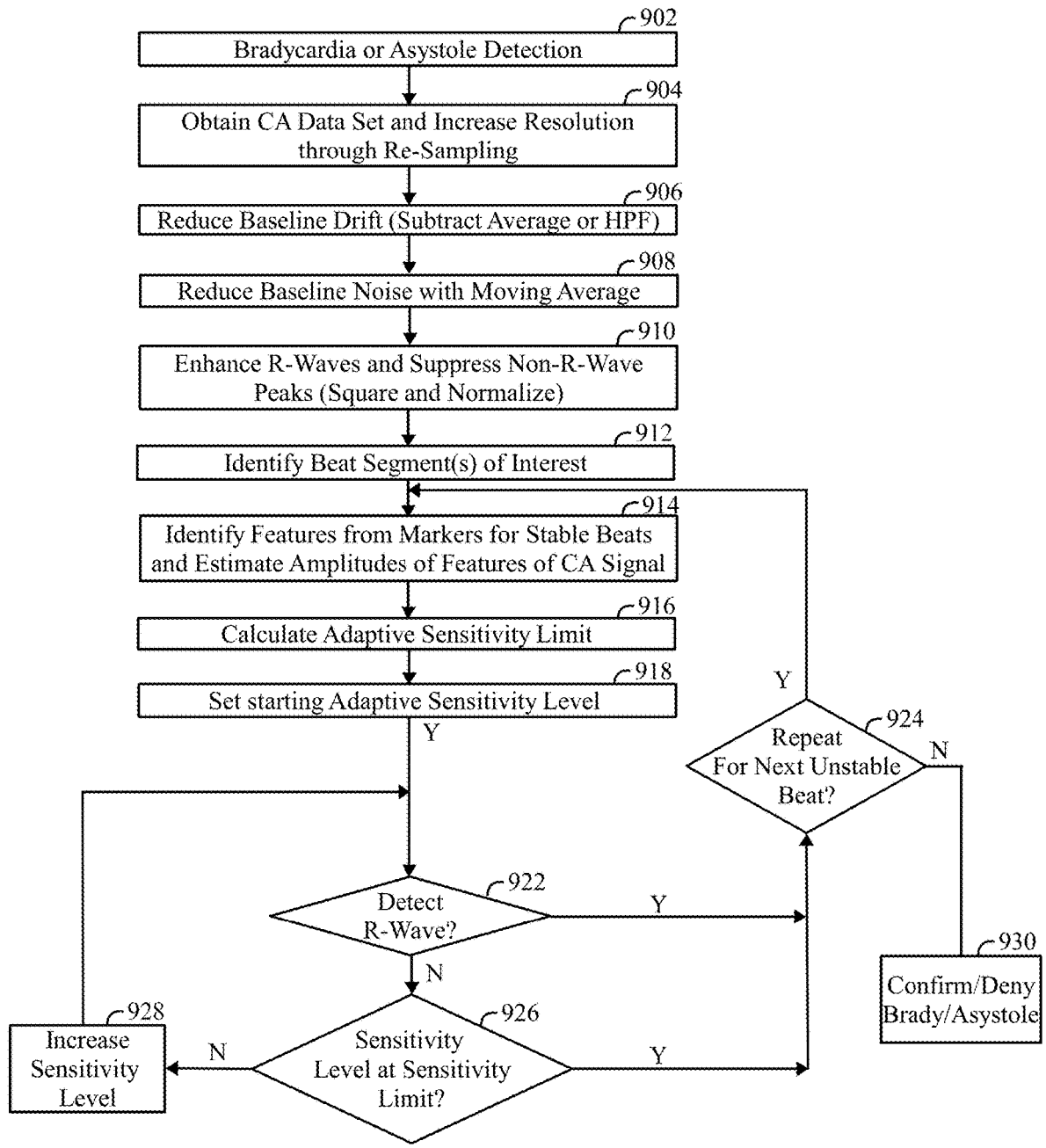
FIG. 9A illustrates a process for detecting bradycardia and asystole episodes implements by the second pass detection algorithm in accordance with embodiments herein.

FIG. 9A illustrates a process for detecting bradycardia and asystole episodes implements by the second pass detection algorithm 813 in accordance with embodiments herein. At 902, one or more processors determine that the ICM device documented bradycardia episode or asystole episode based on cardiac activity signals detected in the primary sensing channel 801. For example, the ORI process 809 applies an R-wave sensing and RR interval based bradycardia and asystole detection algorithm implemented by the ICM. When an RR interval exceeds bradycardia and/or asystole detection cutoff limits the ICM declares a bradycardia episode and/or an asystole episode.

Optionally, the operations at 904-910 perform preconditioning and feature enhancement upon the original CA signal received over the secondary sensing channel 803 to, among other things, improve a signal-to-noise ratio for the feature of interest (e.g., the peak of the R-wave) in the CA signal. For example, the operations at 904-910 may be implemented by the feature enhancement process 815 (FIG. 8A). At 904, the one or more processors resample the CA signal (e.g., utilizing interpolation) to increase a resolution of the data samples within the CA data set for the CA signal. Resampling the CA signals allows relatively more precise settings of thresholds and more detailed sensing operations to be performed at later operations in FIG. 9A. By way of example, the original CA signals (e.g., VEGM signals) may be defined by a CA data set that has a sample frequency of 128 Hz, whereas the resampling and interpolation increase the sample resolution to 512 Hz. Various types of interpolation may be applied, such as linear interpolation or Shannon interpolation, in which zeros are added between points and the signal is digitally low-pass filtered and multiplied by the reciprocal of the up-sampled ratio. Alternative techniques may be applied to increase the data sample resolution.

The interpolation and resampling operation at 904 may be desirable when the CA data set is stored at relatively low resolution. For example, while the ICM may digitize sensed signals at a higher resolution and initially analyze the digitized signals at the higher resolution, the ICM may not include sufficient memory to store all of the data for the CA signal at the higher digital resolution. Consequently, the resolution of the CA signal may be reduced before the digital data is stored in memory. As another example, the resolution of the data may be reduced in connection with transmission from the ICM. For example, before transmitting a CA data set, the ICM may down sample the digitized data, in order to maintain a desired data rate and/or to conserve power by reducing the overall data to be transmitted.

Optionally, when the CA data set is stored with sufficient resolution and/or transmitted from the ICM with sufficient resolution, the resampling and interpolation operation at 904 may be omitted entirely.

At 906, a baseline drift reduction operation is performed. The one or more processors may step through the data samples and subtract a moving average from the CA signal. For example, a long (e.g., one second) moving average of the CA signal may be subtracted from the CA signal at each data point. Additionally or alternatively, the drift reduction operation may be performed by applying a high pass digital filter having corresponding desired filter characteristics.

At 908, a baseline noise reduction operation is performed. For example, the one or more processors may step through the data samples of the CA signal and apply a moving average at each data sample. For example, the moving average window, having a predetermined length (e.g., 10 msec.), may be applied to replace each data point along the CA signal with an average of the data points surrounding the current data point within the moving average.

At 910, the one or more processors apply a feature enhancement function along the CA signal to form an enhanced feature of interest (e.g., a peak of the R-wave). The feature enhancement function also suppresses features that are not of interest. By way of example, the one or more processors may apply non-linear scaling function (e.g., an amplitude squaring) and normalization function along the CA signal to enlarge and/or sharpen peaks of the R-wave. For example, the normalization may be achieved by dividing each data point along the CA signal by a percentage of a peak of the R-wave (e.g., data point 1 divided by 80% of the R-wave peak). By normalizing the CA signal to a value less than the peak of the feature of interest, the normalization will enhance R-wave peaks, while suppressing non-R-wave features such as P-waves, T-waves, noise and other features that are not of interest. The non-linear scaling operation has a similar effect by enhancing the R-wave peaks and suppressing non-R-wave features.

Next, the process of FIG. 9A begins a search through the CA data set for beat segments of interest suspected of under-sensing. As noted herein, the CA data set includes a marker channel that includes a series of device documented markers temporally associated with features of interest from one or more CA signal channels that include corresponding CA signals. The device documented (DD) markers are declared by the ORI process 809 in real-time. At 912, the one or more processors identify beat segments of interest from the CA data set based on the marker channel. For example, the processors may identify the beat segments of interest of the CA signal as the segments that correspond to triggering the DD arrhythmia markers At 914, the one or more processors review the marker channel within the CA data set to identify beats that were identified by the ICM (and ORI process) to have stable RR intervals. The processors may identify all or a portion of the segments of the CA data set that have stable RR intervals. The processors utilize the markers from the marker channel, associated with the CA signal segments, to identify the feature of interest, such as R-waves, P-waves, T-waves, etc. The one or more processors determine amplitudes (e.g., amplitude estimates) for the features of the CA signal segments having stable RR intervals. For example, the processors may estimate amplitudes for R-wave peaks, T-wave peaks, P-wave peaks, isoelectric segments and the like for stable beats. The amplitude estimates can be used to determine an ensemble characteristic for each feature (e.g., ensemble P-wave peak amplitude, ensemble R-wave peak amplitude, ensemble R-wave peak amplitude variability, ensemble T-wave peak amplitude).

Figure 8C:
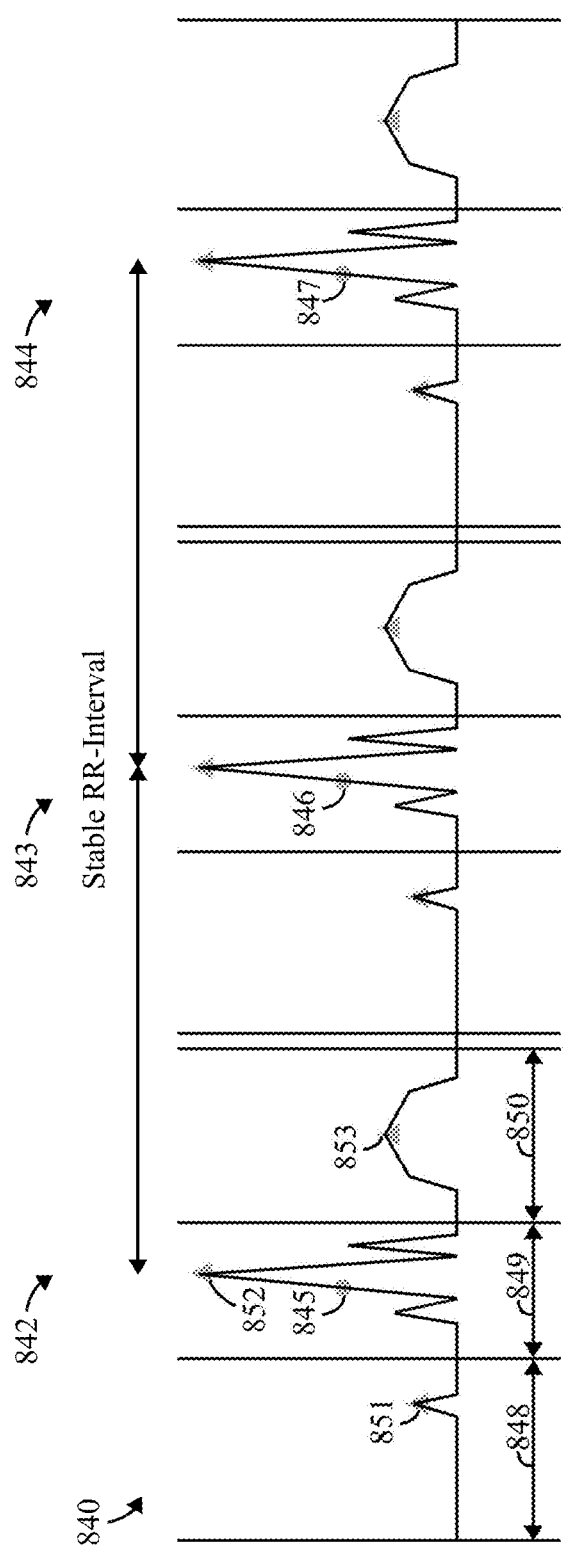
FIG. 8C illustrates a portion of a CA data set that is analyzed in connection with the operation at to identify amplitudes of features of interest in accordance with embodiments herein.

FIG. 8C illustrates a portion of a CA data set 840 that is analyzed in connection with the operation at 914 to identify amplitudes of features of interest. In FIG. 8C, the CA data set 840 includes beats or cardiac events 842-844. The CA data set 840 also includes a marker channel (illustrated superimposed upon the CA signal). The marker channel includes R-wave markers 845-847 identified in real-time by the ICM in connection with the corresponding cardiac events 842-844.

During the amplitude estimation operation at 914, the one or more processors use the R-wave markers 845-847 as reference points relative to each corresponding cardiac event 842-844. The processors define search windows 848-850 for a corresponding cardiac event 842, with respect to an R-wave marker 845. For example, an R-wave search window 849 may be defined to be centered at the R-wave marker 845. A P-wave search window 848 may be defined to precede the R-wave search window 849, while a T-wave search window 850 may be defined to follow the R-wave search window 849. Search windows 848-850 can be constant or dependent on RR intervals or other functions.

Once the P-wave, R-wave and T-wave search windows 848-850 are defined, the one or more processors analyze the CA signal within the corresponding windows 848-850 to identify a peak therein. In the example of FIG. 8C, P-wave, R-wave and T-wave peaks 851-853 are illustrated as determined by the foregoing process. The amplitudes of peaks 851-853 are then utilized to calculate a starting value for the adaptive sensitivity level as described hereafter. Multiple beats are analyzed to determine ensemble amplitudes for P, R and T-wave peaks.

Returning to FIG. 9A, at 916, the one or more processors utilize the ensemble amplitudes of the features of interest to calculate a starting value for the adaptive sensitivity level. For example, the starting value of the adaptive sensitivity level may be determined based on a comparison of a weighted ensemble R-wave peak, weighted ensemble T-wave peak and weighted ensemble P-wave peak. The term "ensemble" is used to refer to estimate of the amplitude of a group of wave peaks of interest within a current CA data set (e.g., the highest R-wave peak within a 90 millisecond strip of EGM signals) or a select segment of the CA data set. For example, the processors may apply weighting factors and constant offsets to the amplitude estimates and then select a weighted amplitude estimate having a desired characteristic relative to other weighted amplitude estimates. As one non-limiting example, the processors may determine the lower of $R_{ENS-W}$ and $T_{ENS-W}$, where $R_{ENS-W}$ represents ensemble R-wave peak multiplied by an R-wave weighting factor (e.g., 50%) plus a constant offset (e.g., 10 mV) and $T_{ENS-W}$ represents an ensemble T-wave peak multiplied by a T-wave weighting factor (e.g., 120%) plus a constant offset (e.g., 10 mV). The lower of $R_{ENS-W}$ and $T_{ENS-W}$ represents an $RT_{min}$, namely a minimum RT reference level that is greater than the T-wave peak and less than the R-wave peak. The processors may then determine the higher of the $RT_{min}$ and a $P_{ENS-W}$, where $P_{ENS-W}$ represents a ensemble P-wave peak multiplied by a P-wave weighting factor (e.g., 120%) plus a constant offset (e.g., 20 mV). The processors determine the higher of the $RT_{min}$ and $P_{ENS-W}$ to avoid setting an upper sensitivity threshold near a noise floor. The higher of the $RT_{min}$ and $P_{ENS-W}$ is used to set the adaptive sensitivity level. For example, the adaptive sensitivity level may be set to equal the higher of the $RT_{min}$ and $P_{ENS-W}$. Optionally, the adaptive sensitivity level may be set to be a percentage of, or a predetermined amount above/below the higher of the $RT_{min}$ and $P_{ENS-W}$.

The sensitivity level may be modified in connection with different beat segments of interest within a CA data set. For example, a new adaptive sensitivity level may be set for each beat segment of interest or groups of beat segments of interest. Alternatively, the sensitivity level may be modified once in connection with each CA data set.

Optionally, the one or more processors may utilize an average peak amplitude of one or more features of interest as the "ensemble" amplitude of the feature of interest. For example, an average peak R-wave amplitude may be determined for all or a subset of the stable beats within the CA data set, where the average peak R-wave amplitude is used to obtain the weighted ensemble R-wave amplitude. A similar operation may be implemented for an average P-wave peak amplitude and an average T-wave peak amplitude. Optionally, the operation at 912 to identify one or more beat segments of interest may be reordered to occur after 914 and/or after 916.

Figure 9B:
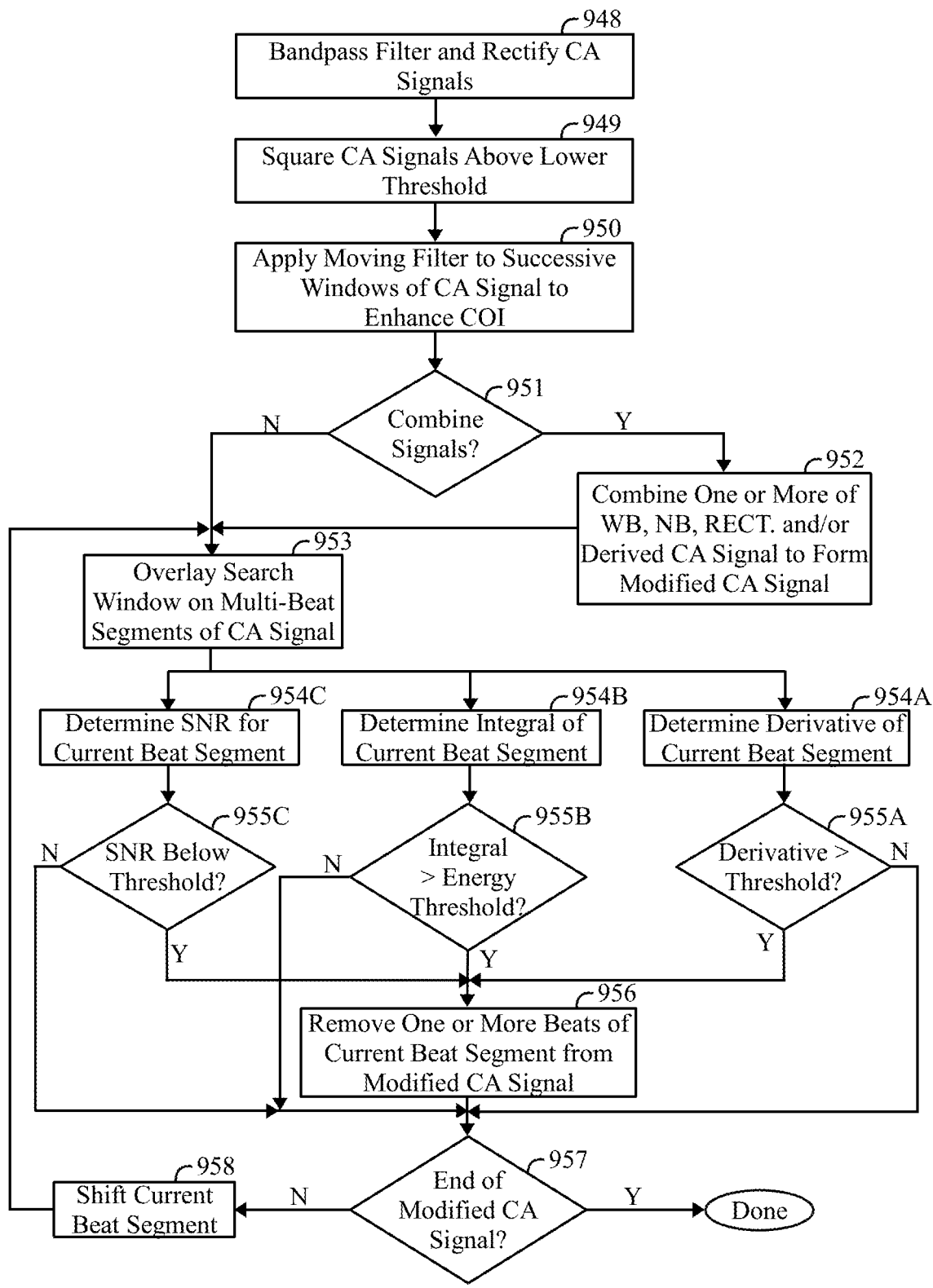
FIG. 9B illustrates an example process for detecting unanalyzable beat segments due to noise in accordance with an embodiment herein.

At 918, the one or more processors set a starting adaptive sensitivity level based on amplitudes of the features of interest from the preceding beat and/or based on an ensemble average of features of interest from a collection of preceding beats. FIG. 9B illustrates an example process for detecting unanalyzable beat segments due to noise in accordance with an embodiment herein.

Additionally or alternatively, a one-shot adaptive sensitivity level may be set to a percentage or portion of the adaptive sensitivity limit, a percentage or portion of a feature of interest, a programmed level and the like. By way of example, the adaptive sensitivity level may be determined based on ensemble of prior R-wave amplitude and ensemble R-wave variability in the segment of interest. For example, when the ensemble R-wave peak amplitude is a relatively large and ensemble R-wave variability is low, the adaptive sensitivity level may be assigned weighted ensemble of R-wave peak amplitude (e.g., 50% of prior R-wave). Alternatively, when the ensemble R-wave peak amplitude is medium and ensemble R-wave variability is medium, the adaptive sensitivity level may be assigned a slightly small weighted ensemble of R-wave peak amplitude (e.g., 30% of prior R-wave). As another example, when the ensemble R-wave peak amplitude is small or ensemble R-wave variability is above medium, the adaptive sensitivity level may be assigned a weighted combination of T-wave peak amplitude ensemble and/or weighted combination of P-wave peak amplitude ensemble plus an offset (e.g., the minimum of 1.1*T-wave ensemble peak amplitude+0.10 mV and 1.2*P-wave ensemble+0.020 mV). The low, intermediate and high levels of variability may be predetermined and/or automatically calculated by the ICM over time.

At 922, the one or more processors apply the current sensitivity level to perform an R-wave detection process to the current segment of interest beat. For example, the processors analyze the CA signal segment to search for features of interest, such as P-waves, R-waves and T-waves. At 922-928, the one or more processors automatically iteratively analyze a current beat segment of interest. At 922, the one or more processors determine whether one or more R-waves are present within the beat segment of interest. For example, the processors may compare the CA signal to the current adaptive sensitivity level in the beat segment of interest. The processors may determine whether one or more peaks of the current beat segment of interest exceed the current adaptive sensitivity level. When the one or more peaks of the beat segment of interest, exceed the current adaptive sensitivity level, the process determines that the beat segment of interest includes an R-wave. In accordance with an embodiment, the processors identify the point in the beat segment of interest that exceeds the current adaptive sensitivity level as R-wave.

Additionally or alternatively, the processors may identify local peaks within the beat segment of interest and compare the peaks to identify a largest one of the local peaks as the peak of the R-wave. For example, the processors may search the beat segment of interest for a feature of interest, such as a peak of R-wave.

When an R-wave is detected at 922, flow moves to 924. At 924, the one or more processors determine whether to repeat the operations in connection with a next beat segment (s) of interest. Alternatively, at 922, when the processors determined that no R-wave was detected, flow branches to 926.

At 926, the one or more processors determine whether the current sensitivity level has reached the lowest adaptive sensitivity limit (determined at 916) associated with the current segment or CA data set. When the current sensitivity level reaches the lowest adaptive sensitivity limit, flow moves to 924. At 924, the processors determine whether to repeat the operations in connection with a next beat segment of interest. Alternatively, at 926, when the current sensitivity level has not yet reached the adaptive sensitivity limit, flow branches to 928. At 928, the one or more processors increase the current sensitivity level (e.g., by 5%, 10%, 20% or 0.010 mV) and flow returns to 922. It should be recognized that by increasing the sensitivity in the context of sensing R-wave, the processors numerically decreases the value of the adaptive sensitivity level/limit.

In the present example, the lowest adaptive sensitivity limit is calculated for a segment of the CA data set. Optionally, the lowest adaptive sensitivity limit may be determined once for the entire CA data set, and not repeatedly calculated in connection with each beat segment of interest and/or groups of beat segment of interests.

In the foregoing manner, the operations at 914-928 repeat the iterative analysis at 922 while progressively adjusting the current adaptive sensitivity level until i) one or more R-waves or CA signal are detected in the beat segment of interest and/or ii) the current sensitivity level reaches the lowest adaptive sensitivity limit. When an R-wave or CA signal is detected within the current beat segment or the sensitivity limit is reached, flow passes to 924 to determine whether additional beat segments of interest exist. When additional beat segments exist, the process returns to 914 and a new starting adaptive sensitivity threshold is determined for the next beat segment of interest. Otherwise, the process moves to 930. Alternatively, a one-time R-wave adaptive sensitivity level using step 922 can be performed without steps of 926 and 928 to reduce the calculation burden introduced by the iterative analysis.

At 930, the one or more processors analyze the beat segment of interest to detect whether an arrhythmia is present. The detection of the arrhythmia is based at least in part on a presence or absence of one or more R-waves within the beat segment of interest. For example, the processors may confirm or deny the presence of a bradycardia episode and/or in asystole episode within one or more beat segment of interests. In connection with bradycardia episodes, the processors may maintain a running count of a number of beats having RR intervals that are sufficiently long (exceed a bradycardia RR interval threshold) to be indicative of a bradycardia episode. The processors may also maintain a running count of a total number of beats being analyzed from the CA data set. A bradycardia episode may be confirmed or denied based on a number of X beats within a bradycardia zone out of a number of Y total beats over all or a portion of the CA data set. For example, the one or more processors may maintain a bradycardia bin counting a number of beats that exhibit an RR interval within a bradycardia zone. The processors may also maintain a bin counting a total number of beats. When the bradycardia bin count, relative to the total beat bin count, exceeds a threshold, the processors declare a bradycardia episode.

At 930, in connection with confirming or denying an asystole episode within one or more beat segment of interests, the one or more processors may track a time period (e.g., greater than X seconds) during which no detected activity-waves occurs within the beat segment of interest. When the period of time, with no detected electrical activity, exceeds an asystole threshold, the processors declare an asystole episode.

Optionally, an additional iterative stage may be applied in connection with bradycardia sensing, wherein incrementally lower new sensitivity levels (e.g., greater sensitivity) are applied when calculating the current adaptive sensitivity level at 918. The new sensitivity levels may be incremented based on other continuing/stopping criteria in a manner to rule out bradycardia incrementally as the sensitivity level is lowered while decreasing a chance of over sensing T-waves.

The process described in connection with FIG. 9A is computationally inexpensive as it uses simple operations (such as comparisons, additions, multiplications and moving averages). Therefore, the process of FIG. 9A can be implemented efficiently in a power-constrained platform and thus may be implement on multiple platforms (e.g., ICM device, local external device or cloud server). Also, performance on the various multiple platforms could be mirrored with a high degree of agreement. By way of example, a limited number of control parameters may be designed and tested to be hard-coded or self-learned from EGM signal strips without user input.

The process of FIG. 9A uses an existing CA signal recorded but adds an ability to dynamically adjust sensing thresholds based on features of the CA signal, such as R, T and P-wave amplitudes and amplitude variability. The process of FIG. 9A also uses iterative processing to search for under-sensed bradycardia beats by lowering the sensing threshold up to the adaptive sensitivity limit.

A performance of the process of FIG. 9A was developed/tested on training and test data sets of 6541 and 996 episodes collected from field devices. The process of FIG. 9A exhibited an improvement of positive predictive value to >99% and >88%, improvement of relative sensitivity >99% and >96% and reduction of false detection rate of >99% and >95% in bradycardia and asystole, respectively, relative to conventional ORI processes.

IV. Alternative Embodiment—R-Wave Detection Using Self-Adjusting Parameters and Physiologic Discriminators ($1^{st}$ & $2^{nd}$ Pass)

Today, conventional ORI processes are programmed at the time of implant or manufacture, with the parameters for the ORI process remaining fixed throughout the useful life of the ICM. In conventional ORI processes, the ORI parameters are not automatically re-programmable and are not easily reprogrammed by a clinician. Opportunities remain to improve upon conventional ORI processes.

While the conventional ORI process provides high accuracy to sense intra-cardiac R-wave signals, an opportunity remains to improve upon the conventional ORI process. For example, an opportunity remains to improve upon the conventional algorithm in a manner that is less dependent on variations in skin contact with the sensing electrodes. As the interface varies between the sensing electrodes and the patient's subcutaneous tissue, the variation may influence the CA signal. In addition, the sensed CA signal may be affected by the nature of far field sensing and/or posture changes. In practice, the conventional ORI process exhibits good sensitivity with positive predictive value. However, an opportunity remains to reduce a rate of false positive detections of bradycardia and asystole episodes, thereby reducing the amount of false positive detections to be reviewed at the clinic.

In accordance with embodiments herein, systems and methods are described to improve detection of features of interest from a CA signal (e.g., R-wave peak) by performing a sequence of processing steps, while using features of the CA signal to calibrate sensitivity parameters of the R-wave detection process. Embodiments herein render the sensitivity profile parameters of the R-wave detection process adaptive, such that as the noise level changes, the parameters are adapted. For example, the sensitivity profile parameters may adjust how high or how low initial sensitivity levels are set, adjust the sensitivity limit and the like. In addition, various physiologic/noise discriminators are utilized to further handle unmitigated noise and under sensed events. In addition, adaptive sensitivity parameter settings are provided to self-adjust thresholds for varying signals and to perform R-wave peak sensing.

In accordance with embodiments herein, a computer implemented method is provided for detecting arrhythmias in cardiac activity. The method comprises, under control of one or more processors configured with specific executable instructions, obtaining a far field cardiac activity (CA) data set that includes far field CA signals for beats; identifying a T-wave characteristic of interest (COI) and an R-wave COI from the CA signals; adjusting profile parameters of a sensitivity profile based on the T-wave COI and R-wave COI, the sensitivity profile defining a time-varying sensitivity level and a sensitivity limit; automatically iteratively analyzing a beat segment of interest by: comparing the beat segment of interest to the time-varying sensitivity level to determine whether an R-wave is present within the beat segment of interest; and detecting an arrhythmia within the beat segment of interest based on a presence or absence of the R wave; and recording results of the detecting of the arrhythmia.

Additionally or alternatively, the identifying and adjusting operations are performed on a beat by beat basis. Additionally or alternatively, the method further comprises identifying, in connection with the R-wave COI, a rise rate of a current beat and determining whether the rise rate of the current beat exceeds a rise rate of a preceding beat by more than a R-wave rise rate threshold. Additionally or alternatively, the method further comprises adjusting at least one of a start sensitivity parameter that defines a start sensitivity of the sensitivity profile. Additionally or alternatively, the method further comprises identifying, in connection with the T-wave COI and R-wave COI, at least one of a rapid rise characteristic, a rapid heart rate characteristic, T/R-wave ratio characteristic or a T-wave-to-refractory proximity characteristic. Additionally or alternatively, the method further comprises adjusting, based on the T-wave COI and R-wave COI, at least one of a refractory period duration, decay delay period, start sensitivity, decay rate, or sensitivity limit parameter, the start sensitivity parameter defining a start sensitivity of the sensitivity profile, the refractory period duration parameter defining a blanking interval, a decay rate parameter defining a slope of a linear time-varying sensitivity level decline, the sensitivity limit parameter defining a lowest sensitivity level that linear sensitivity decline is not allowed to go below. Additionally or alternatively, the identifying, adjusting and analyzing operations are performed, by at least one of a local external device and a remote server, as a second pass confirmation for an arrhythmia episode declared by a first pass arrhythmia detection algorithm implemented by an implantable device. Additionally or alternatively, the CA data set includes device documented markers in combination with the CA signals, the CA data set generated by the implantable device in connection with the first pass arrhythmia detection algorithm, the first pass arrhythmia detection algorithm declaring the arrhythmia episode to be one of a bradycardia, tachycardia, asystole or atrial fibrillation episode.

Additionally or alternatively, the method further comprises adjusting the sensitivity limit based on amplitude of the CA signal during prior non-ventricular segments. Additionally or alternatively, the method further comprises applying a feature enhancement function to the CA signals to form an enhanced feature in the CA data set, wherein the applying the feature enhancement function enhances at least one of an R-wave feature, T-wave feature, P-wave feature and suppresses noise. Additionally or alternatively, the method further comprises overlaying a search window onto a current beat segment of the CA signals and determining whether the current beat segment contains noise signature, and based thereon retaining or removing the current beat segment from the CA signals. Additionally or alternatively, the method further comprises determining a signal to noise ratio (SNR) for the current beat segment, comparing the SNR with a threshold that corresponds to a non-physiologically high noise level, the identifying comprising labeling the current beat segment contains noise signature based on the comparison of the SNR to a threshold. Additionally or alternatively, the method further comprises determining an energy content of the current beat segment in the search window, comparing the energy content with a threshold range that corresponds to a non-physiologically high noise level, the identifying comprising labeling the current beat segment to represent a beat segment contains noise signature based on the comparison of the energy content to a threshold. Additionally or alternatively, the method further comprises determining a derivative of the current beat segment in the search window, comparing the derivative with a threshold that corresponds to a non-physiologically high noise level, the identifying comprising labeling the current beat segment to represent a beat segment contains noise signature based on the comparison of the derivative to a threshold. Additionally or alternatively, the method further comprises identifying a current beat segment that has a sensitivity level of interest within the CA signals; labeling the current beat segment as a beat segment of interest; identifying a sinus segment located proximate to the beat segment of interest; comparing the sinus and beat segment of interest; and declaring the beat segment of interest to represent an under sensed segment, asystole segment or bradycardia segment based on the comparing operation.

In accordance with embodiments herein, a system is provided for detecting arrhythmias in cardiac activity. The system comprises: memory to store specific executable instructions; and one or more processors configured to execute the specific executable instructions for: obtaining a far field cardiac activity (CA) data set that includes far field CA signals for beats; identifying a T-wave characteristic of interest (COI) and an R-wave COI from the CA signals; adjusting profile parameters of a sensitivity profile based on the T-wave COI and R-wave COI, the sensitivity profile defining a time-varying sensitivity level and a sensitivity limit; automatically iteratively analyzing a beat segment of interest by: comparing the beat segment of interest to the time-varying sensitivity level to determine whether an R-wave is detected within the beat segment of interest; and detecting an arrhythmia within the beat segment of interest based on a presence or absence of the R-wave; and recording results of the detecting of the arrhythmia.

Additionally or alternatively, the processor is configured to perform the identifying and adjusting operations on a beat by beat basis. Additionally or alternatively, the processor is further configured to identify, in connection with the R-wave COI, a rise rate of a current beat and determining whether the rise rate of the current beat exceeds a rise rate of a preceding beat by more than a R-wave rise rate threshold. Additionally or alternatively, the processor is further configured to adjust at least one of a start sensitivity parameter that defines a start sensitivity of the sensitivity profile. Additionally or alternatively, the processor is further configured to identify, in connection with the T-wave COI and R-wave COI, at least one of a rapid rise characteristic, a rapid heart rate characteristic, T/R-wave ratio characteristic or a T-wave-to-refractory proximity characteristic. Additionally or alternatively, the processor is further configured to adjust, based on the T-wave COI and R-wave COI, at least one of a refractory period duration, start sensitivity, decay rate, or sensitivity limit parameter, the start sensitivity parameter defining a start sensitivity of the sensitivity profile, the refractory period duration parameter defining a blanking interval, a decay rate parameter defining a slope of a linear time-varying sensitivity level decline, the sensitivity limit parameter defining a lowest sensitivity level that linear sensitivity level decline is not allowed to go below. Additionally or alternatively, the processor is further configured to confirm or deny at least one of a bradycardia episode based on a number of X beats within a bradycardia zone out of a total of Y beats within the CA data set. Additionally or alternatively, the processor is further configured to confirm or deny an asystole episode when the beat segment of interest exhibits no detected electrical activity for a period of time that exceeds an asystole threshold. Additionally or alternatively, the system further comprises an implantable medical device housing the processor and memory. Additionally or alternatively, the processor and memory are housed within at least one of a local external device and a remote server. Additionally or alternatively, the processor is further configured to adjust the sensitivity limit based on amplitude of the CA signals during prior non-ventricular, segments.

As one non-limiting example, the processes described in connection with FIGS. 9B and 9C have been modeled with respect to the conventional ORI process (described in connection with FIG. 8B) that utilizes fixed parameters to define automatic sensing control (ASC). The internal modelling utilized a random dataset of field events that included a total of 996 EGM signal data strips, each of which included a 30 second recording of cardiac activity recorded by a commercially released ICM. The processes of FIGS. 9B and 9C achieved a reduction of false events by >84%, as compared to a convention ORI detection process. Also the processes of FIGS. 9B and 9C herein maintained a >93% relative sensitivity, as compared to the conventional ORI detection process, for both bradycardia and asystole episodes.

Figure 10A:
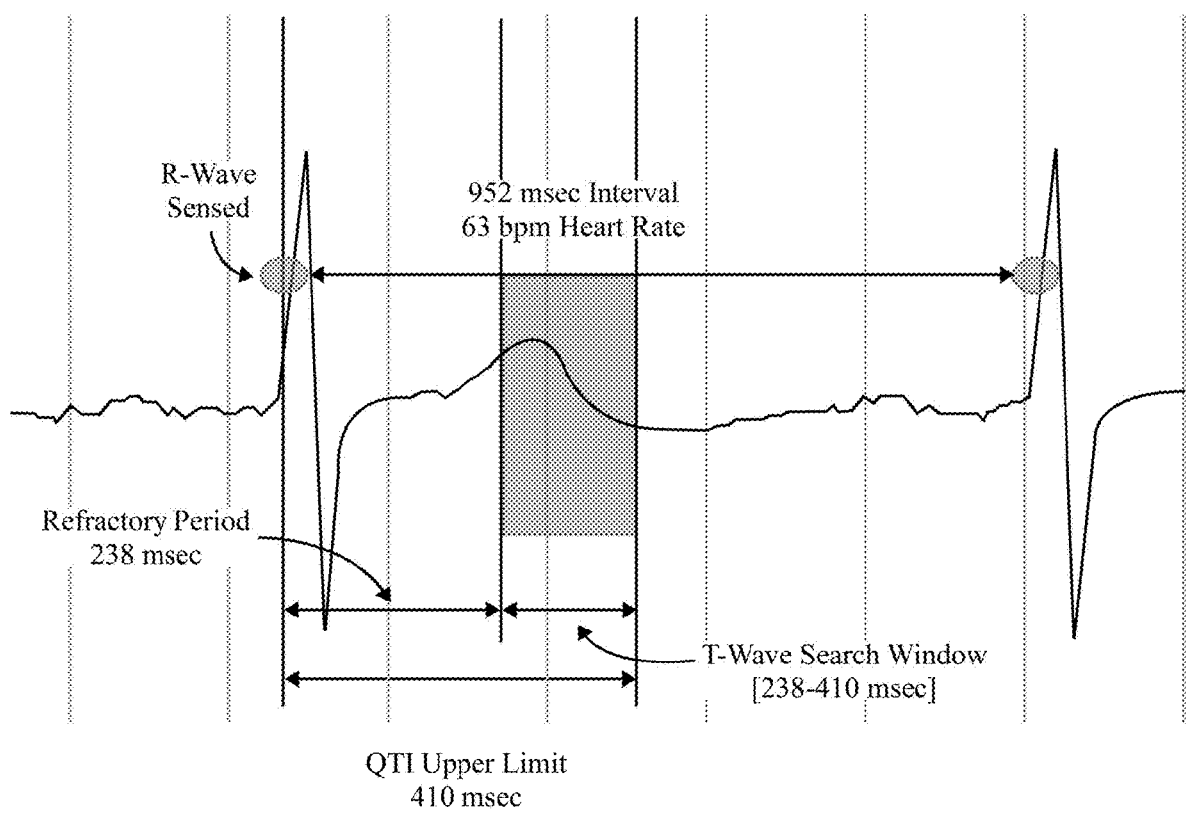
FIG. 10A illustrates an example for identifying T-wave peak amplitude in accordance with embodiments herein.
Figure 10B:
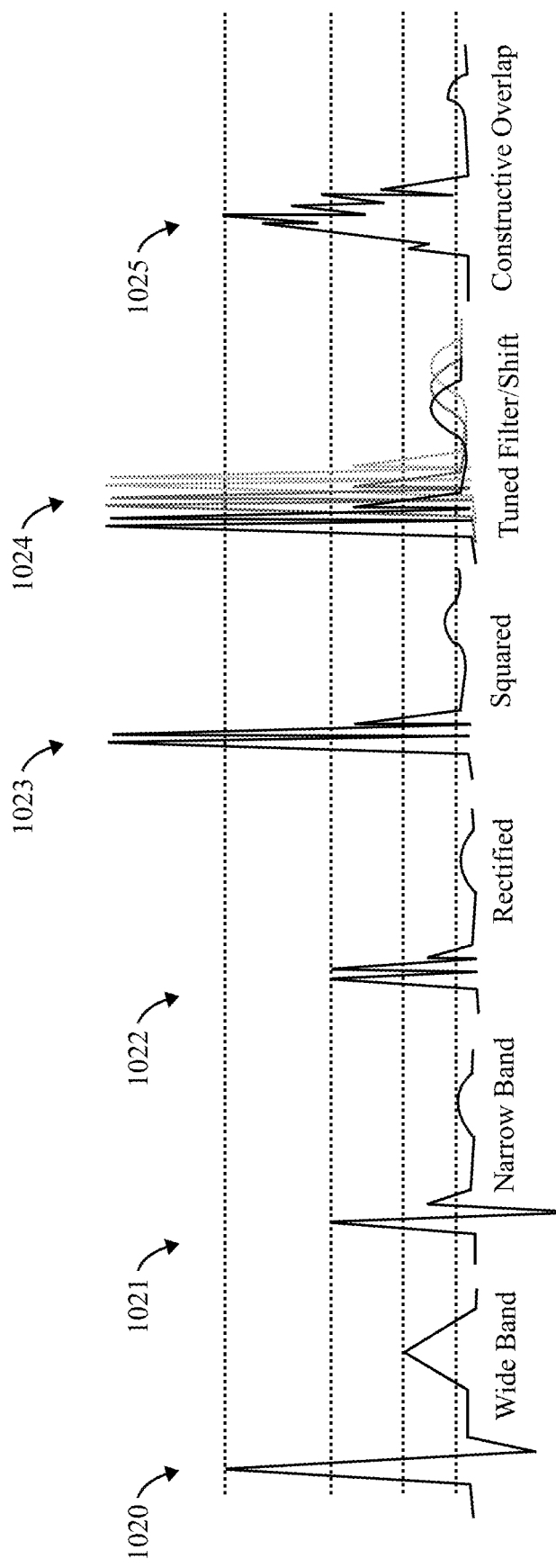
FIG. 10B illustrates examples of signals produced at the various feature enhancement operations within FIG. 9A in accordance with embodiments herein.

FIG. 9B illustrates a process for R-wave detection in accordance with embodiments herein. The process of FIG. 9B will be described in connection with FIG. 10B. FIG. 10B illustrates examples of signals produced at the various operations within FIG. 9B. The operations at 948-952 apply a feature enhancement function to the CA signals to form enhanced R-wave features in the CA data set.

At 948, the one or more processors bandpass filter and rectify the CA signals. The CA signals may be obtained from various sensing channels of the ICM. For example, the CA signals may be collected over the VEGM sensing channel and/or the VSENSE sensing channel. The bandpass filter may be implemented as a hardware or software filter that is configured with desired passband coefficients (e.g., passband 8 to 35 Hz). For example, the bandpass filter may represent a digital finite impulse response filter. The bandpass filter is applied to the CA signals to suppress frequency bands that do not contribute to a feature of interest. For example, the bandpass filter may be configured to maintain peaks of the R-wave, while suppressing lower-frequency components (e.g., T-waves, P-waves and baseline isoelectric) and suppressing high-frequency components (e.g., myopotential noise). At 948, the one or more processors also apply a hardware or software rectifier to the bandpass filtered signal in order to change signal components of negative polarity to positive polarity to form a modified CA signal that represents a rectified bandpass filtered CA signal. The rectified band-pass filtered CA signal splits the energy of the signal into multiple side peaks with smaller amplitudes relative to the original CA signal.

In FIG. 10B, a wide band CA signal 1020 is illustrated as an example segment for one cardiac beat. The wide band CA signal 1020 is filtered to provide a narrow band CA signal 1021 and then rectified to form a rectified bandpass filtered CA signal 1022.

Returning to FIG. 9B, at 949, the one or more processors apply a feature enhancement function to the CA signals to form an enhanced feature of interest in the CA data set. For example, the processors may first compare the modified CA signal to a lower boundary threshold (e.g., 1 unit of an analog to digital converter). Segments of the modified CA signal that fall below the lower boundary threshold represent noise, while segments of the modified CA signal that exceed the lower boundary threshold may include "potential" or "candidate" features of interest. The one or more processors may apply a mathematical enhancement function to the segments of the CA signal that exceed the lower boundary threshold. For example, the processors may apply a square function to the segments of the CA signal that exceed the lower boundary threshold, in order to increase separation between peaks and non-peaks in the CA signals. The operation at 949 generates an "enhanced" modified CA signal that includes an enhanced feature of interest (e.g., enhanced R-wave feature). As shown in FIG. 10B, the operation at 949 converts the rectified CA signal 1022 to a squared CA signal 1023.

At 950, the one or more processors apply a further feature enhancement function to the CA signal, namely a moving filter to successive windows of the modified "squared" CA signal to further enhance the COI. The window width and the filter coefficients may be adjusted/tuned based on a duration of previous peaks identified in prior segments of the current or a prior CA data set. For example, when the operations of FIG. 9B operate upon a 30 second segment of the CA data set, the window width and filter coefficients may be tuned based on a prior CA data set for a different 30 second segment of CA signals. Additionally or alternatively, the window width and filter coefficients for a second segment of the CA signal (e.g., a middle or later 5 second segment) may be tuned based on a first or prior segment of CA signals (e.g., a first or earlier 5 second segment). The window width and filter coefficients are defined such that the peak (R-wave) is further enhanced apart from non-R-wave peak features. For example, a QRS segment, having a duration of 80 msec, may be copied a select number of times (e.g., copied 2 times) and aligned with one another in a temporally shifted manner. For example a first copy of the 80 msec CA signal segment may be shifted −80 msec with respect to the original 80 msec CA signal segment, while the original CA signal segment is maintained with a 0 msec shift, and a second copy of the CA signal segment may be shifted +20 msec with respect to the original CA segment. The copies and original CA signal segments are constructively added to produce higher separation between the R-wave peak and a remainder of the signal content of the CA segment. As shown in FIG. 10B, the shifted signal 1024 is formed and then constructively added to form a constructive overlapping CA signal 1025.

The foregoing signal conditioning operations at 948-950 provide a feature enhancement to the CA signals to form enhanced features of interest with an increased signal-to-noise ratio. In particular, the feature enhancement increases the separation between the R-wave peak and the peaks of the T-wave, P-wave and isoelectric segment. Additionally or alternatively, the operations at 948-950 may correlate the CA signal segment with an M-shaped template similar in shape to the rectified signal. The operations at 948-950 provide constructive coherence to amplify the divided R-peak while leaving the dome shaped T-waves and P-waves around the same amplitude as in the original CA signal.

Optionally, at 951, the one or more processors may determine whether to combine a select combination of the CA signals processed in different manners to form modified CA signals. When signals are to be combined, flow moves to 952, otherwise flow continues to 953. At 952, the one or more processors form a combination (e.g., by addition) of wide-band, narrow band, rectified and/or derived signals (e.g., by differentiation or integration operators) to form the modified CA signals. Various combinations of the signals may be combined in order to produce larger separation between features of interest and background signals, thus increasing the signal-to-noise ratio. The modified CA signal (from 951 or from 952) is then utilized for analysis for physiologic/noise discrimination as discussed hereafter.

In accordance with the foregoing, the operations at 948-952 apply a feature enhancement function to the CA signals to form an enhanced feature of interest in the CA data set.

Next, the operations at 953-958 identify one or more beat segment of interests within the CA data set. At 953-956, the one or more processors apply physiologic/noise discrimination on successive beat segments. The beat segments may overlap or extend contiguous with one another. At 953, the one or more processors overlay a search window over the modified CA signal, where the search window has a duration corresponding to a multi-beat segment. The length of the search window (and multi-beat segment) may vary, provided that the search window encompass a desired number of beats sufficient to enable the process to characterize the number of beats as physiologic or non-physiologic. Next the process may branch along one or more of multiple alternative or parallel paths that apply various criteria to determine whether the beats within the search window represent a stable or beat segment of interest.

At 954C, the one or more processors determine a signal to noise (SNR) ratio for the CA signal segments in the search window. At 955C, the one or more processors compare the SNR ratio for the CA signal for the current beat segment within the search window with a threshold that is selected to correspond to a non-physiologically high noise level. The threshold may be defined in various manners. As one example, the threshold may define a percentage of a dynamic range of the CA signals. For example, the noise should not exceed 15%, 25%, etc. of the dynamic range for the current beat segment within the search window. Alternatively, at least 75%, 85%, etc. of the signal content for the current beat segment within the CA signals should be classified as "signal", not noise. At 955C, if the SNR is below the threshold, flow branches to 956 as the process deems the signal quality unsuitable, and thus labels the current beat segment to represent an beat segment of interest. Otherwise, at 955C, if the SNR is above the threshold, the process deems the signal quality suitable, and thus labels the current beat segment to represent a stable beat segment and flow branches to 957.

Additionally or alternatively, flow branches from 953 to 954B. At 954B, the one or more processors determine energy content or integral for the CA signals of the current beat segment within the search window. At 955B, the one or more processors compare the energy content (or integral) for the CA signals for the current beat segment with energy threshold that is selected to correspond to a non-physiologically high energy level. The energy threshold may be defined in various manners. At 955B, if the energy content is above the energy threshold, flow branches to 956 as the process deems the signal quality unsuitable and the beat segment un-analyzable. Otherwise, at 955B, if the energy content is below the physiological energy threshold, the process deems the signal quality suitable, and includes beat segment in analysis and flow branches to 957.

Additionally or alternatively, flow branches from 953 to 954A. At 954A, the one or more processors determine a maximum slope or derivative for the CA signal of the current beat segment within the search window. At 955A, the one or more processors compare the maximum slope or derivative for the CA signal segments in the current beat segment with a derivative range. The derivative threshold may be defined in various manners. The derivative threshold may be an upper threshold and/or a lower threshold that define non-physiologically high and/or low derivatives for the CA signal. For example, a non-physiologically high derivative may occur due to motion artifacts, or a non-physiologically low derivative may occur for an extended period of time, such as due to partial or complete loss of skin contact at one or more electrodes. At 955A, if the maximum derivative of the CA signal segment is above or below the derivative threshold(s), flow branches to 956 as the process deems the signal quality unsuitable, and the beat segment un-analyzable. Otherwise, at 955A, if the maximum derivative is within the derivative threshold, the process deems the signal quality suitable, and thus labels the current beat segment to represent a stable beat segment and flow branches to 957. Additionally or alternatively, the operations at 954A, 955A may analyze other aspects of the CA signals, such as the average maximum derivative between positive and negative CA signal peaks, a number of slope changes in the CA signals, sum of absolute slopes of the CA signal in an interval and the like.

The decisions at 955C, 955B and 955A may be independently used to determine whether the beats within the current beat segment exhibit non-physiologic characteristics, thereby representing analyzable beat segments that should be retained or warrant removal from the modified CA signals. Optionally, a combination of the decisions from the operations at 955C, 955B and 955A may be utilized as a physiologic-noise discriminator to indicate the presence of noise sufficient to deem the signal quality of the current beat segment unsuitable for further signal analysis.

When flow advances from one or more of 955C, 955B, 955A and 956, the one or more processors remove one or more beats of the current beat segment from the modified CA signals to provide a physiologically discriminated CA signal (also referred to as a physiologically discriminated CA data set). Optionally, the number of beats or portion of the CA signals that is removed at 956 may vary based on the determinations at 955C, 955B, and/or 955A. For example, when the SNR is below the threshold (at 955C), but the integral and derivative comparisons are outside the associated thresholds (at 955B and 955A), then one or a small number of beats may be removed from the current beat segment at 956. Alternatively, when the SNR, integral and derivative are all outside the corresponding thresholds (at 955C, 955B, 955A), then the entire current beat segment may be removed.

At 957, the one or more processors determine whether the analysis has reached the end of the modified CA signals. If so, the process ends at 958. If additional modified CA signals remain to be analyzed, flow moves to 958. At 958, the search window is shifted to a "next" beat segment within the CA signals. The next beat segment may partially overlap the prior beat segment, or be entirely separate from the prior beat segment. The shift at 958 may be a programmed duration (e.g., X msec), a programmed number of beats (e.g., 1-9 beats), a full length of the search window or another amount.

Figure 10C:
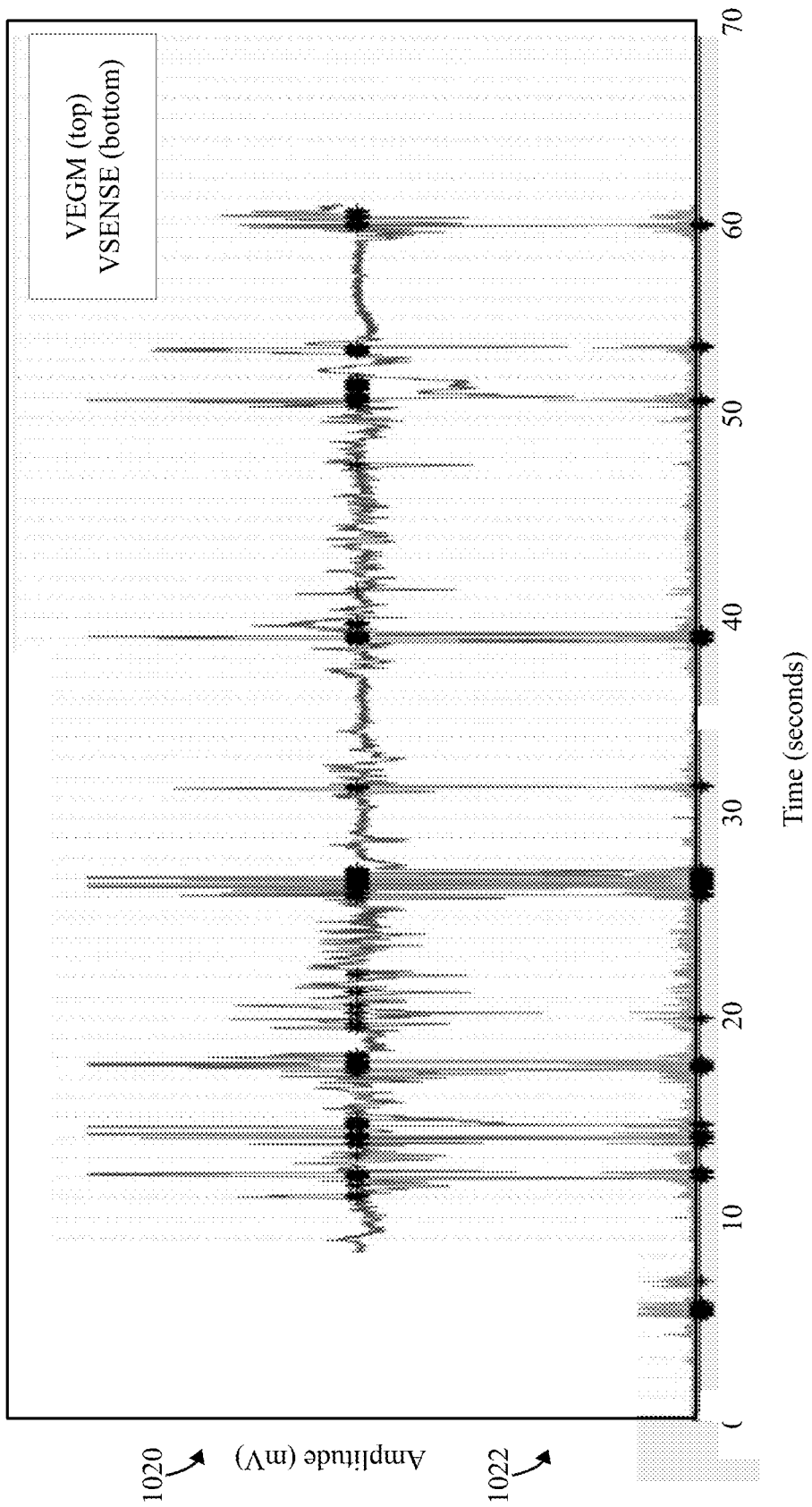
FIG. 10C illustrates CA signals collected in connection with a wide-band (VEGM) sensing channel and a narrow-band (VSENSE) sensing channel and analyzed in connection with the processes for FIG. 9B in accordance with embodiments herein.

FIG. 10C illustrates CA signals 1020, 1022 collected in connection with a wide-band (VEGM) sensing channel and a narrow-band (VSENSE) sensing channel, respectively. The CA signal 1020 for the VEGM sensing channel and/or the CA signal 1022 for the VSENSE sensing channel are analyzed based on the process of FIG. 9B, and one or more beats of the CA signals 1020 and/or 1022 are removed to provide a physiologically discriminated CA signal and physiologically discriminated CA data set. In FIG. 10C, the beats that are removed are denoted by circular markers or asterisks along the baseline.

Figure 9C:
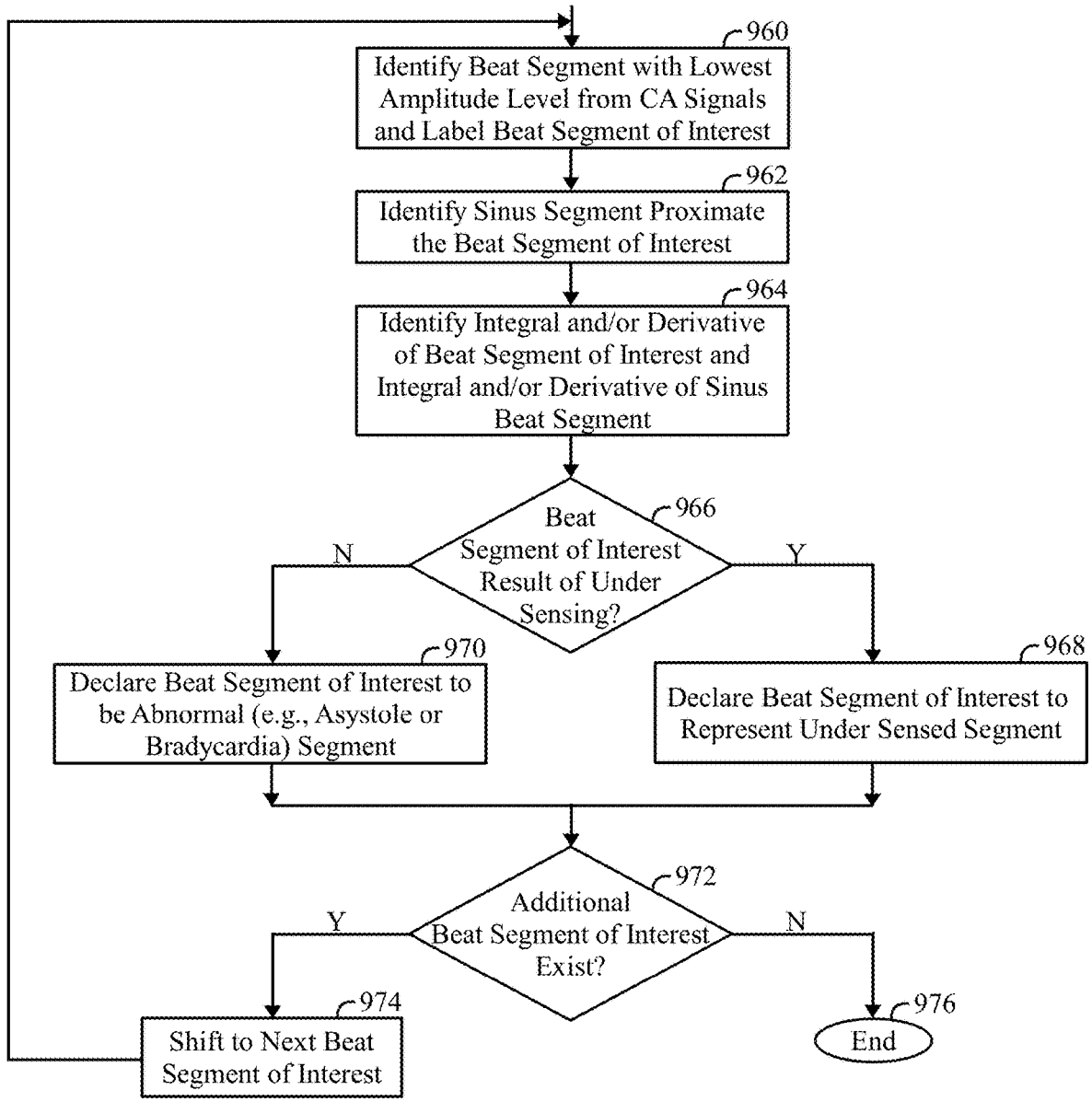
FIG. 9C illustrates a process for confirming or denying a device documented bradycardia or asystole episode in accordance with embodiments herein.

FIG. 9C illustrates a process for confirming or denying a device documented bradycardia or asystole episode in accordance with embodiments herein. False determinations of bradycardia or asystole episodes may occur when an ICM experiences variations between high and low sensitivity levels in connection with sensing CA signals. When the sensitivity varies between high and low levels, the CA signal will also exhibit beat segments having similar variations between high and low signal amplitudes. When one or more beat segments exhibit a low sensitivity level, the beat segment is considered to represent a "suspect" beat segment. The process of FIG. 9C utilizes signal integrals and/or signal derivatives to analysis "suspect" beat segments that potentially experience under sensing. As explained hereafter, the process of FIG. 9C generally compares a "suspect" beat segment, that potentially experiences under sensing, with one or more other beat segments having a desired (e.g., higher) sensitivity level. The comparison is utilized to confirm or deny bradycardia and/or asystole episodes.

At 960, the one or more processors identify the beat segment that has a sensitivity level of interest (e.g., the lowest sensitivity level) within the modified CA signal. The processors label the identified beat segment as a suspect beat segment. The suspect beat segment may be identified in various manners. For example, the sensitivity level for a beat segment may correspond to the SNR determined at 954C in connection with FIG. 9B for each of the beat segments. When the SNR (determined at 954C) is utilized, the processors at 960 review each SNR and identify the lowest SNR. The beat segment having the lowest SNR is labeled as the suspect beat segment.

Additionally or alternatively, at 960, the one or more processors may apply an additional or separate analysis to identify a sensitivity limit of each of the successive beat segments of the modified CA signal. The number of beats within one beat segment is defined by a search window that is overlaid onto the CA signals. The length of the search window (and beat segment) may vary, provided that the search window encompass a desired number of beats sufficient to enable the process to identify a sensitivity limit for each beat segment. The sensitivity limit for any given beat segment may be defined in various manners. For example, the sensitivity limit may be defined based on a dynamic range of the modified CA signals during a corresponding beat segment.

At 962, the one or more processors identify a sinus segment that is located proximate to the suspect beat segment. For example, the sinus segment may correspond to a beat segment that immediately precedes the suspect beat segment or precedes the suspect beat segment by a predetermined number of beats or amount of time. A beat segment may be characterized as "a sinus segment" in various manners, such as when the beat segment exhibits greater amplitude signals than the suspect beat segment, amplitudes that are greater than the suspect beat segment by a predetermined amount or amplitudes that exceed a programmed level. Additionally or alternatively, the sinus segment may be defined based on other criteria. For example, the sinus segment may be defined to correspond to a beat segment preceding or following the suspect beat segment, where the candidate sinus segment has an SNR, integral/energy and/or derivative (as determined at 954C, 954B and 954A) that satisfies the corresponding threshold.

At 964, the one or more processors identify the integral and/or derivative of the CA signals within the suspect beat segment. The one or more processors also identify the integral and/or derivative of the CA signals within the sinus segment. At 966, the integral and/or derivative of the suspect beat segment is compared to the integral and/or derivative of the sinus segment. For example, the comparison at 966 may determine whether the segments of the suspect and sinus signals are similar or within a predetermined range of one another. Additionally or alternatively, the comparison at 966 may determine whether the derivatives of the suspect and sinus signals are similar or within a predetermined range of one another. When the integrals and/or derivatives are sufficiently similar, flow moves to 968. Alternatively, with the integrals and/or derivatives differ by a predetermined amount, flow moves to 970.

At 966, the one or more processors determine whether the suspect beat segment results from an under sensed segment or whether the suspect beat segment indicates an arrhythmia (e.g., a presence of bradycardia or asystole). The processors determine whether under sensing occurred based on a comparison of the integrals and/or derivatives of the suspect and sinus segments. The processors may determine at 966 that a bradycardia or asystole episode does not exist where the integrals and/or derivatives of the suspect and sinus segments are within predetermined ranges of one another.

At 968, the one or more processors declare the suspect beat segment to represent an under sensed segment and to remove the suspect beat segment from the modified CA signals that may be further analyzed. By removing the suspect beat segment, as an under sensed segment, the process of FIG. 9C avoids false detection of unstable beats (e.g., bradycardia and asystole episodes).

At 970, the one or more processors declare the suspect beat segment to be an arrhythmia (e.g., asystole or bradycardia segment). The suspect beat segment may be declared a bradycardia segment based on bradycardia criteria, while the suspect beat segment may be declared an asystole segment when the segment satisfies asystole criteria. For example, the bradycardia criteria may be that X bradycardia beats occurred out of Y total beats. As another example, the asystole criteria may be that a predetermined period of time has passed without any device detected activity in the CA signal.

Optionally, the processors may perform the bradycardia and/or asystole analysis at 970 to perform the declaration. Alternatively, the suspect beat segment may already have been declared a potential bradycardia segment or asystole segment at an earlier point in the process. When the suspect beat segment is already declared a potential bradycardia or asystole segment, at 970, the processors merely confirm the prior determination.

Figure 10D:
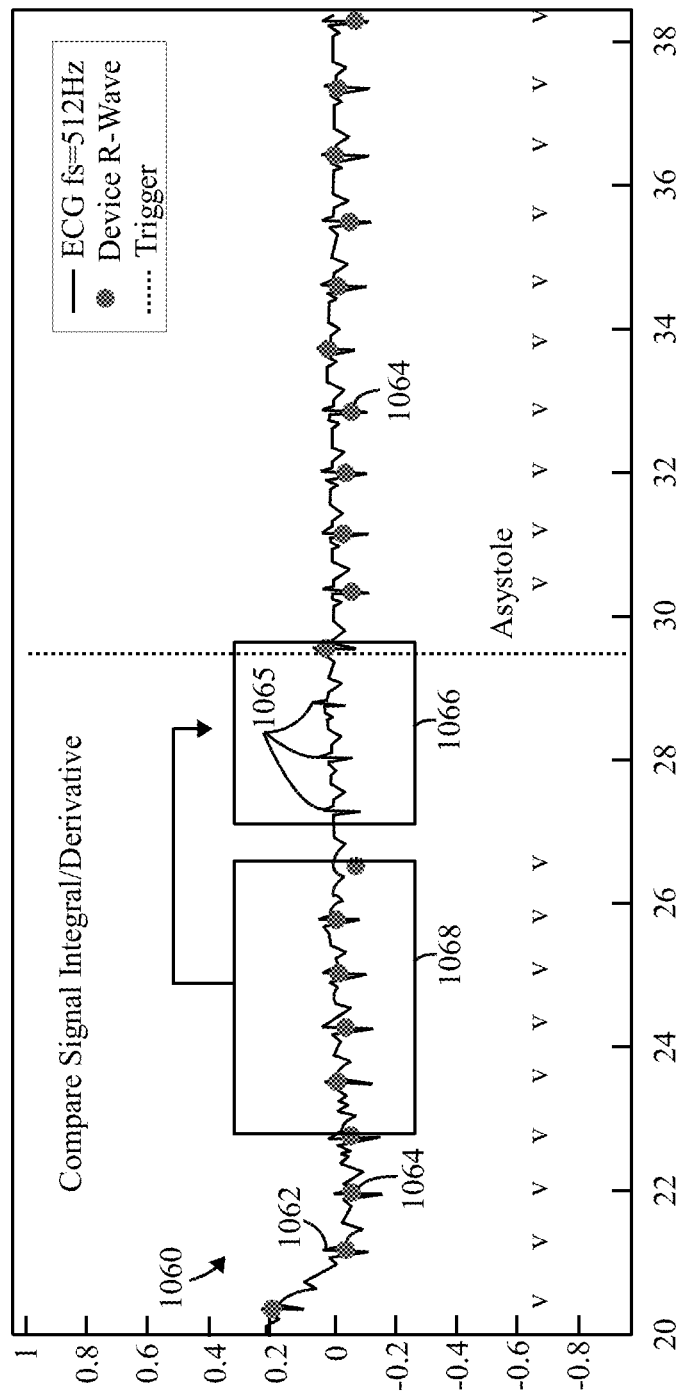
FIG. 10D illustrates an example of a CA signal that is analyzed in connection with the process of FIG. 9B in accordance with embodiments herein.

FIG. 10D illustrates an example of a CA signal that is analyzed in accordance with the process of FIG. 9C. In FIG. 10D, the CA signal 1060 includes a series of cardiac events or beats 1062, from which the ICM has identified device detected R-waves denoted by R-wave marker 1064 (e.g., a dot) superimposed upon the cardiac events. The ICM has also declared one or more beats 1065 to be non-sinus (e.g., asystole). In accordance with the operations of FIG. 9C, a beat segment that has the lowest sensitivity level within the modified CA signal is identified and labels as a suspect beat segment 1066. The sinus segment 1068 is identified as located proximate to the suspect beat segment 1066. For example, the sinus segment 1068 may correspond to a beat segment that precedes the suspect beat segment 1066 by a predetermined number of beats or amount of time. The process of FIG. 9C identifies whether the integral and/or derivative of the suspect beat segment 1066 is similar to the integral and/or derivative of the sinus segment 1068. The false asystole detection at 1065 is "ruled out" or rejected when the integral and/or derivative of the suspect and sinus segments 1066 and 1068 are within predetermined ranges of one another.

Returning to FIG. 9C, following 968 and 970, at 972, the one or more processors determine whether additional suspect beat segments were declared in the CA signals. If so, flow moves to 974, where the process shifts to the next suspect beat segment. Otherwise, the process ends at 976.

Figure 10E:
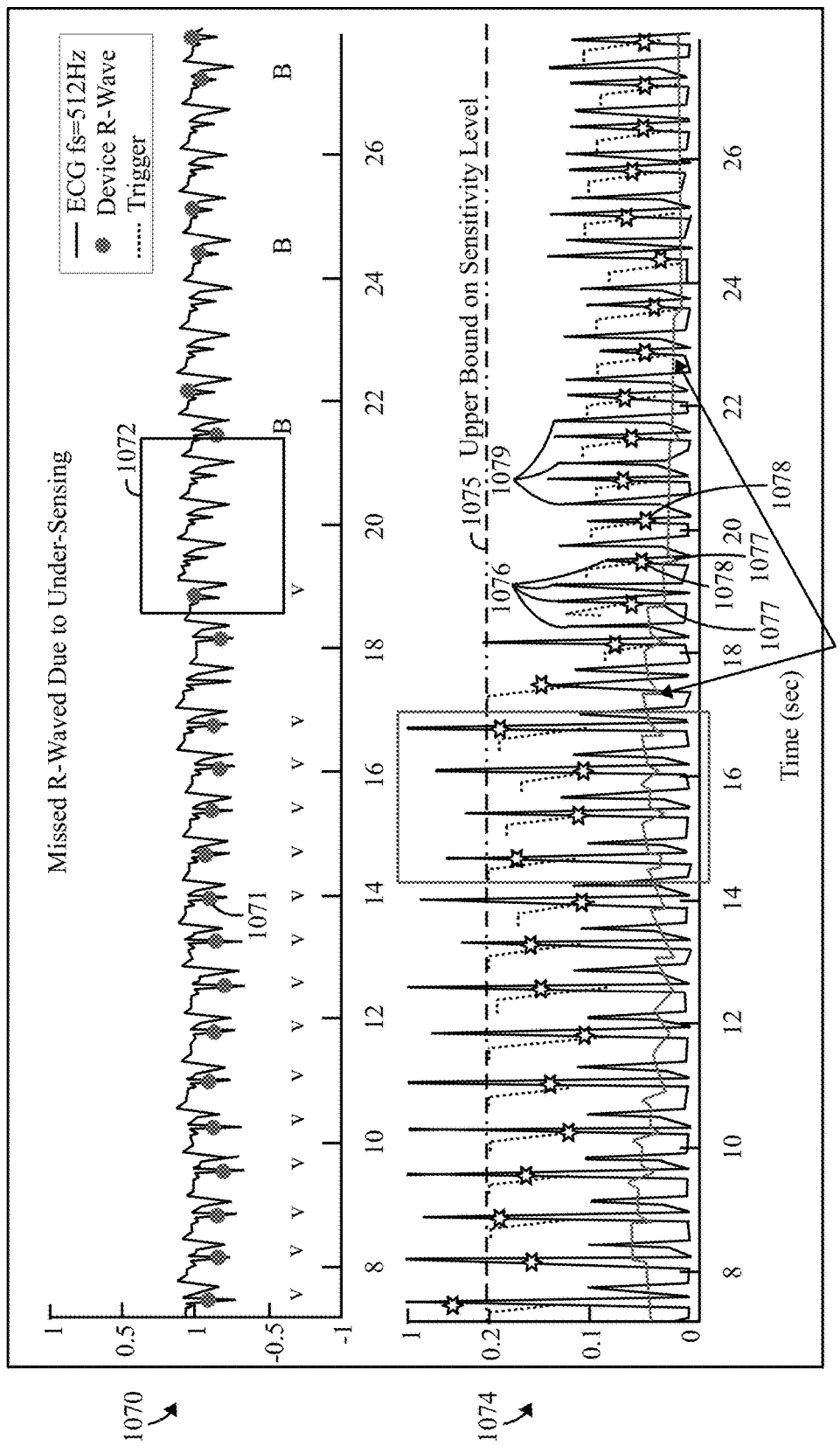
FIG. 10E illustrates an example of CA signals analyzed by a process for setting upper and lower bounds on sensitivity levels in connection with the processes for FIG. 9D in accordance with embodiments herein.

FIG. 10E illustrates an example of CA signals analyzed by a process, in accordance with an embodiment herein, for setting upper and lower bounds on sensitivity levels. In FIG. 10E, a CA signal 1070 is illustrated with markers 1071 detected by an ICM in accordance with a conventional ORI process. As noted by beat segment 1072, the conventional ORI process fails to detect certain R-waves due to under-sensing. FIG. 10E also illustrates a modified CA signal 1074 that is formed by processing the original CA signal 1070 in accordance with embodiments herein that apply feature enhancement to form enhanced R-wave features. The modified CA signal 1074 is also analyzed to identify beat segments of interest and to calculate upper and lower sensitivity bounds based on the enhanced R-wave features. The upper and lower bounds on sensitivity levels are calculated based on the enhanced R-wave features from and immediately preceding R-wave, not simply based on prior stable beats. An upper boundary (minimum sensitivity) is defined at 1075. The process herein adjust the upper bound of sensitivity level based on a group of prior successive R-wave peak amplitudes. For example, peak amplitudes of R-waves 1076 are used to define the upper sensitivity level during successive beats as noted at 1075. By applying the feature enhancement to enhanced R-wave features and the adaptive lower bound on sensitivity level, the embodiment associate with FIG. 10E detects R-waves (as noted at markers 1078 during the suspect beat segment 1072).

In accordance with the processes of FIGS. 9B and 9C, the adaptive sensitivity level is bound by a lower bound 1077 that varies with non-ventricular signal 1078 (outside both R-wave 1076 and T-wave 1079 intervals). For example, the lower sensitivity bound is calculated as mean+2 standard deviation of CA signal in the preceding non-ventricular interval. Utilizing upper and lower sensitivity bounds protects against over-sensing on noise or large P-waves, while allowing sensitivity to go lower during periods of small R-waves.

As explained herein, a conventional R-wave sensing algorithm adjusts a time-varying sensing level based on a sensitivity profile illustrated in FIG. 2B, for which the control parameters are fixed (e.g., refractory period duration, threshold start percentage, decay delay duration, lower bound or maximum sensitivity, etc.). Turning to FIG. 2B, the start sensitivity threshold parameter 161 defines a start level of the sensitivity profile 153. For example, the start sensitivity parameter may set a start sensitivity to a percentage of the preceding R-wave peak amplitude. The refractory period duration parameter 159 defines a blanking interval beginning at a sensed R-wave 155, during which the processors do not search for CA signal. When the profile includes a linear sensitivity level decline 153, the decay delay rate defines a slope of the linear sensitivity level decline. The maximum sensitivity parameter 157 defines a lowest sensitivity level (e.g., maximum sensitivity) that linear sensitivity decline is allowed to reach. The decay delay parameter 169 defines the interval at which the sensitivity profile maintains the sensitivity level at a constant level following expiration of the refractory period before the sensitivity profile begins decreasing.

Although a physician can reprogram the values, in the conventional R-wave sensing algorithm, there is no self-learning based on real time CA signal features. Also, the conventional R-wave sensing algorithm discussed herein does not consider T-wave amplitude information. The foregoing limitations of the conventional R-wave sensing algorithm may lead to unintended under-sensing or over-sensing under abrupt change in signal morphology, amplitude, and heart rate.

Figure 9D:
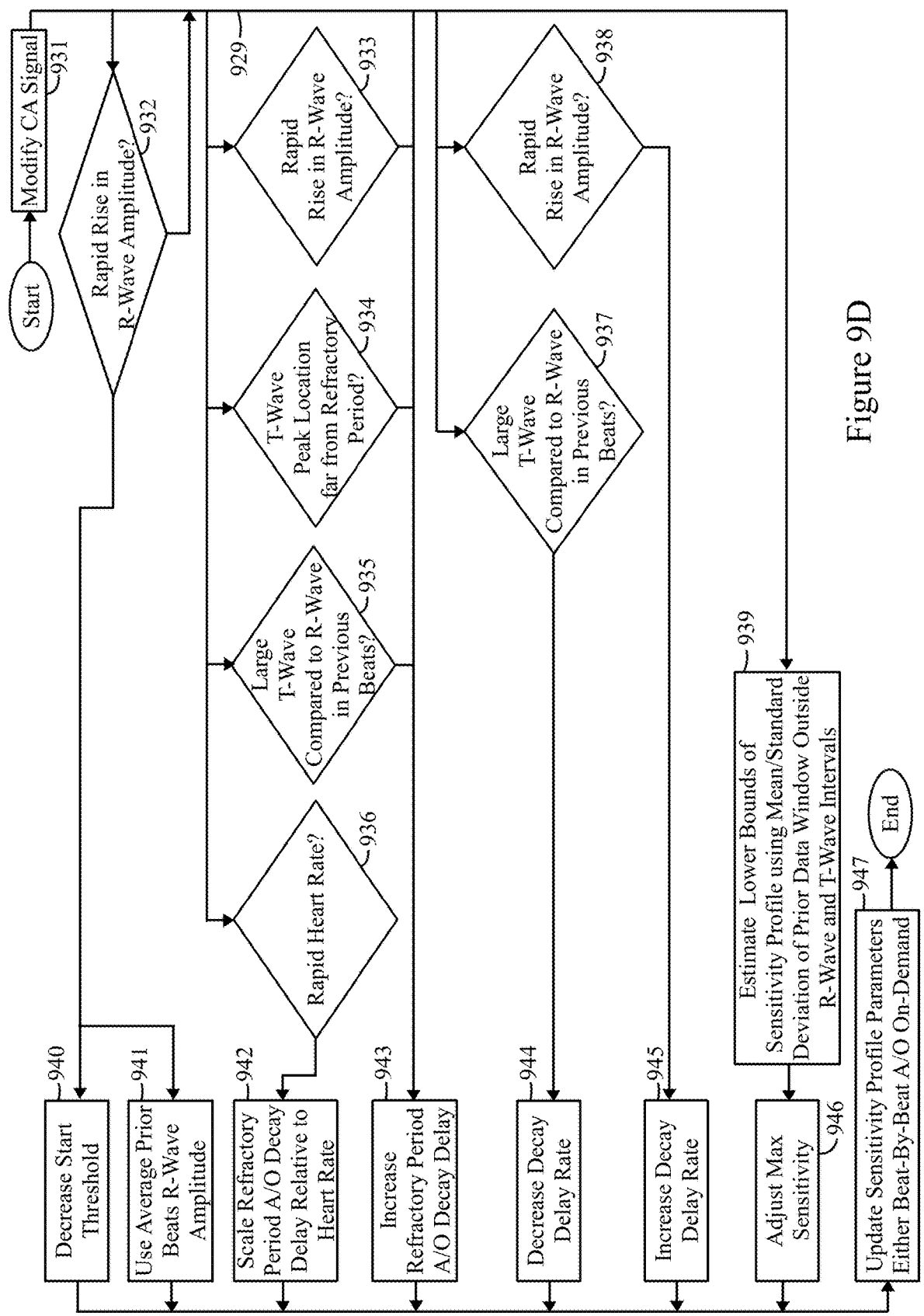
FIG. 9D illustrates a process for adaptively adjusting the sensitivity profile parameters beat by beat (or ensemble by ensemble) based on R-wave and T-wave characteristics of interest in accordance with embodiments herein.

The process of FIG. 9D adaptively adjusts the sensitivity profile beat by beat (or ensemble by ensemble) based on R-wave and T-wave characteristics of interest. The process of FIG. 9D follows multiple parallel determinations along the parallel paths at 929, to dynamically adjust parameters of the sensitivity profile (e.g., start threshold, refractory period, decay delay, decay delay rate and max sensitivity)

At 931, the one or more processors obtain a CA signal for a beat and/or ensemble of beats. At 932, the one or more processors identify a rise rate of the current beat/ensemble and determine whether the current R-wave rise rate exceeds an R-wave rise rate of a preceding beat/ensemble by more than a R-wave rise rate threshold. If so, the current R-wave has a "rapid rise rate characteristic". The R-wave rise rate threshold may be calculated based on an R-wave rise rate of an individual prior beat and/or an ensemble of prior beats. Alternatively, the R-wave rise rate threshold may be predetermined (e.g., clinician programmed). A newly sensed R-wave will have a much larger R-wave rise rate compared to prior beats when a PVC occurs. When the difference between the current and prior R-wave rise rates exceed a certain threshold, flow moves to 940. Otherwise, the process does not update any parameters of the sensitivity profile based on the decision at 932. Regardless of the determination at 932, flow continues along the parallel branch 929. At 940, the one or more processors modify a start sensitivity parameter that defines a start sensitivity of the sensitivity profile. For example, the start sensitivity parameter may set start sensitivity to a percentage of the preceding R-wave peak amplitude (e.g., 75% of the peak of the preceding R-wave). At 940, the processors reduce the start sensitivity parameter to a lower percentage value of the R-wave peak amplitude (e.g., reduce from 75% to 50%). Alternatively, flow branches to 941, where the processors may retain the start sensitivity percentage at the same level, but instead the processors set the start sensitivity as the predetermined percentage of the average peak amplitude for an ensemble of prior beats.

Next, the discussion concerns the operations at 933-936, where the one or more processors analyze R-wave and T-wave characteristics of interest (COI) in connection with modifying a refractory period and/or decay delay parameter of the sensitivity profile. At 933, the one or more processors determine whether the current beat/ensemble exhibits "a rapid rise rate characteristic" in the R-wave that exceeds an R-wave rise rate threshold in the same manner as discussed above at 932. When a rapid rise characteristic is identified, flow continues to 943. Otherwise, the process does not update any parameters of the sensitivity profile based on the determination at 933.

At 934, the one or more processors determine whether the current beat/ensemble exhibits a T-wave peak having a proximity to the R-wave sensing refractory period, that exceeds a T-wave refractory threshold. If so, flow moves to 943. Otherwise, no sensitivity profile parameters are updated based on T-wave refractory proximity. If the separation between the T-wave peak location and the end of R-wave sensing refractory period in prior beats is greater than the T-wave—refractory threshold (e.g., 100 msec), at 943, the processors increase the refractory period by a predetermined amount (e.g., 50 msec) in order to avoid T-wave over-sensing in future beats.

At 935, the one or more processors determine whether the current beat/ensemble exhibit a T-wave peak amplitude, relative to the R-wave amplitude, that exceeds a T/R-wave amplitude ratio threshold. If so, flow moves to 943. Otherwise, no sensitivity profile parameters are updated based on the T/R-wave amplitude ratio. The processors may assess the T-wave amplitude in previous beats by searching for the peak amplitude in a T-wave search window that is temporally positioned after the sensed R-wave. FIG. 10A illustrates an example for identifying T-wave peak amplitude. FIG. 10A illustrates a CA signal, for which an R-wave is detected. Following detection of the R-wave, a refractory period is set (e.g., 238 ms). Following the refractory period, a T-wave search window is defined having a predetermined duration. For example, the duration of the T-wave search window may represent the difference between the Q-T interval (QTI) upper limit (e.g., 410 ms) and the refractory. The processors analyze the CA signal within the T-wave search window to identify a peak of the T-wave. Alternatively, the T-wave search window could be heart rate dependent. With reference to FIG. 10A, first an upper limit of the Q-T interval is calculated. The T-wave search window will start from [QTI_limit –refractory period] to [QTI_limit], with both values set relative to the timing of a sensed R-wave. Once the peak T-wave is found, the processors register the T-wave peak amplitude and time relative to the sensed R-wave.

Returning to FIG. 9D, at 935, if the T/R wave amplitude ratio exceeds a threshold (e.g., T-wave amplitude/R-wave amplitude>=0.8) in prior beats, at 943, the processors increase the refractory period parameter of the sensitivity profile (e.g., T-wave peak time+20 msec) in order to avoid T-wave over-sensing.

Additionally or alternatively, at 943, the processors may increase the decay delay parameter.

At 936, the one or more processors determine whether the current beat/ensemble exhibits a "fast heart rate characteristic", whereby the heart rate exceeds a heart rate threshold (e.g., 100 bpm). When the heart rate exceeds the heart rate threshold, flow moves to 942. At 942, the one or more processors scale the refractory period parameter and/or scale the decay delay parameter relative to the heart rate. For example, with a fast heart rate, the processors may decrease the refractory period parameter based on a scaling factor to avoid under-sensing. For example, the processors may set the refractory period=250 msec*(base rate/current heart rate), where the base rate=60 bpm. If it is assumed that the current heart rate is 100 bpm, then the new refractory period will be 150 msec. The processors may scale the decay delay in a similar manner based on a desired decay delay scaling factor. Alternatively, when the heart rate is not declared to be rapid, no sensitivity profile parameters are updated based on a fast heart rate characteristic.

At 937, the one or more processors determine whether the current beat/ensemble exhibit a T-wave peak amplitude, relative to the R-wave amplitude, that exceeds a T/R-wave amplitude ratio threshold. If so flow moves to 944. The processors perform a T-wave amplitude search similar to the process described above for adjusting refractory period. When the T/R wave amplitude ratio (T-wave amplitude divided by R-wave amplitude) is greater than 0.5, the processors decreases the decay delay rate parameter (e.g., use a lower mV/msec decay delay speed) in order to avoid T-wave over-sensing. For example, the processors may decrease the decay delay rate parameter by 0.5 uU/msec at every 5% increase in the T/R wave amplitude ratio.

At 938, the one or more processors determine whether the R-wave rise rate exceeds an R-wave rise rate threshold. If so, flow moves to 945 where the processors increase the decay delay rate parameter for the sensitivity profile. When the newly sensed R-wave (such as a PVC beat) has much larger amplitude R-wave compared to prior beats, the processors use higher decay delay speed to avoid under-sensing of the next beat.

At 939, the one or more processors estimate a lower bound for the time-varying sensitivity profile. For example, the processors may set the lower bound for the time-varying sensitivity profile to be scaled sum of a mean and standard deviation of non-ventricular portions of the CA signals for a desired number of beats. The non-ventricular portions correspond to portions of the beats that are outside of the R-wave and the T-wave intervals. For example, the processors may overlay a search window (e.g., 2 seconds) over non-ventricular activity portions of the CA signals prior to a current beat. The processors calculate a mean/standard deviation values for the non-ventricular activity portions of the CA signals outside the R-wave and T-waves to estimate the lower bound of the time-varying sensitivity profile (e.g., as mean+2*standard deviation). During beats of decreased background noise or small P-waves, the lower bound of the sensitivity profile would decrease, while during beats of increased background noise or large P-waves, the lower bound of the sensitivity profile would increase.

At 946, the one or more processors adjust the lower bound of sensitivity, such as adjusting the maximum sensitivity to be utilized in the sensitivity profile.

At 947, the one or more processors update the sensitivity profile parameters that were adjusted at 940-946. The process of FIG. 9D adjusts one or more of the sensitivity profile parameters on a beat-by-beat basis. Additionally or alternatively, adjustment may be done on a regular time (e.g., every 1 minute) or on-demand when specific conditions are met. The process of FIG. 9D will track the beat-by-beat changes in heart rate, R-wave amplitude, and T-wave amplitude, and adjust sensitivity profile parameters only when abrupt changes of interest occur in the CA signal. It is recognized that somewhat similar operations may be performed at different points in the process of FIG. 9D. For example, at 933 and 938, the one or more processors analyze R-wave amplitudes for a rapid rising characteristic. As another example, at 935 and 97, the one or more processors compare a ratio between T-wave and R-wave amplitudes. When similar operations are performed at different points in the process of FIG. 9D, the same or different thresholds may be utilized. For example, a common or different rapid rise thresholds may be utilized at 933 and 938, and a common or different T/R wave ratio thresholds may be utilized at 935, 937. In addition, it is recognized that the adjustments at 940-946 may adjust a common parameter in complementary or counteracting/subtractive manners. For example, at 943 and 945, the process may increase the decay delay rate parameter, while the operation at 944 may decrease the decay delay rate parameter. The amount of increase or decrease in each parameter at each of 940-946 may vary.

The process of FIGS. 9A-9D was tested on a data set of 996 episodes collected from field devices and found to perform superior to a conventional ORI process. The process of FIGS. 9B and 9C exhibited improvement of positive predictive value to 88%, improvement of relative sensitivity 93% and reduction of false detection rate of 84% in bradycardia and asystole, respectively, as compared to the conventional ORI process.

The process of FIGS. 9B and 9C is computationally inexpensive as it uses simple operations (such as comparisons, additions, multiplications and moving averages) that can be implemented efficiently in power-constrained platform and thus may be implemented on multiple platforms (e.g., ICM device, local external device or cloud server) and performance on these multiple platforms could be mirrored with very high degree of agreement.

The processes for FIGS. 9A, 9D afford the ability to dynamically adjust arrhythmia detection parameters and thresholds based on previous history preceding a suspected detection such as by adjusting refractory period, starting threshold, maximum sensitivity lower bound and T-wave amplitude. The processes for FIGS. 9A-9C provide unique and simple ways to detect un-physiologic segments of data to avoid false detections on low quality data, and may be applied on a secondary channel, a primary channel or combination thereof.

Additionally or alternatively, the processes of FIGS. 3, 4, 9A-9D may be implemented partly in firmware of the ICM, while the remaining operations are implemented off-line on an external device or remote server. As a further example, the operations of FIGS. 3, 4, 9A-9D may be divided in other manners between the ICM, an external device and/or remote server.

As another example implementation, the process of FIGS. 3, 4, 9A-9D may be implemented in a cloud-based environment, such as on a remote server and/or distributed between multiple remote processors/servers. For example, a remote server at a medical network may receive CA data sets generated by an ICM. The remote server may analyze the CA data sets off-line, such as in an effort to identify false positive AF detections that are declared by the ICM. The remote server may collect multiple CA data sets and, perform batch type processing to analyze multiple CA data sets at one point in time. A remote server or cloud-based network provides substantial computational power well in excess of what would be needed to efficiently process even a large batch of episode electrograms. Hence, a remote server or cloud-based network would afford better R-wave detection and improved arrhythmia discrimination for AF episodes before the CA data sets are presented to a clinician, thereby removing or substantially reducing the amount of time required by a clinician to parse through false positives and distinguish true arrhythmias from false arrhythmias.

Additionally or alternatively, the processes of FIGS. 3, 4, 9A-9D may be implemented on a local external device, such as a smart phone, tablet device or other device in the possession of the patient. Mobile devices such as smart phones are configured with a ICM application configured to communicate with the ICM. The mobile devices are capable of processing CA data sets as described herein. The mobile device may make a determination, based on the enhanced R-wave detection processes described herein, whether an episode represents a true arrhythmia or instead a false positive driven by inappropriate R-waves. The mobile device may screen out the false positive episodes and prevent the false positive episodes from being uploaded to the remote server. Additionally or alternatively, the mobile device may also provide feedback communication to the ICM (e.g., informing the ICM of the false positives) to allow the ICM to update diagnostic counts that are maintained therein.

In accordance with at least some embodiments, one or more processors herein may identify that the set of device declared R-waves (as designated by the ORI process in the ICM) significantly differs from the confirmation R-waves identified in connection with the process of FIGS. 3, 4, 9A-9D. When substantial differences are identified, the one or more processors may send an alert to a clinician to check and/or reprogram sensitivity parameters. Optionally, a "simulated ORI" process may be implemented to analyze a CA data set offline (e.g., in the cloud) upon detection of such different sets of R-waves. The simulated process may test one or more potential ORI configurations and identifies an improved set of device-programmable ORI parameters to decrease the "false-positive burden" at the ICM. Optionally, the improved ORI programming parameters may be automatically pushed back to remotely program the ICM. Applied more broadly to a sufficiently long CA data set (up to and including the entirety of 24-hour monitoring), the R-wave detection processes herein can provide detailed ventricular rhythm diagnostics.

V. Alternative Embodiment—Fully Adaptive R-wave Detection/Correction Algorithm ($1^{st}$ & $2^{nd}$ Pass)

In accordance with embodiments herein, a computer implemented method is described for detecting arrhythmias in cardiac activity. The method comprises, under control of one or more processors configured with specific executable instructions, obtaining a far field cardiac activity (CA) data set that includes far field CA signals for a series of beats; i) applying an initial R-wave detection process to the CA signals and designating R-wave markers in the CA data set, the R-wave markers separated by RR intervals; ii) applying an R-wave confirmation process that comprises: ii)(a) calculating instantaneous and average RR intervals between the R-wave markers designated by the initial R-wave detection process; ii)(b) identifying a suspect beat segment from the CA signals based on a relation between the instantaneous and average RR intervals; ii)(c) searching the suspect beat segment for a potential under detected beat by comparing the suspect beat segment to one or more QRS templates; and ii)(d) when an under detected beat is identified from the suspect beat segment, designating a new R-wave marker within the CA data set corresponding to the under detected beat; iii) detecting an arrhythmia within CA data set based on the R-wave markers designated during the initial R-wave detection process and R-wave confirmation process; and iv) recording results of the detecting of the arrhythmia.

Additionally or alternatively, the method may further comprise analyzing the relation between the instantaneous and average RR intervals, wherein the instantaneous and average RR intervals are identified by stepping through successive beat segments along the CA signal to search for potential under detected beats, the instantaneous RR interval representing an interval between a current R-wave marker and one of a preceding and succeeding R-wave marker, the average RR interval representing an average interval for a predetermined number of RR intervals related to a current RR interval. Additionally or alternatively, the relation utilized to identify the suspect beat segment represents a difference between the instantaneous and average RR intervals that exceeds an RR interval range threshold. Additionally or alternatively, the identifying the suspect beat segment further comprising overlaying a search window on a current beat segment and comparing i) the instantaneous RR interval for a current beat within the search window and ii) the average RR interval corresponding to a collection of beats within the search window, the comparison being performed while iteratively stepping the search window through the CA signals beat by beat. Additionally or alternatively, the method, further comprises building a library of QRS templates based on morphologies of beats detected in the CA signals; identifying a current QRS segment from the CA signals; comparing the current QRS segment to the library of QRS templates; when the current QRS segment does not match the QRS templates, adding a new QRS template to the library based on the current QRS segment. Additionally or alternatively, the method further comprises identifying a time of peak amplitude in the suspect beat segment and designating a candidate R-wave marker at the time of peak amplitude; calculating a candidate RR interval between the candidate R-wave marker and a previous R-wave marker; comparing the candidate RR interval to an RR interval threshold indicative of an actual RR interval; and when the new RR interval falls below the RR interval threshold, declaring the candidate R-wave marker to be false and that no under detection occurred. Additionally or alternatively, the method further comprising searching for an R-wave within the CA signal based on a signal envelope and local maxima; when the R-wave is detected, set a refractory period during which no additional R-waves are searched; and following termination of the refractory, searching for a next R-wave within a corresponding next signal envelope. Additionally or alternatively, the method further comprising adjusting a duration of the refractory interval based on the RR interval and T-wave peak location of the previous beats. Additionally or alternatively, the method further comprising applying a feature enhancement to the CA signals to form enhanced R-wave or T-wave features in the CA data set.

In accordance with alternative embodiments, a system is provided for detecting arrhythmias in cardiac activity. The system comprises: memory to store specific executable instructions; and one or more processors configured to execute the specific executable instructions for: obtaining a far field cardiac activity (CA) data set that includes far field CA signals for a series of beats; applying an initial R-wave detection process to the CA signals and designating R-wave markers in the CA data set, the R-wave markers separated by RR intervals; applying an R-wave confirmation process. The R-wave confirmation process comprises: calculating instantaneous and average RR intervals between the R-wave markers designated by the initial R-wave detection process; identifying a suspect beat segment from the CA signals based on a relation between the instantaneous and average RR intervals; searching the suspect beat segment for a potential under detected beat by comparing the suspect beat segment to one or more QRS templates; and when an under detected beat is identified from the suspect beat segment, designating a new R-wave marker within the CA data set corresponding to the under detected beat. The one or more processors are further configured for detecting an arrhythmia within CA data set based on the R-wave markers designated during the initial R-wave detection process and R-wave confirmation process; and recording results of the detecting of the arrhythmia.

Additionally or alternatively, the processor is further configured to analyze the relation between the instantaneous and average RR intervals, wherein the instantaneous and average RR intervals are identified by stepping through successive beat segments along the CA signal to search for potential under detected beats, the instantaneous RR interval representing an interval between a current R-wave marker and one of a preceding and succeeding R-wave marker, the average RR interval representing an average interval for a predetermined number of RR intervals related to a current RR interval. Additionally or alternatively, the relation utilized to identify the suspect beat segment represents a difference between the instantaneous and average RR intervals that exceeds an RR interval range threshold. Additionally or alternatively, the processor is further configured to apply a feature enhancement to the CA signals to form enhanced R-wave or T-wave features in the CA data set. Additionally or alternatively, the processor is further configured to identify the suspect beat segment by overlaying a search window on a current beat segment and comparing i) the instantaneous RR interval for a current beat within the search window and ii) the average RR interval corresponding to a collection of beats within the search window, the comparison being performed while iteratively stepping the search window through the CA signals beat by beat. Additionally or alternatively, the processor is further configured to build a library of QRS templates based on morphologies of beats detected in the CA signals; identify a current QRS segment from the CA signals; compare the current QRS segment to the library of QRS templates; when the current QRS segment does not match the QRS templates, add a new QRS template to the library based on the current QRS segment. Additionally or alternatively, the processor is further configured to identify a time of peak amplitude in the suspect beat segment and designating a candidate R-wave marker at the time of peak amplitude; calculate a candidate RR interval between the candidate R-wave marker and a previous R-wave marker; compare the candidate RR interval to an RR interval threshold indicative of an actual RR interval; and when the new RR interval falls below the RR interval threshold, declare the candidate R-wave marker to be false and that no under detection occurred.

Additionally or alternatively, the processor is further configured to search for an R-wave within the CA signal based on a signal envelope and local maxima; when the R-wave is detected, set a refractory period during which no additional R-waves are searched; and following termination of the refractory, search for a next R-wave within a corresponding next signal envelope. Additionally or alternatively, the processor is further configured to adjust a duration of the refractory interval based on the RR interval and T-wave peak location of the previous beats. Next, a detailed description is provided for one or more methods and systems to implement the foregoing embodiments.

Figure 9E:
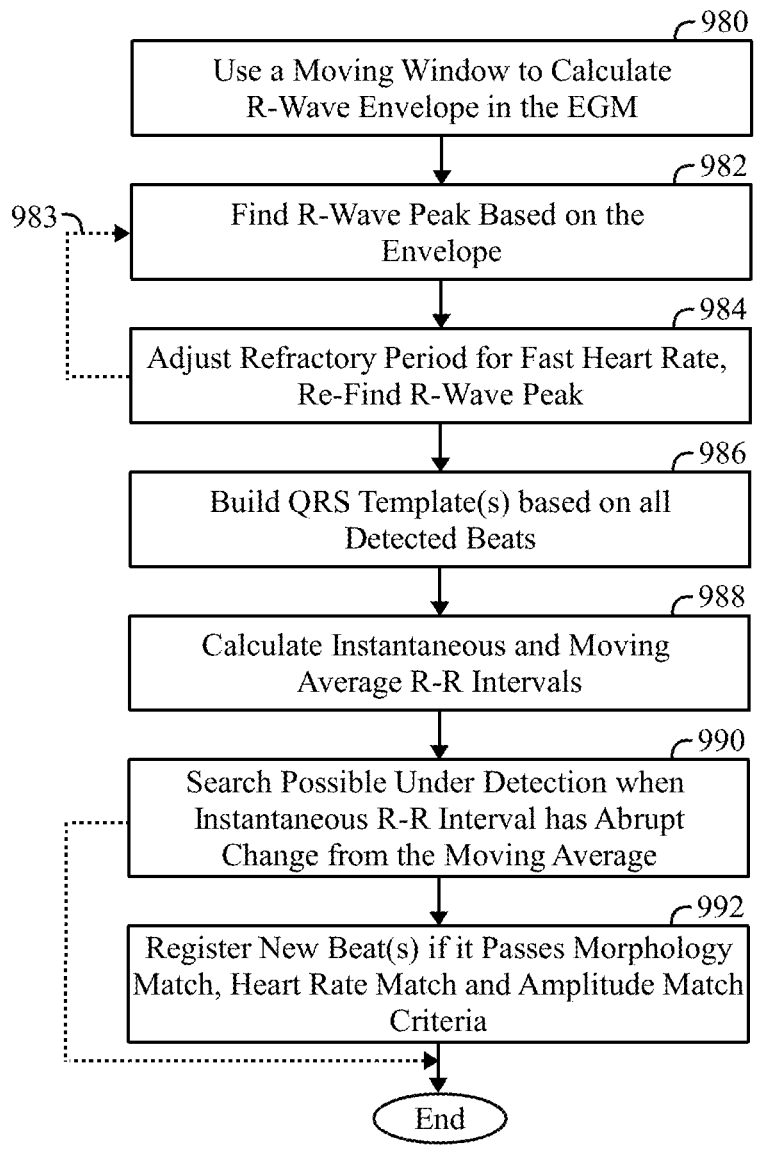
FIG. 9E illustrates a process for R-wave detection in accordance with embodiments herein.

FIG. 9E illustrates a process for R-wave detection in accordance with embodiments herein. Prior to the R-wave detection process of FIG. 9E, the one or more processors may bandpass filter and rectify the CA signals as explained elsewhere herein.

At 980, the one or more processors utilize a moving window to calculate an R-wave envelope for the CA signals. For example, the processors may apply a moving average filter (e.g., 90 second average). The moving average filter is used to calculate the signal envelope, from which a signal floor is determined. For example, the signal floor of the signal envelope may be defined as a percentile of the signal envelope profile (e.g., 2.5 percentile). Additionally or alternatively, when the signal floor is determined to be too low (e.g., below 0.05 mV), the processors may redefine the signal floor as a different percentile of the signal envelope (e.g., 25 percentile). For example, it may be desirable to adjust the signal floor, such as when the CA signal includes segments that have little or no activity for longer than the moving average window size.

Figure 10F:
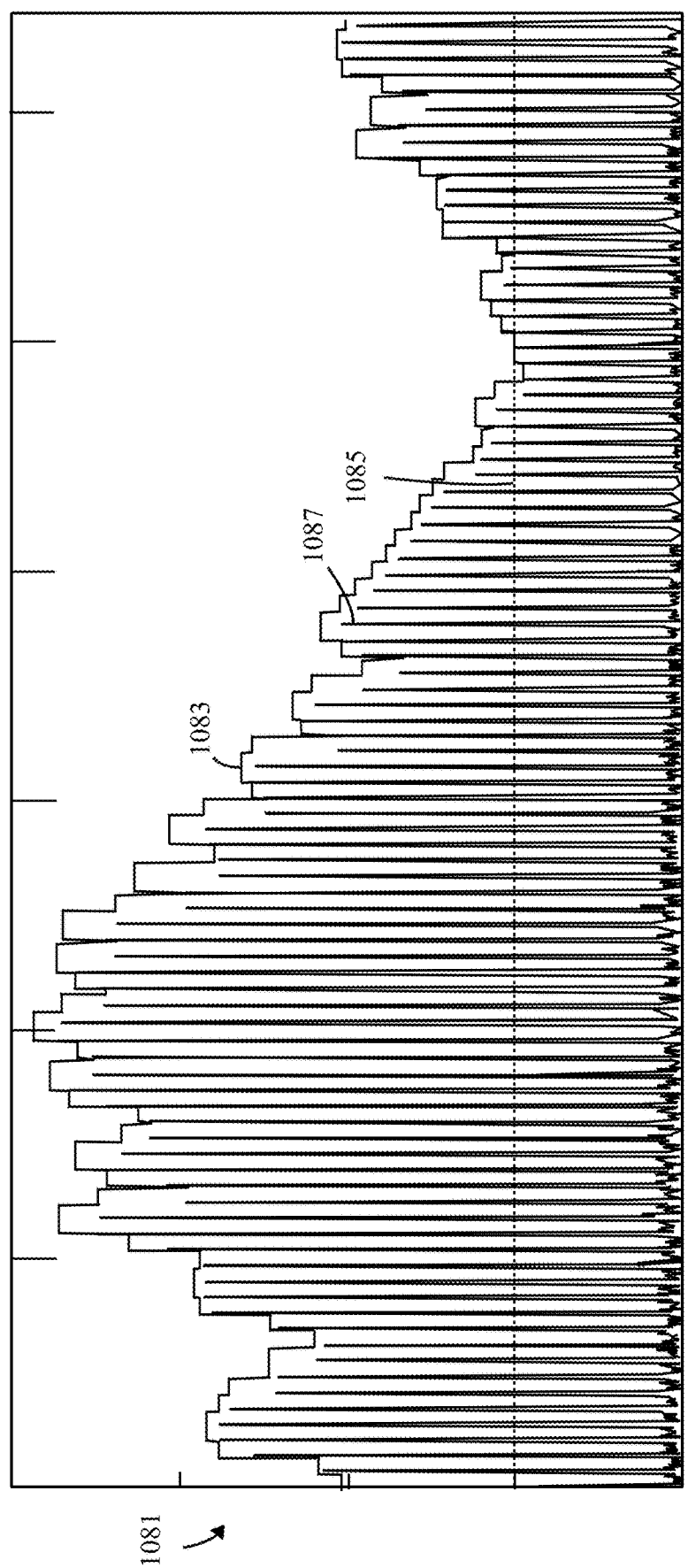
FIG. 10F illustrates a portion of a CA signal processed in accordance with the operation at in FIG. 9E in accordance with embodiments herein.

FIG. 10F illustrates a portion of a CA signal processed in accordance with the operation at 980 in FIG. 9E. FIG. 10F illustrates a filtered, rectified CA signal 1081, to which a feature enhancement function has been applied. A signal envelope 1083 is calculated by the moving average filter. Once the signal envelope 1083 is determined, the processors then define a signal floor 1085. The signal floor 1085 is defined to correspond to a predetermined percentile of the signal envelope 1083.

Returning to FIG. 9E at 982, the one or more processors search for R-waves within the CA signal. The processors apply a sensitivity threshold (e.g., 0.8 times the signal floor) to search local maxima greater than the sensitivity limit in the rectified CA signal and identify them as the R-waves. With reference to FIG. 10E, a local maxima 1087 is designated as the peak of an R-wave, the processors set a refractory period (e.g., 250 ms), during which the processors do not search for additional R-waves. When the refractory period terminates, the processors identify the next local maxima therein.

At 984, the one or more processors determine whether the refractory period should be adjusted, such as in connection with a fast heart rate. In connection therewith, the processors calculate R-R intervals (RRIs) for the R-waves detected at 982 and determine a statistical characteristic of interest related to the RRIs, such as the median. If the median RRI (or another statistical characteristic of interest) is outside of a predetermined limit (e.g., the median is less than 500 msec), the one or more processors adjust the refractory period (e.g., shorten it from 250 to 150 ms). The processors repeat the operation at 982 (as denoted by dashed line 983) in order to find new local maxima indicated R-waves based on a shorter refractory period (e.g., 150 msec). At 984, the processors obtain peak R-wave amplitudes for all or a portion of the beats that were detected. At 984, optionally, the one or more processors remove any R-waves that were detected within an initial introductory segment or within a final closing segment of the complete CA signal (e.g., the first second and the last second of the CA signal). The initial and final segments of the CA signals are removed in order to avoid boundary conditions that may otherwise affect subsequent operations described herein. The operations at 982-984 are repeated until the RRI have a statistical characteristic of interest that satisfies a predetermined limit. Thereafter, flow advances to 986.

At 986, the one or more processors build a library of QRS templates based on the beats detected at 982-984. In connection therewith, the processors apply a window (e.g., 100 msec window) to each beat of the CA signals wherein the window is set relative to a corresponding device documented R-wave marker. For example, a 100 ms window may be centered at the peak of the R-wave (corresponding to the device documented R-wave marker), where the processors capture pre- and post-R-wave CA signals to extract an individual QRS segment. The individual QRS segment is compared to QRS morphology templates already saved in the library. When the current QRS segment matches (or is substantially similar to) an existing QRS morphology template, the library does not need to be updated. Alternatively, when the current QRS segment differs from the QRS morphology templates in the library, a new QRS morphology template is formed based on the current QRS segment and is added to the library. The processors may utilize various criteria to determine whether a current QRS segment matches or differs from existing QRS morphology templates. For example, the processors may apply cross-correlation between the current QRS segment and one or more QRS morphology templates, where a result of the cross-correlation is compared with a match threshold (e.g., cross-correlation coefficient greater than 0.5, and/or cross-correlation peak is less than 20 msec.).

At 988, the one or more processors calculate instantaneous and average RR intervals based on sets of RR intervals for the CA signal. For example, the processors may calculate the instantaneous RR intervals as an interval between a current R-wave marker and a preceding R-wave marker and/or a current R-wave marker and succeeding R-wave marker. As another example, the processors may calculate an average RR interval by averaging a predetermined number of RR intervals related to a current RR interval (e.g., four of the most recent RRI values preceding a current R-wave marker).

At 990, the one or more processors step through successive beat segments along the CA signal to search for potential under detected beats. The processors identify potential under detection based on "abrupt" changes between instantaneous and moving averages for the RRI. For example, the relation utilized to identify the suspect beat segment may represent a difference between the instantaneous and average RR intervals that exceeds an RR interval range threshold. To search for differences outside the RR interval range threshold, the processors overlay a search window on a current beat segment (e.g., a single beat or a series of two or more beats). The processors compare i) the instantaneous RRI for the current beat within the search window and ii) the average RRI corresponding to a collection of beats within the search window. The processors perform the comparison while iteratively stepping the search window through the CA signals beat by beat. The processors designate potential under detected beats when the comparison exceeds certain limits. For example, the processors designate a potential under detected beats when the instantaneous RRI exceeds an initial limit and the instantaneous and average RRIs vary from one another by more than a predetermined amount. For example, when the instantaneous RRI is greater than 500 msec and the instantaneous RRI is greater than the average RRI by more than 100 msec, the processors may determine that a potential under detected beat has occurred within the suspect beat segment.

At 990, when a potential under detected beat is identified, the processors define a search window for the potential under detected beat. The search window is positioned between two successive detected R-waves. For example, the search window may begin a predetermined period of time after a previous detected R-wave and extend until a predetermined period of time before a next successive detected R-wave. For example, the processors may extract a suspect beat segment from the CA signal, where the suspect beat segment is searched for the potential under detected beat/R-wave. The suspect beat segment may begin 150 msec after the previous detected R-wave marker and continue up to 100 msec before the current R-wave marker. The processors compare the suspect beat segment to one or more QRS morphology templates within the library. For example, the comparison may be based on correlation (e.g., >0.5 correlation coefficient). If the suspect beat segment includes a shape that does not match, or is sufficiently different from, the QRS morphology templates, the processors determined that no under detection occurred and the operation at 992 is skipped. Alternatively, if the suspect beat segment matches or is sufficiently similar to a QRS morphology template, the processors determined that under detection did occur and flow moves to 992.

At 992, the one or more processors identify a time of peak amplitude in the suspect beat segment and temporarily designate a candidate R-wave marker at the time of peak amplitude as a candidate R-wave. The processors calculate a candidate RRI between the candidate R-wave marker and a previous R-wave marker (as detected at 982). The processors compare the new RR interval to an RR interval threshold that is defined as a shortest or lowest RR interval that is acceptable as an actual or legitimate RR interval. If the new RR interval falls below the RR Interval threshold, the new RR interval is considered too short to represent an actual or legitimate RR interval and thus, the processors declare the candidate R-wave and marker to be false and determine that no under detection occurred.

Alternatively, if the new RRI is greater than a predetermined limit (e.g., 200 msec,), the processors further analyze the new beat. At 992, the one or more processors calculate the peak amplitude new/actual R-wave within the beat segment. If the peak amplitude is greater than a predetermined limit (e.g., 0.5 times the minimum value of detected R-wave amplitudes), the processors confirm under-detection. The new beat and new R-wave marker are designated/registered within the CA data set and the process ends.

Optionally, after identifying R-waves within the CA signal, P-wave search windows and/or T-wave search windows may be defined in connection with some or all of the beats. For example, a P-wave search window may be defined to extend 300 ms before the R-wave, while a T-wave search window may be defined to extend 200 ms after the R-wave. Accordingly, by improving the accuracy of R-wave detection in the foregoing manner, embodiments herein also improve the accuracy of identifying P-waves and T-waves, as well as other features of interest within cardiac events.

The process of FIG. 9E may be implemented in connection with various types of systems. For example, the process of FIG. 9E may be implemented as a "re-detection" process in firmware of a device, such as an ICM. While the process of FIG. 9E may be more computationally expensive, as compared to a traditional ORI process, the process of FIG. 9E may be configured to run on an ICM as part of a confirmation or re-detection scheme. For example, CA signals initially analyzed by the ICM (utilizing a conventional ORI process) may be stored in a spin buffer when the conventional ORI process identifies an arrhythmia episode. When the CA signals are stored in the spin buffer, the process of FIG. 9E may be applied to the CA signals as a confirmation or re-detection scheme.

Additionally or alternatively, CA signals may be processed with various front end filters and along different sensing channels by an ICM. The signal filtered and processed along one sensing channel may be temporarily buffered, while the conventional ORI process operates upon CA signals being received over a separate sensing channel. When the ORI process identifies potential arrhythmia, the ICM may apply the process of FIG. 9E to the buffered CA signals.

Additionally or alternatively, the process of FIG. 9E may be implemented partly in firmware of the ICM, while the remaining operations of FIG. 9E are implemented off-line on an external device or remote server. For example, the operations at 980-984 may be implemented in firmware of the ICM, while the remaining operations at 986-992 may be implemented off-line on an external device or remote server. As a further example, the operations of FIG. 9E may be divided in other manners between the ICM, an external device and/or remote server.

As another example implementation, the process of FIG. 9E may be implemented in a cloud-based environment, such as on a remote server and/or distributed between multiple remote processors/servers. For example, a remote server at a medical network may receive CA data sets generated by an ICM. The remote server may analyze the CA data sets off-line, such as in an effort to identify false positive AF detections that are declared by the ICM. The remote server may collect multiple CA data sets and perform batch type processing to analyze multiple CA data sets at one point in time. A remote server or cloud-based network provides substantial computational power well in excess of what would be needed to efficiently process even a large batch of episode electrograms. Hence, a remote server or cloud-based network would afford better R-wave detection and improved arrhythmia discrimination for AF episodes before the CA data sets are presented to a clinician, thereby removing or substantially reducing the amount of time required by a clinician to parse through false positives and distinguish true arrhythmias from false arrhythmias.

Additionally or alternatively, the process of FIG. 9E may be implemented on a local external device, such as a smart phone, tablet device or other device in the possession of the patient. Mobile devices such as smart phones are configured with a ICM application configured to communicate with the ICM. The mobile devices are capable of processing CA data sets as described herein. The mobile device may make a determination, based on the enhanced R-wave detection processes described herein, whether an episode represents a true arrhythmia or instead a false positive driven by inappropriate R-waves. The mobile device may screen out the false positive episodes and prevent the false positive episodes from being uploaded to the remote server. Additionally or alternatively, the mobile device may also provide feedback communication to the ICM (e.g., informing the ICM of the false positives) to allow the ICM to update diagnostic counts that are maintained therein.

In accordance with at least some embodiments, one or more processors herein may identify that the set of device declared R-waves (as designated by the ORI process in the ICM) significantly differs from the confirmation R-waves identified in connection with the process of FIG. 9E. When substantial differences are identified, the one or more processors may send an alert to a clinician to check and/or reprogram sensitivity parameters. Optionally, a "simulated ORI" process may be implemented to analyze a CA data set offline (e.g., in the cloud) upon detection of such different sets of R-waves. The simulated process may test one or more potential ORI configurations and identifies an improved set of device-programmable ORI parameters to decrease the "false-positive burden" at the ICM. Optionally, the improved ORI programming parameters may be automatically pushed back to the ICM. Optionally, the templates created at 986 in FIG. 9E may be utilized to allow embodiments herein to accurately discriminate amongst sinus rhythm, different PVC morphologies, and various forms of (intermittent) block. Applied more broadly to a sufficiently long CA data set (up to and including the entirety of 24-hour monitoring), the R-wave detection processes herein can provide detailed ventricular rhythm diagnostics.

The processes described herein afford an advantage in that the processes identify a point on the QRS complex where the detection occurs in a more consistent manner beat-to-beat as compared to the conventional ORI process. Consistently identifying a detection point in the QRS complex is advantageous, given that R-wave timing is used for multiple reasons, such as a marker point for ensemble creation, for example, as with P-wave detection and ST-segment monitoring. In the event that the detection point is misaligned on a QRS complex, the misalignment creates a challenge, particularly with wider QRS or split QRS, e.g., bundle branch block. Misalignment of the detection point may also create difficulties where R-waves are relatively small and T-waves are relatively large, in which case T-wave detection (instead of R-wave detection) provides reasonable intervals for rate-related diagnostics but obliterates possibility to use other electrogram features for discrimination and enhanced diagnostics.

VI. Alternative Embodiment—Noise Detection Algorithm for CA Signals Sensed by Implantable Cardiac Monitor ($1^{st}$ & $2^{nd}$ Pass)

ICMs are configured to evaluate various features of EGM signals to determine specific cardiac events, such as P-waves, R-waves, arrhythmias, and the like. However, ICMs rely on relative clean EGM signals to detect the features of interest. In certain instances, noise may mimic certain features of interest from a cardiac event and thus give rise to a false detection by the ICM, including but not limited to false device documented markers. The false detection may lead to an inappropriate therapy and/or diagnosis.

In accordance with embodiments herein, a noise detection process is provided that identifies noise based on certain "turn" characteristics within a CA signal. As noted above, the term "turn" means a change in a direction of the CA signal. A turn may be further characterized by an amplitude, frequency and duration. High frequency noise is characterized by very rapid changes in signal direction (as compared to changes in signal direction associated with sinus features of a cardiac event). Embodiments herein evaluate a presence (and characteristics) of high density, significant amplitude turns in a CA signal.

As explained hereafter, in accordance with embodiments herein, a computer implemented method is provided for detecting arrhythmias in cardiac activity. The method comprises, under control of one or more processors configured with specific executable instructions, obtaining a far field cardiac activity (CA) data set that includes far field CA signals for a series of beats; overlaying a segment of the CA signals with a noise search window; identifying turns in the segment of the CA signals; determining whether the turns exhibit a turn characteristic that exceed a turn characteristic threshold; declaring the segment of the CA signals as a noise segment based on the determining operation; shifting the noise search window to a next segment of the CA signal and repeat the analyzing and determining operations; and modifying the CA signal based on the noise segments determined.

Additionally or alternatively, the turn characteristic corresponds to turn amplitude and wherein the determining operation comprises analyzing the turn amplitude relative to a turn amplitude threshold. Additionally or alternatively, the turn characteristic corresponds to turn frequency and wherein the determining operation comprises analyzing the turn frequency relative to a turn frequency threshold. Additionally or alternatively, the method further comprises setting noise flags based on relations between the turn amplitude and turn amplitude threshold and between the turn frequency and turn frequency threshold. Additionally or alternatively, the identifying the turn comprises identifying changes in a signal direction by calculating a first derivate of the CA signals at incremental points along the CA signals and finding the points where a sign of the derivative changes, labeling the points as turns.

Additionally or alternatively, the overlaying operation comprises defining the noise search window to overlap a portion of CA signal that does not overlap with a QRS complex or a T-wave in the segment of the CA signals. Additionally or alternatively, the method further comprises applying an arrhythmia detection process, based on RR interval variability, to the CA signals as modified. Additionally or alternatively, the method further comprises declaring a segment of the CA signals to represent a noisy segment, the modifying operation comprising removing the noisy segment to form noise corrected CA signals, the applying operation applying the arrhythmia detection process to the noise corrected CA signals. Additionally or alternatively, the arrhythmia detection process is performed as a first pass detection process by an on-board R-R interval irregularity (ORI) process that analyzes the CA signals after being modified based on the declaring the noisy segments. Additionally or alternatively, the overlaying, identifying, determining, declaring, shifting, modifying operations are performed by firmware and hardware within an ICM or IMD.

In accordance with embodiments herein, a system is provided for detecting arrhythmias in cardiac activity. The system comprises memory to store specific executable instructions; and one or more processors configured to execute the specific executable instructions for: obtaining a far field cardiac activity (CA) data set that includes far field CA signals for a series of beats; overlaying a segment of the CA signals with a noise search window; identifying turns in the segment of the CA signals; determining whether the turns exhibit a turn characteristic that exceed a turn characteristic threshold; declaring the segment of the CA signals as a noise segment based on the determining operation; shifting the noise search window to a next segment of the CA signal and repeat the analyzing and determining operations; and modifying the CA signal based on the noise segments determined.

Additionally or alternatively, the characteristic may correspond to turn amplitude and wherein the determining operation comprises analyzing the turn amplitude relative to a turn amplitude threshold. Additionally or alternatively, the turn characteristic may correspond to turn frequency and wherein the determining operation comprises analyzing the turn frequency relative to a turn frequency threshold. Additionally or alternatively, the processor is further configured to set noise flags based on relations between a turn amplitude and turn amplitude threshold and between a turn frequency and turn frequency threshold. Additionally or alternatively, the processor is further configured to apply an arrhythmia detection process that is dependent on RR interval variability, wherein the overlaying operation comprises defining the noise search window to overlap a portion of CA signal that does not overlap with a QRS complex or a T-wave in the segment of the CA signals. Additionally or alternatively, the processor is further configured to identify changes in a signal direction by calculating a first derivate of the CA signals at incremental points along the CA signals and find the points where a sign of the derivative changes, labeling the points as turns. Additionally or alternatively, the system further comprises an implantable cardiac monitor that houses the memory and one or more processors, and that houses sensors to obtain the CA signals for the series of beats. Additionally or alternatively, the system further comprises an implantable cardiac monitor that comprises sensors to obtain the CA signals and a telemetry circuit to telemeter the CA signals to a local external device. Additionally or alternatively, the system further comprises a local external device that includes the memory and one or more processors for performing at least a portion of the overlaying, identifying, determining, declaring, shifting, and modifying operations. Additionally or alternatively, the system further comprising a remote server that includes the memory and one or more processors for performing at least a portion of the overlaying, identifying, determining, declaring, shifting, and modifying operations. Hereafter, embodiments of the foregoing method and system are described.

Figure 11:
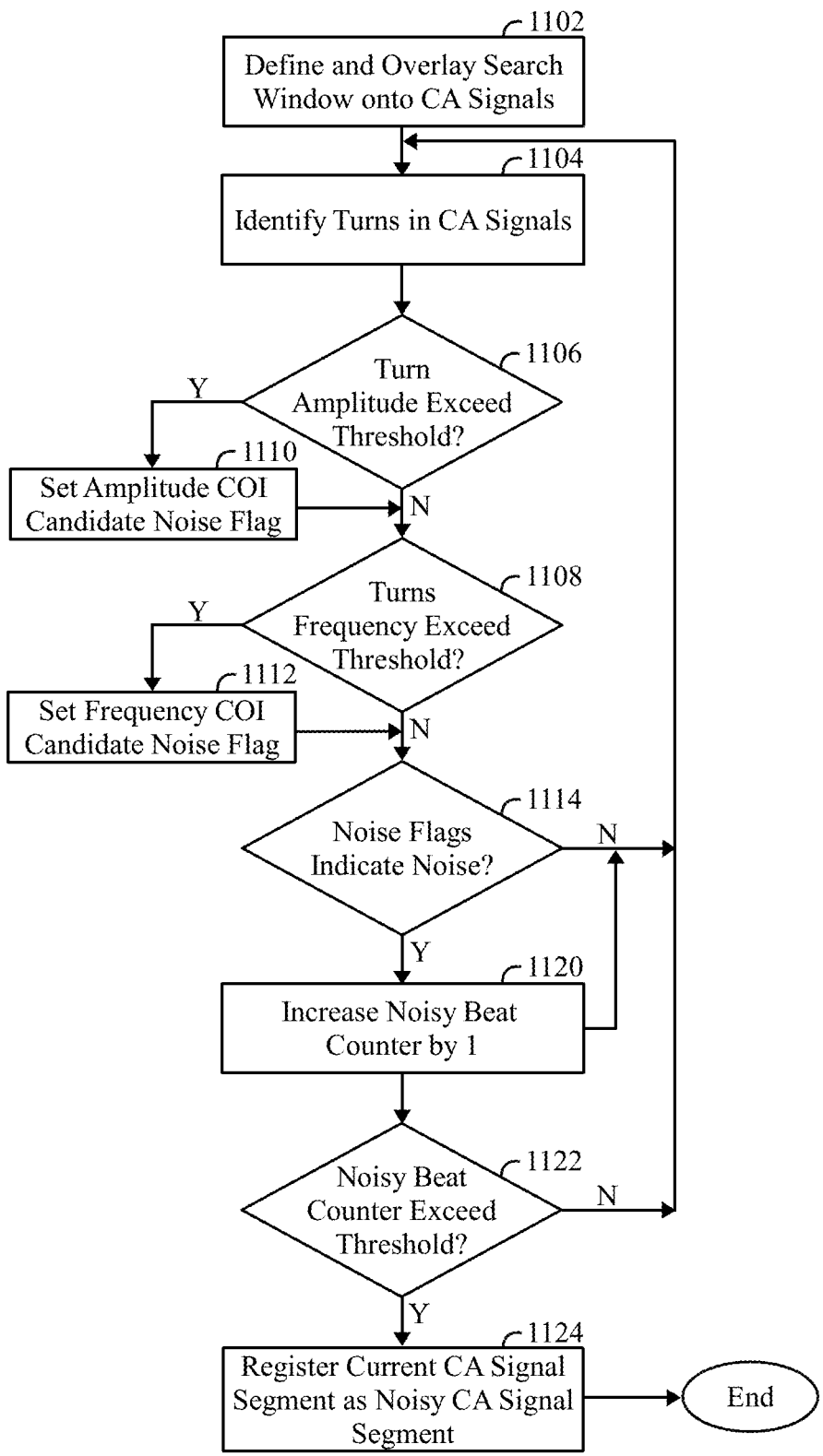
FIG. 11 illustrates a process for identifying noise in accordance with embodiments herein.

FIG. 11 illustrates a process for identifying noise in accordance with embodiments herein. At 1102, the one or more processors define and overlay a noise search window onto the CA signal for which noise detection is to be carried out. The noise search window may vary depending on a nature of the feature for which the CA signal is being analyzed. For example, the ICM may implement an ORI process for AF detection, where the detection process is strongly dependent on the QRS morphology as the AF detection process is based on RR interval variability. Therefore, in an AF detection process that is dependent on RR interval variability, the noise detection process of FIG. 11 defines the noise search window to overlap a portion of CA signal that does not overlap with QRS complex to T-wave. For example, the processors may utilize QRS complex and/or T-wave markers that were identified prior to the process of FIG. 11. As one example, R-wave and T-wave markers may be identified in real-time serially with the process of FIG. 11. As another example, R-wave and T-wave markers may be identified previously before the process of FIG. 11 (which may be performed off-line or non-real-time).

At 1104, the one or more processors evaluate the CA signal within the noise search window to identify turns in the CA signal. For example, the processors identify changes in the signal direction, (i.e., positive to negative or negative to positive) by calculating a first derivate of the CA signal at incremental points along the CA signal and finding points where a sign of the derivative changes from 'positive' to 'negative' or 'negative' to 'positive'. Each time the sign of the derivative changes, the processors label the point as a turn.

Figure 12A:
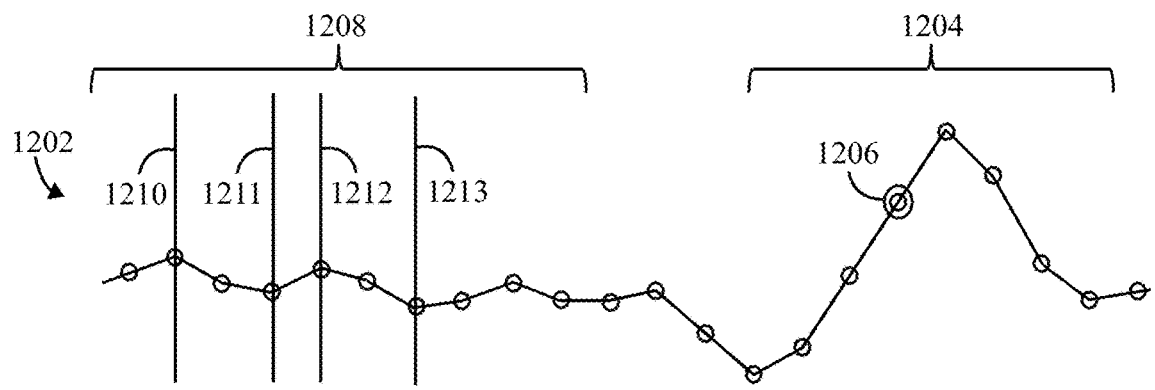
FIG. 12A illustrates an example of a CA signal segment (e.g., a VEGM signal) that includes a QRS complex with an R-wave marker in accordance with embodiments herein.

FIG. 12A illustrates an example of a CA signal segment 1202 (e.g., an EGM signal) that includes a QRS complex 1204 with an R-wave marker 1206. The process of FIG. 11 identifies the R-wave marker 1206 and defines a noise search window 1208 to precede the R-wave marker 1206 by a predetermined time interval. It should be recognized that the location of the R-wave marker 1206 is merely an example, such as corresponding to an intermediate point within the R-wave. Optionally, the R-wave marker may correspond to the peak or other point of the R-wave. The processors evaluate the CA signal in the noise search window 1208 by calculating the derivative at multiple points.

The processors determine the points where the derivative changes sign and labels each sign change as a turn. For example, FIG. 12A shows 4 'turns' (indicated by black vertical lines 1210-1213) marked by change in signal direction. Turns in the remaining portion of CA signal segment 1202 were not used as they fall within the QRS complex 1204 or thereafter in the T-wave portion of the CA signal segment 1202.

Returning to FIG. 11, at 1106-1114, the one or more processors determine whether the turns exhibit turn characteristics that exceed turn characteristic thresholds and thus justify designating the current CA signal segment within the search window to represent noise. At 1106, the one or more processors analyze a turn amplitude characteristic relative to a turn amplitude threshold. The turn amplitude threshold set may be such that turns having an amplitude that exceeds the turn amplitude threshold are considered "significant" turns in size relative to a size of sinus features within a cardiac event. A "significant" turn represents a portion of the CA signal that could interfere with aspects of the feature detection processes implemented herein. The turn amplitude threshold may be set in various manners, such as based on a percentage of a sinus feature. For example, the turn amplitude threshold may be set to equal 20% of an amplitude of a peak of an R-wave, 120% of an amplitude of a peak of a P-wave or T-wave and the like. Optionally, the amplitude threshold may be set as a predetermined voltage and/or by subtracting a predetermined voltage from an amplitude of the peak of an R-wave and/or adding a predetermined voltage to an amplitude of a peak of a P-wave or T-wave. At 1106, when the turn amplitude exceeds the turn amplitude threshold, the process determines that the turn has sufficient amplitude to potentially interfere with later analysis for detecting sinus features of interest, such as an R-wave. Thus, flow moves to 1110 and sets an amplitude characteristic of interest (COI) candidate noise flag. The amplitude COI candidate noise flag is set to indicate that the potential exists that the current turn is sufficiently large (relative to amplitudes of sinus features), such that, if the CA signal segment is noise, the CA signal segment should be removed. At 1106, when the turn amplitude does not exceed the threshold, flow advances to 1108 and the amplitude COI candidate noise flag remains unset or at a zero/low value.

At 1108, the one or more processors analyze a turn frequency characteristic by comparing the turn frequency characteristic with a turn frequency threshold. The turn frequency characteristic represents the number of turns (changes in direction) within the search window and/or a desired portion of the search window. The turn frequency threshold may be pre-programmed by a user and/or automatically set throughout operation based on prior CA signals. For example, the turn frequency threshold may be set to 5 Hz, 10 Hz and the like, where a turn frequency characteristic of a current search window should exceed the 5 Hz, 10 Hz or other threshold before being considered to have a sufficiently high frequency to be indicative of noise. Optionally, the turn frequency threshold may be set to be a percentage of the heart rate, RR interval and the like. When the turn frequency characteristic exceeds the turn frequency threshold, flow moves from 1108 to 1112. At 1112, the one or more processors set a frequency COI candidate noise flag. The frequency COI candidate noise flag indicates that the turns occur with sufficient frequency to be indicative of noise. At 1108, when the turn frequency does not exceed the turn frequency threshold, flow advances to 1114 and the frequency COI candidate noise flag remains unset or at a zero/low value.

Optionally, the noise determination at 1106-1112 may be modified to utilize amplitude alone, frequency alone, or combination of both. For example, in embodiments that utilize amplitude alone, the operations at 1108, 1112 may be omitted. In embodiments that utilize frequency alone, the operations at 1106, 1110 may be omitted.

At 1114, the one or more processors review the amplitude and/or frequency COI candidate noise flags to determine whether the flags indicate that the CA signal segment should be classified as noise. In the present example, the flags may represent binary values, namely set or unset. Additionally or alternatively, at 1110 and 1112, the flags may record information representative of a degree to which the turn amplitude and/or turn frequency characteristics exceed the corresponding turn amplitude and frequency threshold. For example, when the turn amplitude characteristic is relatively close to the turn amplitude threshold, the operation at 1110 may record a small value (e.g., 2-4 on a scale of 1-10). Alternatively, when the turn amplitude characteristic substantially exceeds the turn amplitude threshold, the operation at 1110 may record a larger value (e.g., 7-9 on a scale of 1-10). Similarly, at 1112, the process may set the values for the frequency COI candidate noise flag on a scale of 1-10 to be representative of a degree to which the turn frequency characteristic exceeds the turn frequency threshold.

At 1114, when the amplitude and frequency COI candidate noise flags indicate that the CA signal segment includes excessive noise, flow moves to 1120. At 1114, when the noise flags do not indicate a presence of noise, the noise detection process of FIG. 11 ends for a current beat or CA signal segment. When the noise flags indicate a presence of noise, the process moves to 1120. At 1120, the one or more processors increment a noisy beat counter by one. The noisy beat counter maintains a running count of the number of beats within a longer CA signal segment (e.g., 30-60 seconds) that satisfy one or both of the turn amplitude and turn frequency criteria.

At 1122, the one or more processors compare a current count for the noisy beat counter to a noise threshold. For example, the comparison may determine a percentage of noisy beats that were counted out of a total number of beats. Alternatively, the noise threshold may merely represent a predetermined number of beats. When the noisy beat count does not exceed the threshold, the process of FIG. 11 ends. Alternatively, when the noisy beat count exceeds the threshold, flow continues to 1124.

At 1124, the one or more processors register the current CA signal segment as a noisy CA signal segment. By way of example, when a desired number X beats are classified as noisy out of a total number of beats Y, the processors register the current CA signal segment of Y beats as noisy. For example, for a given CA signal segment, when a percentage (%) of noisy beats is greater than a threshold (e.g., 25%), then an overall entire CA signal segment (e.g., 30 second strip or 1 minute strip of EGM signals for a CA data set) may be declared as 'noisy' and may be rejected from further analysis. For example, when the operations of FIG. 11 declare a 30 second EGM strip to represent a noisy segment, the operation at 304 in FIG. 3 may reject the entire 30 second CA data set and return to 302 to obtain a new CA data set (e.g., a new 30 second EGM strip).

Optionally, at 1124, a smaller portion of a CA data set may be rejected and not an entire 30 second CA data set. For example, when a current CA signal segment (e.g., 10-15 seconds of EGM signals or 10-20 beats) is deemed to be noisy, only the individual noisy beats or the set of noising beats may be removed from the overall CA data set (e.g., remove a 10-15 second CA signal segment from a 30-60 second CA signal segment). When noisy segments of a CA dataset are removed, the remaining segments of the CA data set represent noise-corrected CA signals. In the example of FIG. 3, the noise-corrected CA signals may be passed from 304 to 306 for further processing. Optionally, the noise detection process of FIG. 11 may be performed as part of a first pass arrhythmia detection process, where the noise detection operations are performed by firmware and hardware within an ICM or IMD.

Figure 12B:
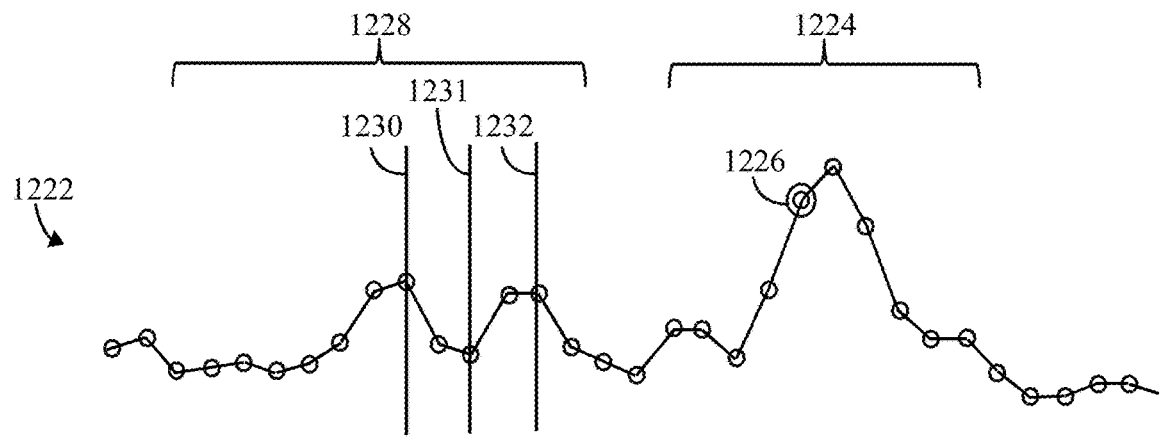
FIG. 12B illustrate example CA signals that are analyzed by the process of FIG. 11 in accordance with embodiments herein.
Figure 12C:
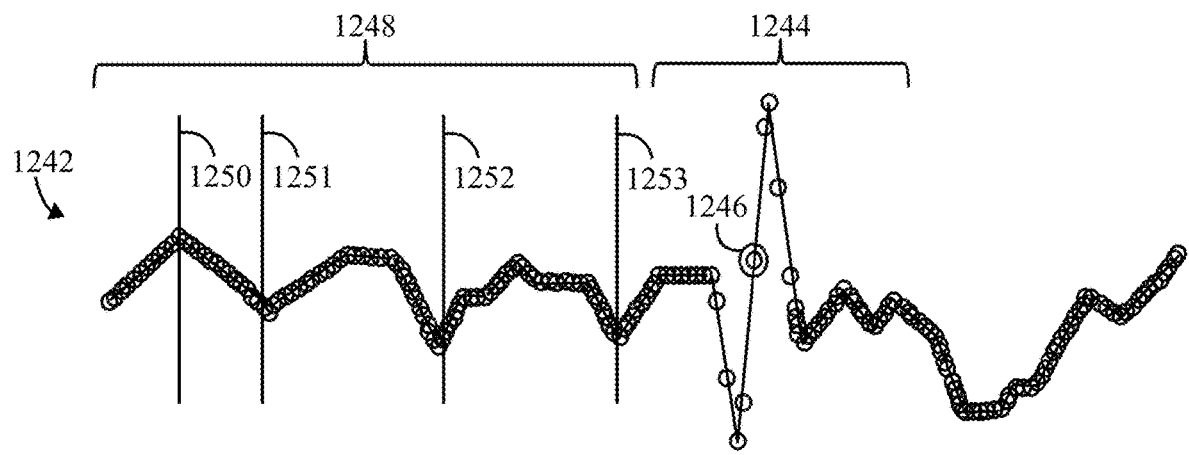
FIG. 12C illustrate example CA signals that are analyzed by the process of FIG. 11 in accordance with embodiments herein.

FIGS. 12B and 12C illustrate example CA signals 1222 and 1242, respectively, that are analyzed by the process of FIG. 11 in accordance with embodiments herein. The CA signals 1222 and 1242 include QRS complexes 1224 and 1244, respectively, with R-wave markers 1226 and 1246. The process of FIG. 11 identifies the R-wave markers 1226 and 1246 and define noise search windows 1228 and 1248 to precede the R-wave markers 1226 and by a predetermined time interval. The processors determine the points where the derivatives change signs and label each sign change as a turn. In FIG. 12B, 3 'turns' (indicated by black vertical lines 1230-1232) are marked by change in signal direction. In FIG. 12C, 4 'turns' are indicated by vertical lines 1250-1253.

In FIG. 12B, the amplitudes of the turns at 1230-1232 are sufficiently large to exceed the turn amplitude threshold and thus would result in the process of FIG. 11 setting the amplitude COI candidate noise flag at 1110. Next, the process of FIG. 11 would analyze the frequency of the turns at 1230-1232 and determine that the frequency is sufficiently high to set the frequency COI candidate noise flag at 1112.

In FIG. 12C, the CA signal segment 1242 corresponds to an atrial flutter cardiac event. Regardless of whether the amplitudes of the turns at 1250-1253 exceed an amplitude threshold, the frequency of the turns at 1250-1253 is substantially lower than frequencies indicative of noise. Accordingly, the process of FIG. 11 would not classify the CA signal segment 1242 as noise and instead would leave the CA signal segment 1242 to be further analyzed for arrhythmia detection.

Figure 12D:
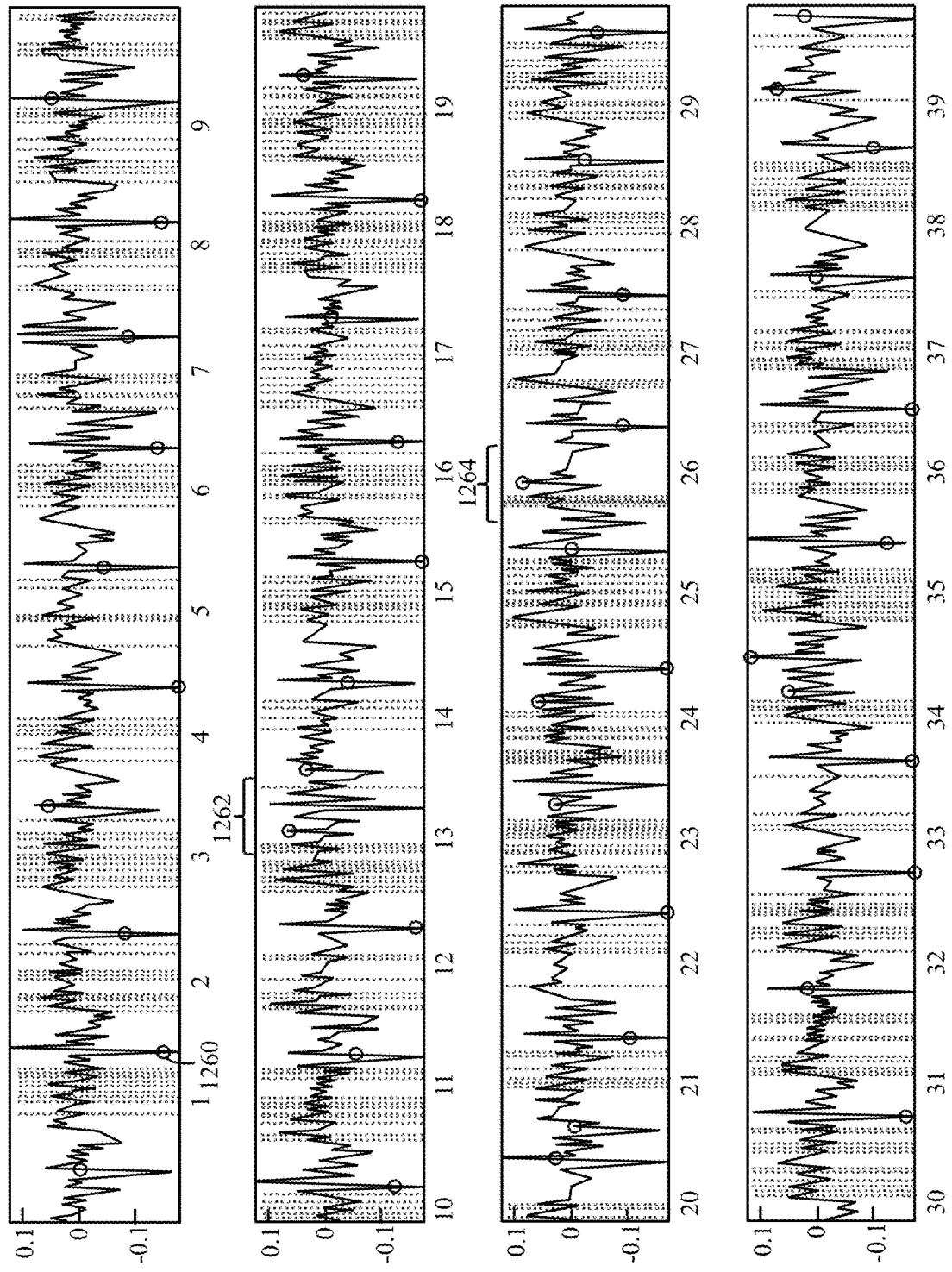
FIG. 12D illustrates strips of stored EGM signals collected by an ICM utilizing a conventional on-device noise detection circuit in accordance with embodiments herein.

FIG. 12D illustrates strips of stored EGM signals (corresponding to CA signals) collected by an ICM utilizing a conventional on-device noise detection circuit. The EGM signal of FIG. 12D includes noise segments which indicate that the noise segments did not trigger a noise mode at the device noise detection circuit. Had the device noise detection circuit been triggered, the noise segments would have been omitted/blanked. The EGM signals of FIG. 12D were characterized by the ORI process on the ICM to include arrhythmia episodes. The ORI process identified R-waves as indicated at the circular R-wave markers 1260. While the majority of the R-wave markers 1260 correctly identify R-waves, some of the R-wave markers are incorrect. For example, the R-wave markers in CA signal segment 1262 and the R-wave marker in CA signal segment 1264 represent false R-wave markers.

Also, in conventional R-wave detection processes, when the signal exhibits substantial noise, the noise may cause the location of the R-wave marker to be incorrectly positioned. Accordingly, while a CA signal segment may include an R-wave, the R-wave detection process may incorrectly position the R-wave marker within the QRS complex. In accurate positioning of R-wave markers may confine to other discrimination operations that rely on the R-wave marker location, such as in connection with setting search windows for other sinus and arrhythmia features of interest. As one example, when a discrimination operation utilizes an ensemble average of P-waves in connection with searching for a P-wave, the P-wave search windows will vary based on the location of the R-wave marker. Thus, incorrect positioning of the R-wave marker may in turn lead to incorrect positioning of the P-wave search windows utilized to develop the ensemble average of the P-wave. Despite a presence of noise detection circuitry in conventional ICM, it has been estimated that at least one conventional onboard AF detection process may declare approximately 17% of false AF episodes as such due to noise that is falsely detected as R-waves.

In accordance with embodiments herein, noisy signal segments may be identified based on turns that have amplitude and frequency characteristics that exceed corresponding thresholds. The process of FIG. 11 may be implemented in real time on an ICM contemporaneous with the cardiac activity being analyzed. For example, the process of FIG. 11 may be programmed to run within firmware on an ICM, while analyzing real time EGM signals and/or analyzing EGM signals that have been temporarily stored in a spin buffer. For example, the process of FIG. 11 may be implemented in an ICM as part of a confirmation process that analyzes pre-recorded EGM signals (e.g., previously stored in a spin buffer). The EGM signals may be stored in response to the ICM detecting an episode utilizing a conventional arrhythmia detection process.

Additionally or alternatively, the process of FIG. 11 may be implemented non-real time, and applied as a retroactive or off-line confirmation process when analyzing CA data sets that include device documented arrhythmias. If noise is found that would influence an arrhythmia detection algorithm, the CA signal segment having the noise may be flagged or removed from the CA signal data set. Additionally or alternatively, the process may record a notation in connection with the CA data set indicating that the device documented episode is based on a CA signal segment that exhibits substantial noise.

Additionally or alternatively, the noise detection process of FIG. 11 may be performed on an external instrument, such as a local mobile device (e.g., smart phone, tablet device, laptop computer) and/or a remote network server. When implemented at a local mobile device, the noise detection process may be performed upon incoming CA data sets received by the local mobile device from an ICM before the local mobile device transmits the CA data set to the remote network server. When implemented at a remote network server, the noise detection process may be performed upon incoming CA data sets before displaying the CA data set to a clinician. The noise detection process may flag, hide or discard CA signal segments that are classified as noisy segments by the process of FIG. 11.

A model has been implemented based on an embodiment of the noise detection process of FIG. 11. The model analyzed ECG signals for 668 AF episodes that were identified by an ICM to include AF (e.g., 668 device documented AF episodes). From analysis of the 668 device documented AF episodes by the model, 36 episodes (8.9%) were identified to exhibit excess noise and were screened out by the noise detection process of FIG. 11. The 36 episodes identified by the present model were confirmed through trained observers to represent false positive AF episodes. In addition, the model did not filter out any true AF episodes. In accordance with embodiments herein, the noise detection process of FIG. 11 may be implemented at an early point during and arrhythmia detection process, such that CA signal segments that exhibit excess noise are removed from further analysis by the arrhythmia detection process.

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

CLOSING

The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and physical characteristics described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A system for detecting arrhythmias in cardiac activity, comprising:
  memory to store specific executable instructions;
  one or more processors configured to execute the specific executable instructions for:
    obtaining a far field cardiac activity (CA) data set that includes far field CA signals for beats;
    calculating an adaptive sensitivity level based on;
      automatically iteratively analyzing a beat segment of interest by:
        comparing the beat segment of interest to a current adaptive sensitivity level to determine whether one or more R-waves are present within the beat segment of interest;
        repeating the iterative analyzing operation while progressively adjusting the current adaptive sensitivity level until i) the one or more R-waves are detected in the beat segment of interest and/or ii) the current adaptive sensitivity level reaches a sensitivity limit; and detecting an arrhythmia within the beat segment of interest based on a presence or absence of the one or more R-waves, wherein the processor is further configured to confirm or deny a bradycardia episode, as the arrhythmia, based on a number of X beats within a bradycardia zone out of a total of Y beats within the CA data set; and recording results of the detecting of the arrhythmia.

2. The system of claim 1, wherein the applying, calculating and automatically iteratively analyzing operations are performed as a second pass confirmation for an arrhythmia episode declared by a first pass arrhythmia detection algorithm implemented by an implantable device.

3. The system of claim 2, wherein the CA data set includes device documented markers in combination with the CA signals, the CA data set generated by the implantable device in connection with the first pass arrhythmia detection algorithm, the first pass arrhythmia detection algorithm declaring the arrhythmia episode to be one of a bradycardia, tachycardia, asystole or atrial fibrillation episode.

4. The system of claim 1, wherein the processor is configured to calculate the current adaptive sensitivity level by determining amplitudes for one or more features of the beat segment of interest, the sensitivity limit based on the amplitudes; and wherein the comparing operation includes determining whether at least a portion of the beat segment of interest exceed the current adaptive sensitivity level.

5. The system of claim 3, wherein the processor is configured to determine the current adaptive sensitivity level based on a comparison of an ensemble R-wave peak, ensemble T-wave peak and ensemble P-wave peak amplitudes and/or variability that represent amplitudes and/or variability for the one or more R-waves.

6. The system of claim 1, wherein the processor is configured to analyze the beat segment of interest iteratively while adjusting the current adaptive sensitivity level to increase resolution during each iterative analysis until reaching the sensitivity limit or specific exiting criteria.

7. A system for detecting arrhythmias in cardiac activity, comprising:

memory to store specific executable instructions;
one or more processors configured to execute the specific executable instructions for:
obtaining a far field cardiac activity (CA) data set that includes far field CA signals for beats;
calculating an adaptive sensitivity level based on;
automatically iteratively analyzing a beat segment of interest by:
comparing the beat segment of interest to a current adaptive sensitivity level to determine whether one or more R-waves are present within the beat segment of interest;
repeating the iterative analyzing operation while progressively adjusting the current adaptive sensitivity level until i) the one or more R-waves are detected in the beat segment of interest and/or ii) the current adaptive sensitivity level reaches a sensitivity limit; and
detecting an arrhythmia within the beat segment of interest based on a presence or absence of the one or more R-waves, wherein the processor is further configured to confirm or deny an asystole episode, as the arrhythmia, when the beat segment of interest exhibits no detected electrical activity for a period of time that exceeds an asystole threshold; and
recording results of the detecting of the arrhythmia.

8. The system of claim 1, wherein the processor is configured to apply a feature enhancement function to the CA signals to enhance at least one of an R-wave feature, T-wave feature, P-wave feature and/or suppresses noise to form an enhanced feature in the CA data set; and to calculate the adaptive sensitivity level and sensitivity limit based on the enhanced feature from one or more beats within the CA data set.

9. The system of claim 8, wherein the processor is configured to apply a normalization function and a non-linear scaling function to the CA signals as the feature enhancement function.

10. A system for detecting arrhythmias in cardiac activity, comprising:

memory to store specific executable instructions;
one or more processors configured to execute the specific executable instructions for:
obtaining a far field cardiac activity (CA) data set that includes far field CA signals for beats;
identifying a T-wave characteristic of interest (COI) and an R-wave COI from the CA signals;
adjusting profile parameters of a sensitivity profile based on the T-wave COI and R-wave COI, the sensitivity profile defining a time-varying sensitivity level and a sensitivity limit;
automatically iteratively analyzing a beat segment of interest by:
comparing the beat segment of interest to the time-varying sensitivity level to determine whether an R-wave is detected within the beat segment of interest; and
detecting an arrhythmia within the beat segment of interest based on a presence or absence of the R-wave; and
recording results of the detecting of the arrhythmia.

11. The system of claim 10, wherein the processor is configured to perform the identifying and adjusting operations on a beat by beat basis.

12. The system of claim 10, wherein the processor is further configured to identify, in connection with the R-wave COI, a rise rate of a current beat and determining whether the rise rate of the current beat exceeds a rise rate of a preceding beat by more than a R-wave rise rate threshold.

13. The system of claim 10, wherein the processor is further configured to adjust at least one of a start sensitivity parameter that defines a start sensitivity of the sensitivity profile.

14. The system of claim 10, wherein the processor is further configured to identify, in connection with the T-wave COI and R-wave COI, at least one of a rapid rise characteristic, a rapid heart rate characteristic, T/R-wave ratio characteristic or a T-wave-to-refractory proximity characteristic.

15. The system of claim 10, wherein the processor is further configured to adjust, based on the T-wave COI and R-wave COI, at least one of a refractory period duration, start sensitivity, decay rate, or sensitivity limit parameter, the start sensitivity parameter defining a start sensitivity of the sensitivity profile, the refractory period duration parameter defining a blanking interval, a decay rate parameter defining a slope of a linear time-varying sensitivity level decline, the sensitivity limit parameter defining a lowest sensitivity level that linear sensitivity level decline is not allowed to go below.

16. A system for detecting arrhythmias in cardiac activity, comprising:
- memory to store specific executable instructions;
- one or more processors configured to execute the specific executable instructions for:
  - obtaining a far field cardiac activity (CA) data set that includes far field CA signals for a series of beats;
  - applying an initial R-wave detection process to the CA signals and designating R-wave markers in the CA data set, the R-wave markers separated by RR intervals;
  - applying an R-wave confirmation process that comprises:
    - calculating instantaneous and average RR intervals between the R-wave markers designated by the initial R-wave detection process;
    - identifying a suspect beat segment from the CA signals based on a relation between the instantaneous and average RR intervals;
    - searching the suspect beat segment for a potential under detected beat by comparing the suspect beat segment to one or more QRS templates; and
    - when an under detected beat is identified from the suspect beat segment, designating a new R-wave marker within the CA data set corresponding to the under detected beat;
  - detecting an arrhythmia within CA data set based on the R-wave markers designated during the initial R-wave detection process and R-wave confirmation process; and
  - recording results of the detecting of the arrhythmia.

17. The system of claim 16, wherein the processor is further configured to analyze the relation between the instantaneous and average RR intervals, wherein the instantaneous and average RR intervals are identified by stepping through successive beat segments along the CA signal to search for potential under detected beats, the instantaneous RR interval representing an interval between a current R-wave marker and one of a preceding and succeeding R-wave marker, the average RR interval representing an average interval for a predetermined number of RR intervals related to a current RR interval.

18. The system of claim 16, wherein the relation utilized to identify the suspect beat segment represents a difference between the instantaneous and average RR intervals that exceeds an RR interval range threshold.

19. The system of claim 16, wherein the processor is further configured to apply a feature enhancement to the CA signals to form enhanced R-wave or T-wave features in the CA data set.

20. The system of claim 19, wherein the processor is further configured to identify the suspect beat segment by overlaying a search window on a current beat segment and comparing i) the instantaneous RR interval for a current beat within the search window and ii) the average RR interval corresponding to a collection of beats within the search window, the comparison being performed while iteratively stepping the search window through the CA signals beat by beat.

21. The system of claim 16, wherein the processor is further configured to build a library of QRS templates based on morphologies of beats detected in the CA signals; identify a current QRS segment from the CA signals; compare the current QRS segment to the library of QRS templates; when the current QRS segment does not match the QRS templates, add a new QRS template to the library based on the current QRS segment.

22. The system of claim 7, wherein the applying, calculating and automatically iteratively analyzing operations are performed as a second pass confirmation for an arrhythmia episode declared by a first pass arrhythmia detection algorithm implemented by an implantable device.

23. The system of claim 22, wherein the CA data set includes device documented markers in combination with the CA signals, the CA data set generated by the implantable device in connection with the first pass arrhythmia detection algorithm, the first pass arrhythmia detection algorithm declaring the arrhythmia episode to be one of a bradycardia, tachycardia, asystole or atrial fibrillation episode.

24. The system of claim 7, wherein the processor is configured to calculate the current adaptive sensitivity level by determining amplitudes for one or more features of the beat segment of interest, the sensitivity limit based on the amplitudes; and wherein the comparing operation includes determining whether at least a portion of the beat segment of interest exceed the current adaptive sensitivity level.

25. The system of claim 7, wherein the processor is configured to determine the current adaptive sensitivity level based on a comparison of an ensemble R-wave peak, ensemble T-wave peak and ensemble P-wave peak amplitudes and/or variability that represent amplitudes and/or variability for the one or more R-waves.

26. The system of claim 7, wherein the processor is configured to analyze the beat segment of interest iteratively while adjusting the current adaptive sensitivity level to increase resolution during each iterative analysis until reaching the sensitivity limit or specific exiting criteria.

27. The system of claim 7, wherein the processor is configured to apply a feature enhancement function to the CA signals to enhance at least one of an R-wave feature, T-wave feature, P-wave feature and/or suppresses noise to form an enhanced feature in the CA data set; and to calculate the adaptive sensitivity level and sensitivity limit based on the enhanced feature from one or more beats within the CA data set.

28. The system of claim 27, wherein the processor is configured to apply a normalization function and a non-linear scaling function to the CA signals as the feature enhancement function.

* * * * *